(12) United States Patent
Bellacosa et al.

(10) Patent No.: US 11,883,413 B2
(45) Date of Patent: Jan. 30, 2024

(54) INHIBITION OF THYMINE DNA GLYCOSYLASE IN THE TREATMENT OF CANCER

(71) Applicants: Institute For Cancer Research, Philadelphia, PA (US); Institut Curie, Paris (FR); Institut de Genetique et de Biologie Moleculaire et Cellulaire, Illkrich (FR)

(72) Inventors: Alfonso Bellacosa, Philadelphia, PA (US); Rossella Tricarico, Philadelphia, PA (US); Tim Yen, Philadelphia, PA (US); Vikram Bhattacharjee, Philadelphia, PA (US); Pietro Mancuso, Philadelphia, PA (US); Lionel Larue, Paris (FR); Irwin Davidson, Ilkrich (FR)

( * ) Notice: Subject to any disclaimer, the term of this patent is extended or adjusted under 35 U.S.C. 154(b) by 21 days.

(21) Appl. No.: 17/358,852

(22) Filed: Jun. 25, 2021

(65) Prior Publication Data
US 2022/0054500 A1 Feb. 24, 2022

Related U.S. Application Data

(63) Continuation of application No. 15/084,680, filed on Mar. 30, 2016, now Pat. No. 11,077,121, which is a continuation of application No. PCT/US2014/058240, filed on Sep. 30, 2014.

(60) Provisional application No. 61/884,478, filed on Sep. 30, 2013.

(51) Int. Cl.
| | |
|---|---|
| *A61K 31/5575* | (2006.01) |
| *A61K 31/122* | (2006.01) |
| *A61K 31/277* | (2006.01) |
| *A61K 31/475* | (2006.01) |
| *A61K 31/495* | (2006.01) |
| *A61K 31/546* | (2006.01) |
| *A61P 35/00* | (2006.01) |
| *A61K 31/609* | (2006.01) |
| *A61K 31/473* | (2006.01) |
| *A61K 31/404* | (2006.01) |
| *A61K 31/353* | (2006.01) |
| *A61K 33/243* | (2019.01) |
| *A61K 33/24* | (2019.01) |

(52) U.S. Cl.
CPC ........ *A61K 31/5575* (2013.01); *A61K 31/122* (2013.01); *A61K 31/277* (2013.01); *A61K 31/353* (2013.01); *A61K 31/404* (2013.01); *A61K 31/473* (2013.01); *A61K 31/475* (2013.01); *A61K 31/495* (2013.01); *A61K 31/546* (2013.01); *A61K 31/609* (2013.01); *A61K 33/24* (2013.01); *A61K 33/243* (2019.01); *A61P 35/00* (2018.01); *C12N 2740/15043* (2013.01)

(58) Field of Classification Search
CPC ... A61P 35/00; A61K 31/5575; A61K 31/122; A61K 31/277; A61K 31/475; A61K 31/495; A61K 31/546
USPC .......................................... 424/78.08; 514/415
See application file for complete search history.

(56) References Cited

U.S. PATENT DOCUMENTS

| | | | |
|---|---|---|---|
| 8,119,109 B2 * | 2/2012 | Tamarkin | A61Q 15/00 424/68 |
| 8,268,352 B2 | 9/2012 | Vaya et al. | |
| 8,466,193 B2 | 6/2013 | Verner et al. | |
| 8,927,516 B2 * | 1/2015 | Bellacosa | A61K 31/7068 514/44 A |
| 9,241,998 B2 | 1/2016 | Bose et al. | |
| 10,220,051 B2 * | 3/2019 | Bellacosa | C12N 15/1137 |
| 11,077,121 B2 * | 8/2021 | Bellacosa | A61K 31/473 |
| 2003/0139363 A1 | 7/2003 | Kay et al. | |
| 2003/0229001 A1 | 12/2003 | Zarling et al. | |
| 2006/0128777 A1 | 6/2006 | Bendall et al. | |
| 2006/0142231 A1 | 6/2006 | Ashworth et al. | |
| 2006/0241186 A1 | 10/2006 | Gerson et al. | |
| 2009/0062196 A1 | 3/2009 | D'Andrea et al. | |
| 2011/0190390 A1 | 8/2011 | Murray et al. | |
| 2012/0156144 A1 * | 6/2012 | Tamarkin | A61P 31/10 424/43 |
| 2013/0244920 A1 | 9/2013 | Lee et al. | |

(Continued)

FOREIGN PATENT DOCUMENTS

| | | |
|---|---|---|
| WO | 9428127 | 12/1994 |
| WO | 2004006906 | 1/2004 |
| WO | 2011130429 | 10/2011 |

OTHER PUBLICATIONS

Scheel et al., "Toll-like receptor-dependent activation of several human blood cell types by protamine-condensed mRNA", 2005, Eur. J. Immunol., 35(5), pp. 1557-1566. (DOI 10.1002/eji. 200425656) (Year: 2005).*

(Continued)

*Primary Examiner* — Raymond J Henley, III
(74) *Attorney, Agent, or Firm* — Ballard Spahr, LLP

(57) ABSTRACT

The invention provides compositions, kits, and methods for inducing growth arrest, differentiation, or senescence of cancer cells that express thymine DNA glycosylase, and treating the cancer accordingly. The methods comprise inhibiting expression or biologic activity of thymine DNA glycosylase in cancer cells. Inhibition of thymine DNA glycosylase in cancer cells may induce the cells to revert to a healthy, non-cancerous phenotype and/or may induce the cells to senesce. Cancer cells include melanoma, lung, prostate, pancreatic, ovarian, brain, colon, recto-sigmoid colon, and breast cancer cells.

7 Claims, 45 Drawing Sheets
Specification includes a Sequence Listing.

(56) References Cited

U.S. PATENT DOCUMENTS

2013/0303588 A1 11/2013 Bellacosa et al.
2015/0164934 A1 6/2015 Bellacosa et al.

OTHER PUBLICATIONS

Weide et al., "Direct Injection of Protamine-protected mRNA: Results of a Phase 1/2 Vaccination Trial in Metastatic Melanoma Patients", 2009, J. Immunother., vol. 32, No. 5, pp. 498-507. (Year: 2009).*
Aithal, et al., "Evaluation of pharmacokinetic, biodistribution, pharmacodynamic, and toxicity profile of free juglone and its sterically stabilized liposomes", Journal of Pharmaceutical Sciences, vol. 100, No. 8, Aug. 2011, pp. 3517-3528.
Aithal, et al., "Juglone, a naphthoquinone from walnut, exerts cytotoxic and genotoxic effects against cultured melanoma tumor cells", Cell Biology International, vol. 33, No. 10, Oct. 1, 2009, pp. 1039-1049.
Aithal, et al., "Tumor Growth Inhibitory Effect of Juglone and its Radiation Sensitizing Potential: In Vivo and In Vitro Studies", Integrative Cancer Therapies, vol. 11, No. 1, Mar. 1, 2012, pp. 68-80.
Awada, et al., "Prolonged Schedule of Temozolomide (Temodal) plus liposomal doxorubicin (Caelyx) in advanced solid cancers", Anti-Cancer Drugs, vol. 15, No. 5, Jun. 2004, pp. 499-502.
Boorstein, R.J., et al., "Definitive Identification of Mammalian 5-Hydroxymethyluracil DNA N-Glycosylase Activity as SMUG1," J. Biol. Chem., vol. 276, No. 45 (Nov. 9, 2001), pp. 41991-41997.
Burris, H.A., et al., "Improvements in Survival and Clinical Benefit with Gemcitabine as First-Line Therapy for Patients with Advanced Pancreas Cancer: A Randomized Trial", J. Clin. Oncol., vol. 15, No. 6, Jun. 1997, pp. 2403-2413.
Cortellino, S., et al., "Thymine DNA Glycosylase is Essential for Active DNA Demethylation by Linked Deamination-Base Excision Repair", Cell, 146, 2011, pp. 67-79.
Cottu, et al., "High-dose sequential epirubicin and cyclophosphamide with peripheral blood stem cell support for advanced breast cancer: results of a phase II study", British Journal of Cancer, vol. 85, No. 9, Nov. 2, 2001, pp. 1240-1246.
International Search Report issued in related application PCT/US14/58240 dated Sep. 7, 2016.
Ji, et al., "Juglone-induced apoptosis in human gastric cancer SGC-7901 cells via the mitochondrial pathway", Experimental and Toxicologic Pathology, vol. 63, No. 1-2, Jan. 1, 2011, pp. 69-78.
Kumar, et al., "Cytotoxic, genotoxic and oxidative stress induced by 1,4-naphthoquinone in B16F1 melanoma tumor cells", Toxicology In Vitro, vol. 23, No. 2, Mar. 1, 2009, pp. 242-250.
Kunz, C., et al., "Base Excision by Thymine DNA Glycosylase Mediates DNA-Directed Cytotoxicity of 5-Fluorouracil," PLoS Biology, vol. 7, Issue 4 (Apr. 2009), pp. 0967-0979.
Leoni, L., et al., "Bendamustine (Treanda) Displays a Distinct Pattern of Cytotoxicity and Unique Mechanistic Features Compared with other Alkylating Agents", Clin. Cancer Res., 2008; 14(1), Jan. 1, 2008, pp. 309-317.
Mini, E., et al., "Cellular pharmacology of gemcitabine," Ann. Oncol. 17, Suppl. 5:v7-12, 2006.
Montenegro, et al. "Cytotoxic activity of naphthoquinones with special emphasis on juglone and its 5-0-methyl derivative", Chemico-Biological Interactions, vol. 184, No. 3, Mar. 30, 2010, pp. 439-448.
Mook, et al., "Small molecule modulators of Wnt/[beta]-catenin signaling", Bioorganic and Medicinal Chemistry Letters, Pergamon, Amsterdam, NL, vol. 23, No. 7, Jan. 30, 2013, pp. 2187-2191.
Petronzelli, F., et al., "Biphasic Kinetics of the Human DNA REpair Protein MED1 (MBD4), a Mismatch-specific DNA N-Glycosylase," J. Biol. Chem., vol. 275, No. 42, (Oct. 20, 2000) pp. 32422-32429.
Stailings-Mann, et al., "A novel small-molecule inhibitor of protein kinase c[iota] blocks transformed growth of non-small-cell lung cancer cells", Cancer Research, American Association for Cancer Research, vol. 66, No. 3, Feb. 1, 2006, pp. 1767-1774.
Tozawa, et al., "Gold compounds inhibit adhesion of human cancer cells to vascular endothelial cells", Cancer Letters, vol. 196, No. 1, Jun. 1, 2003, pp. 93-100.
Vilpo, J.A., et al., "Metabolism, Incorporation into DNA, and Interactions with 1-beta-D-arabinofuranosylcytosine of 5-hydroxymethyl-2'-deoxyuridine in human promyelocytic leukemia cells (HL-60)1," Cancer Res., 48:3117-22, 1988.
Wagner, et al., "Phase I of trial of two schedules of vincristine, oral irinotecan, and temozolomide (VOIT) for children with relapsed or refractory solid tumors: A Children's Oncology Group phase I consortium study", Pediatric Blood and Cancer, vol. 54, Jan. 4, 2010, pp. 538-545.
Wagner, et al., "Pilot stody of vincristine, oral irinotecan, and temozolomide (VOIT regimen) combined with bevacizumab in pediatric patients with recurrent solid tumors or brain tumors", Pediatric Blood and Cancer, vol. 60, No. 9, Sep. 29, 2013, pp. 1447-1451.
Xu, et al., "Thymine DNA Glycosylase is a Positive Regulator of Wnt Signaling in Colorectal Cancer", J. Biol. Chem., vol. 289, No. 13, Mar. 28, 2014, pp. 8881-8890.
Zhang, et al., "Anticancer activity and mechanism of juglone on human cervical carcinoma HeLa cells", Canadian Journal of Physiology and Pharmacology, vol. 90, No. 11, Nov. 2012, pp. 1553-1558.
National Center for Biotechnology Information, PubChem Database, Gold thioglucose, CID=6104, http://pubchem.ncbi.nlm.nih.gov/compound/Gold-thioglucose, 2005.
Mirabelli et al., "Correlation of the in vitro cytotoxic and in vivo antitumor activities of Gold(I) Coordination Complexes", Journal of Medicinal Chemistry, 1986, 29(2), pp. 218-223.
Ictidomys Tridecemlineatus Predicted: Spermophilus tridecemlineatus thymine-DNA lycosylase (Tdg), mRNA: NCBI Reference Sequence: XM_005322345. 1; Aug. 21, 2013.
Mohan et al. (2007) Molecular and Cellular Biology 27(1): 229-243.
Mohan et al., Mus. Musculus thymine DNA glycosylate (tdg), Transcript Variant 1, mRNA: NCBI Reference Sequence: NM_011561:1, Sep. 3, 2007.

* cited by examiner

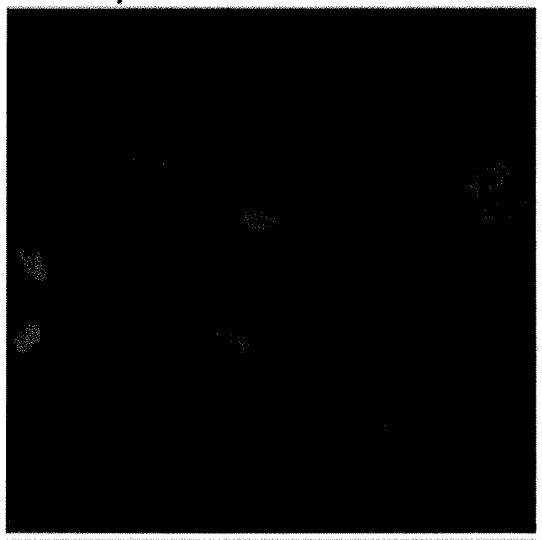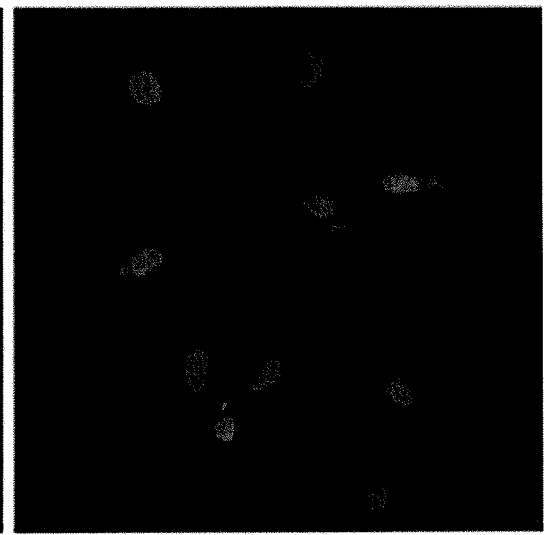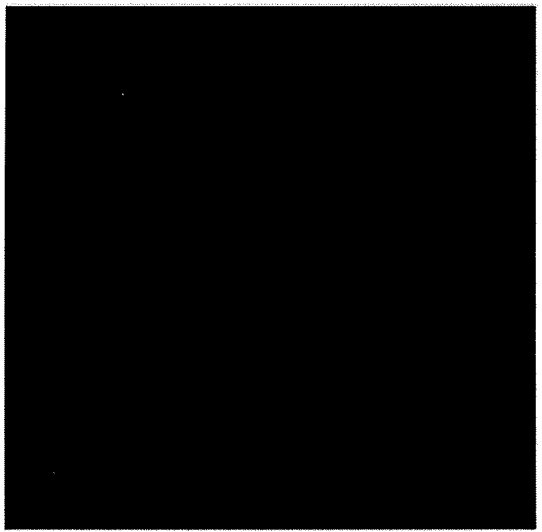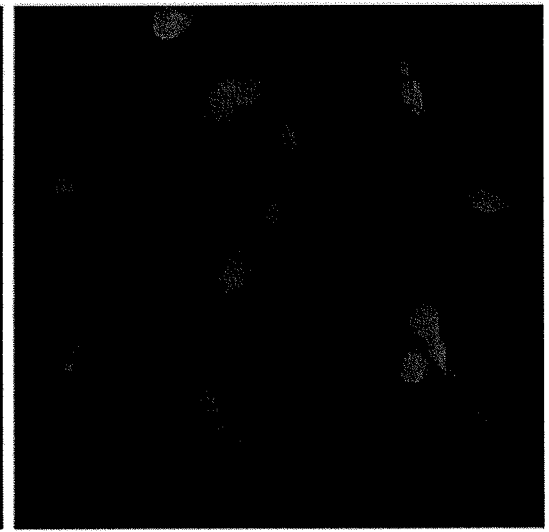
Figure 4

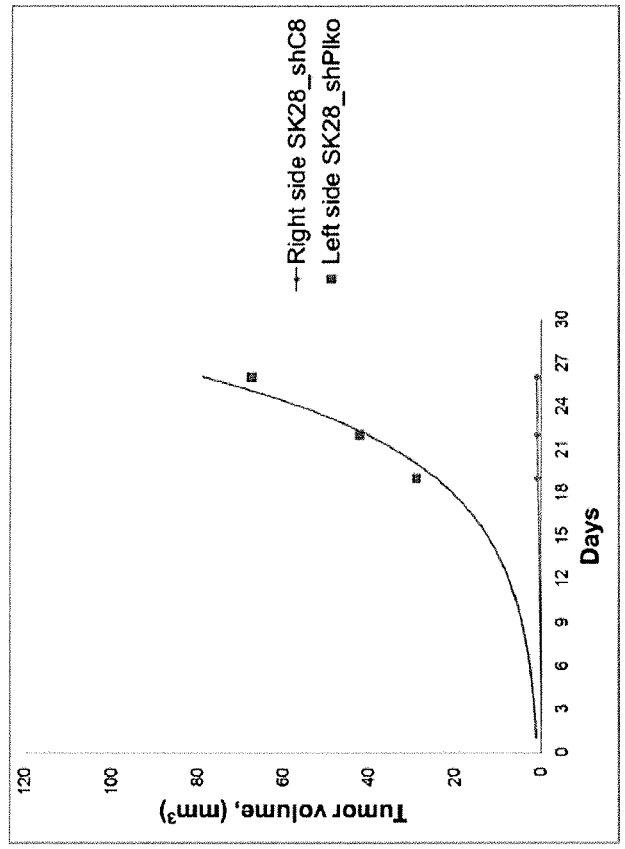
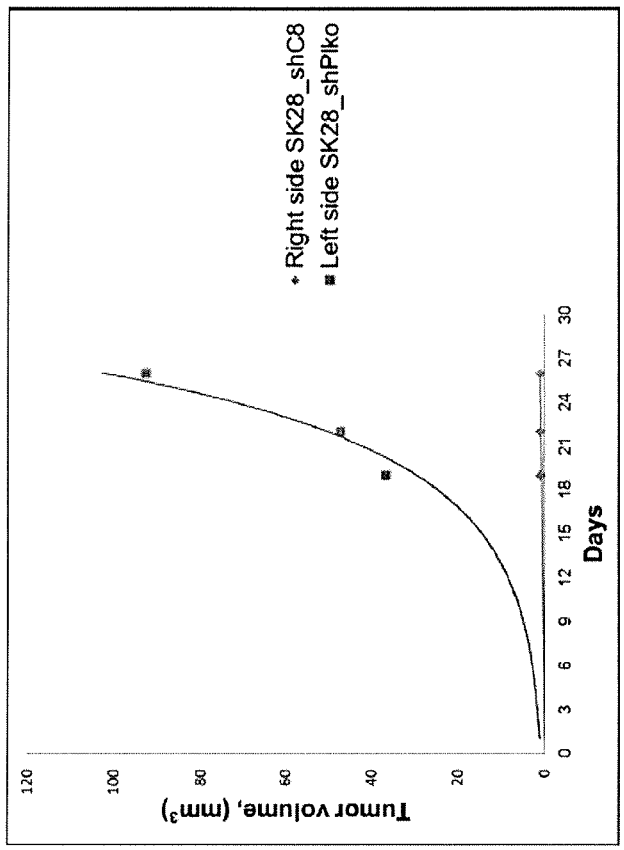
Figure 18
Downregulation of TDG in SK28 cells reduces melanoma growth in a xenograft model

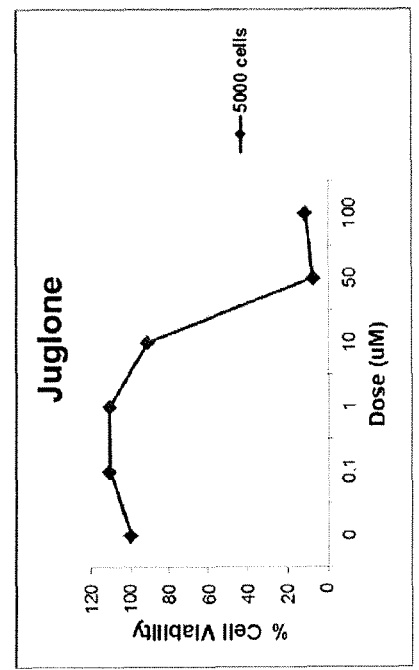
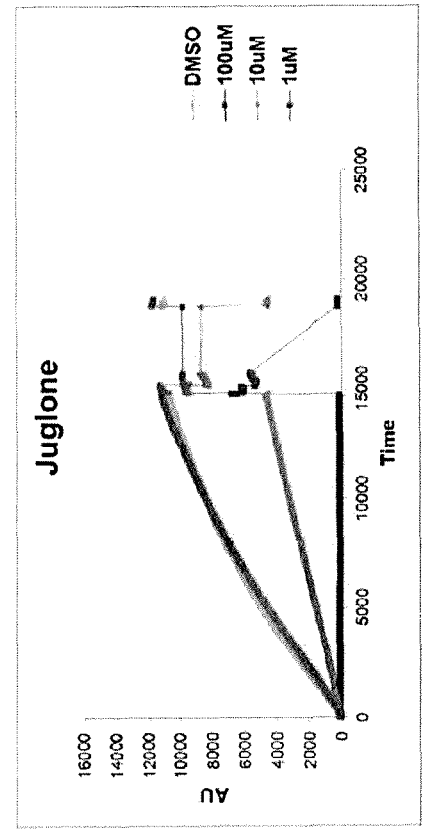
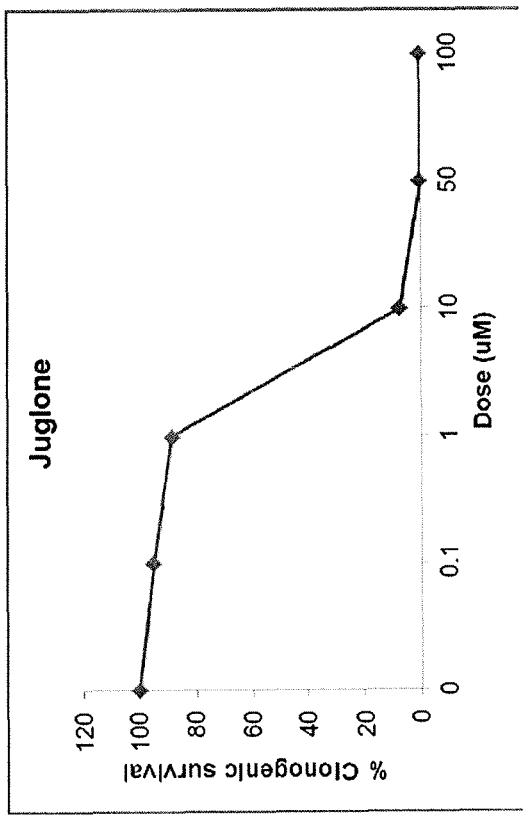
Figure 24

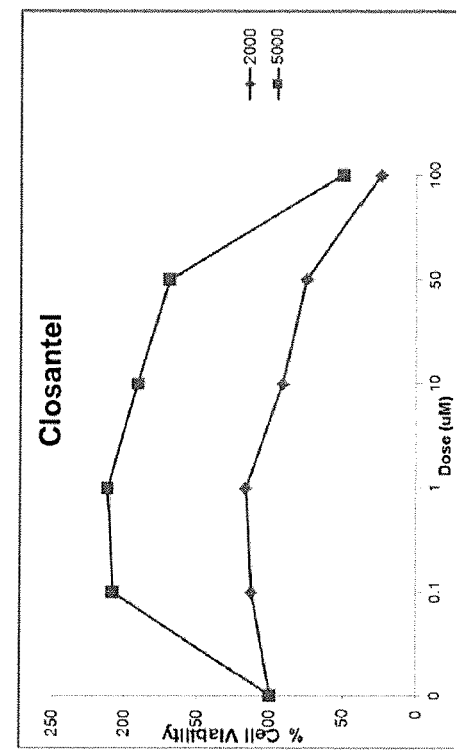
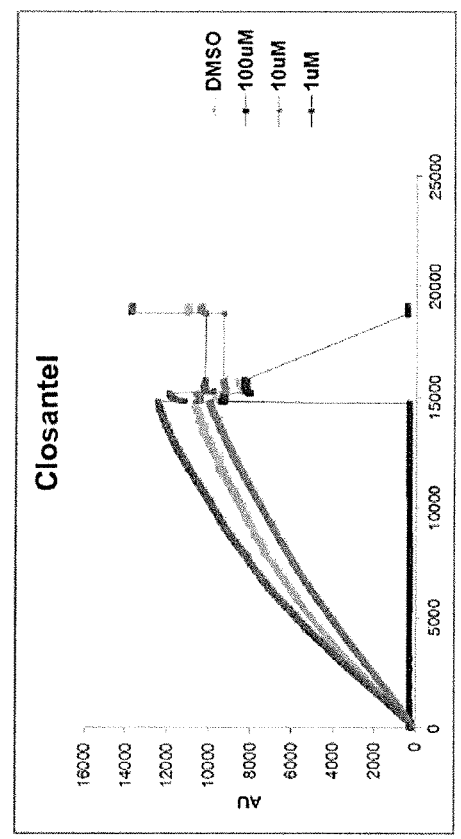
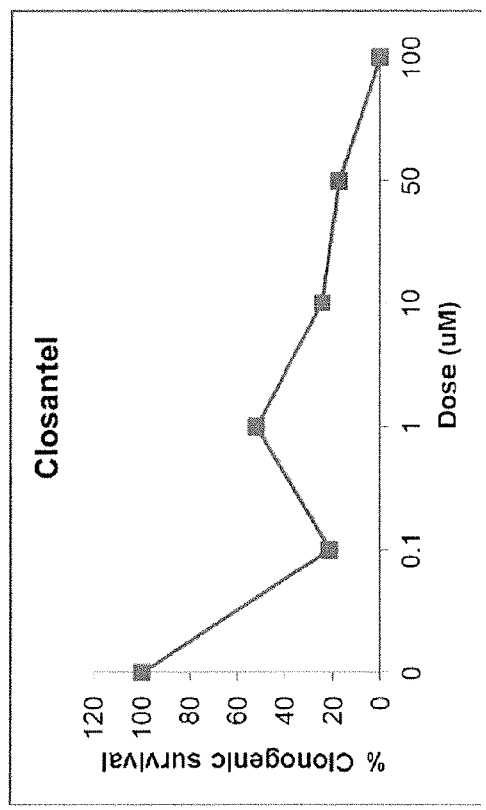
Figure 25

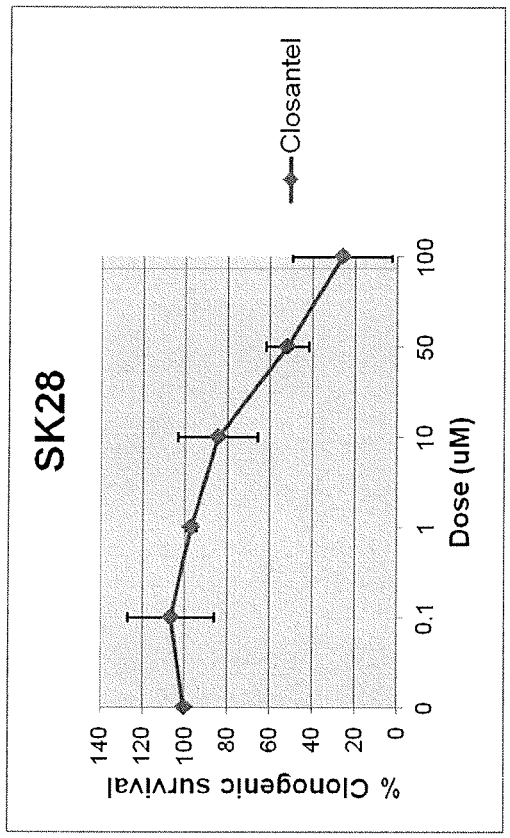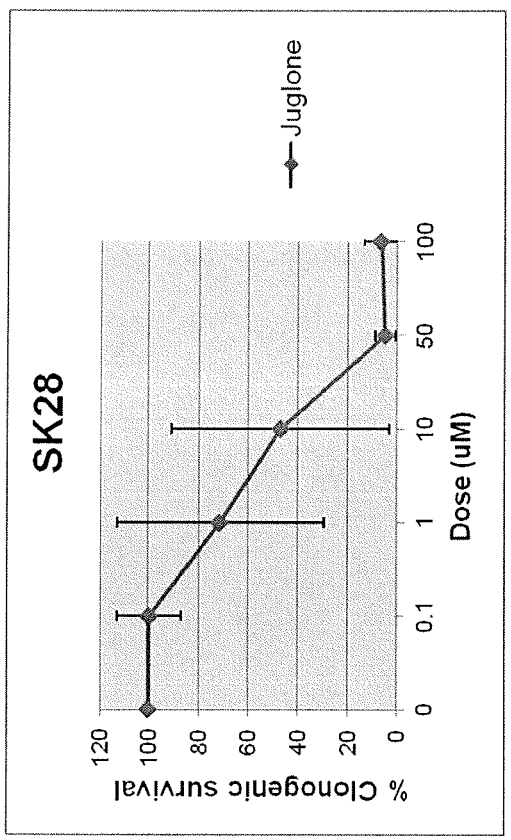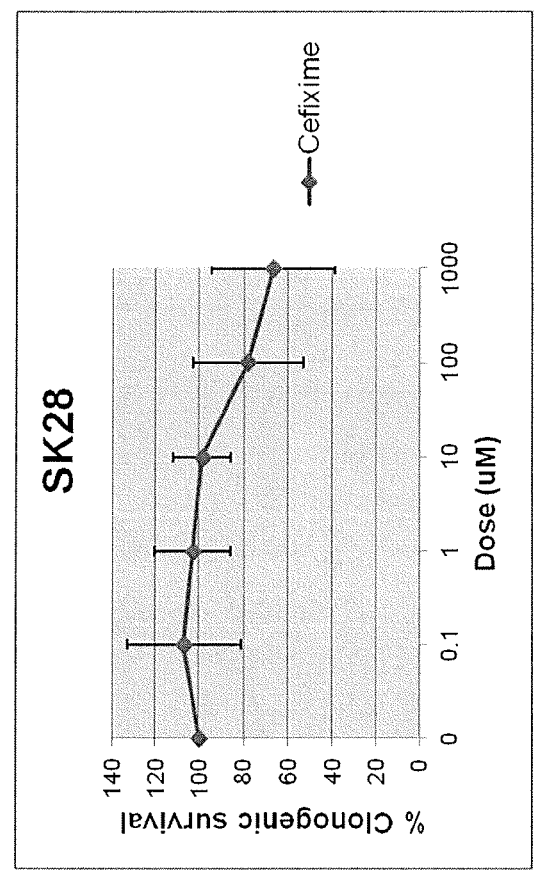
Figure 26

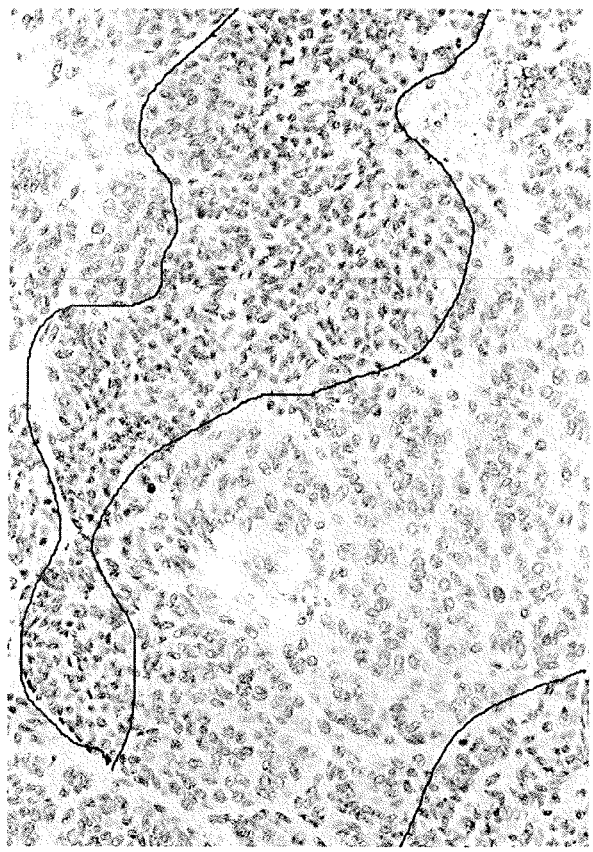
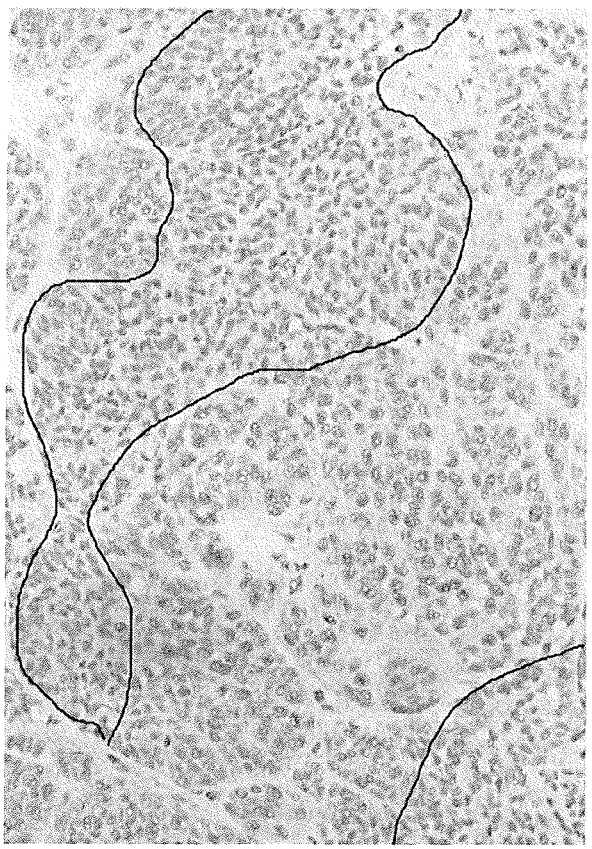
Figure 46

SEQUENCE LISTING

```
<160> NUMBER OF SEQ ID NOS: 8

<210> SEQ ID NO 1
<211> LENGTH: 21
<212> TYPE: DNA
<213> ORGANISM: Homo sapiens

<400> SEQUENCE: 1
gccacgaata gcggtgttta a                                            21

<210> SEQ ID NO 2
<211> LENGTH: 21
<212> TYPE: RNA
<213> ORGANISM: Homo sapiens

<400> SEQUENCE: 2
gccacgaaua gcguguuua a                                             21

<210> SEQ ID NO 3
<211> LENGTH: 58
<212> TYPE: DNA
<213> ORGANISM: Homo sapiens

<400> SEQUENCE: 3
ccgggccacg aatagcggtg tttaactcga gttaaacacc gctattcgtg gcttttttg   58

<210> SEQ ID NO 4
<211> LENGTH: 58
<212> TYPE: RNA
<213> ORGANISM: Homo sapiens

<400> SEQUENCE: 4
ccgggccacg aauagcggug uuuaacucga guuaaacacc gcuauucgug gcuuuuug    58

<210> SEQ ID NO 5
<211> LENGTH: 21
<212> TYPE: DNA
<213> ORGANISM: Homo sapiens

<400> SEQUENCE: 5
gccacgaata gcagtgttta a                                            21

<210> SEQ ID NO 6
<211> LENGTH: 21
<212> TYPE: RNA
<213> ORGANISM: Homo sapiens

<400> SEQUENCE: 6
gccacgaaua gcaguguuua a                                            21

<210> SEQ ID NO 7
<211> LENGTH: 3251
<212> TYPE: DNA
<213> ORGANISM: Homo sapiens
```

<400> SEQUENCE: 7

| | | | | | |
|---|---|---|---|---|---|
| gatttggctc | cgaggaggcg | gaagtgcagc | acagaaaggg | ggtccgtggg | ggacggtaga | 60 |
| agcctggagg | aggagcttga | gtccagccac | tgtctgggta | ctgccagcca | tcgggcccag | 120 |
| gtctctgggg | ttgtcttacc | gcagtgagta | ccacgcggta | ctacagagac | cggctgcccg | 180 |
| tgtgcccggc | aggtggagcc | gcccgcatca | gcggcctcgg | ggaatggaag | cggagaacgc | 240 |
| gggcagctat | tcccttcagc | aagctcaagc | tttttatacg | tttccatttc | aacaactgat | 300 |
| ggctgaagct | cctaatatgg | cagttgtgaa | tgaacagcaa | atgccagaag | aagttccagc | 360 |
| cccagctcct | gctcaggaac | cagtgcaaga | ggctccaaaa | ggaagaaaaa | gaaaacccag | 420 |
| aacaacagaa | ccaaaacaac | cagtggaacc | caaaaaacct | gttgagtcaa | aaaaatctgg | 480 |
| caagtctgca | aaatcaaaag | aaaaacaaga | aaaaattaca | gacacattta | aagtaaaaag | 540 |
| aaaagtagac | cgttttaatg | gtgtttcaga | agctgaactt | ctgaccaaga | ctctccccga | 600 |
| tattttgacc | ttcaatctgg | acattgtcat | tattggcata | aacccgggac | taatggctgc | 660 |
| ttacaaaggg | catcattacc | ctggacctgg | aaaccatttt | tggaagtgtt | tgtttatgtc | 720 |
| agggctcagt | gaggtccagc | tgaaccatat | ggatgatcac | actctaccag | ggaagtatgg | 780 |
| tattggattt | accaacatgg | tggaaaggac | cacgcccggc | agcaaagatc | tctccagtaa | 840 |
| agaatttcgt | gaaggaggac | gtattctagt | acagaaatta | cagaaatatc | agccacgaat | 900 |
| agcagtgttt | aatggaaaat | gtatttatga | aattttttagt | aaagaagttt | ttggagtaaa | 960 |
| ggttaagaac | ttggaatttg | gcttcagcc | ccataagatt | ccagcacag | aaactctctg | 1020 |
| ctatgttatg | ccatcatcca | gtgcaagatg | tgctcagttt | cctcgagccc | aagacaaagt | 1080 |
| tcattactac | ataaaactga | aggacttaag | agatcagttg | aaaggcattg | aacgaaatat | 1140 |
| ggacgttcaa | gaggtgcaat | atacatttga | cctacagctt | gcccaagagg | atgcaaagaa | 1200 |
| gatggctgtt | aaggaagaaa | aatatgatcc | aggttatgag | gcagcatatg | gtggtgctta | 1260 |
| cggagaaaat | ccatgcagca | gtgaaccttg | tggcttctct | tcaaatgggc | taattgagag | 1320 |
| cgtggagtta | agaggagaat | cagctttcag | tggcattcct | aatgggcagt | ggatgaccca | 1380 |
| gtcatttaca | gaccaaattc | cttcctttag | taatcactgt | ggaacacaag | aacaggaaga | 1440 |
| agaaagccat | gcttaagaat | ggtgcttctc | agctctgctt | aaatgctgca | gttttaatgc | 1500 |
| agttgtcaac | aagtagaacc | tcagtttgct | aactgaagtg | ttttattagt | attttactct | 1560 |
| agtggtgtaa | ttgtaatgta | gaacagttgt | gtggtagtgt | gaaccgtatg | aacctaagta | 1620 |
| gtttggaaga | aaaagtaggg | ttttttgtata | ctagcttttg | tatttgaatt | aattatcatt | 1680 |
| ccagcttttt | atatactata | tttcatttat | gaagaaattg | attttctttt | gggagtcact | 1740 |
| tttaatctgt | aattttaaaa | tacaagtctg | aatatttata | gttgattctt | aactgcataa | 1800 |
| acctagatat | accattatcc | cttttatacc | taagaagggc | atgctaataa | ttaccactgt | 1860 |
| caaagaggca | aagtgttga | tttttgtata | tgaagttaag | cctcagtgga | gtctcatttg | 1920 |
| ttagttttta | gtggtaacta | agggtaaact | cagggttccc | tgagctatat | gcacactcag | 1980 |
| acctctttgc | tttaccagtg | gtgtttgtga | gttgctcagt | agtaaaaact | ggcccttacc | 2040 |
| tgacagagcc | ctggctttga | cctgctcagc | cctgtgtgtt | aatcctctag | tagccaatta | 2100 |
| actactctgg | ggtggcaggt | tccagagaat | gcagtagacc | ttttgccact | catctgtgtt | 2160 |
| ttacttgaga | catgtaaata | tgatagggaa | ggaactgaat | ttctccattc | atatttataa | 2220 |
| ccattctagt | tttatcttcc | ttggctttaa | gagtgtgcca | tggaaagtga | taagaaatga | 2280 |

-continued

```
acttctaggc taagcaaaaa gatgctggag atatttgata ctctcattta aactggtgct    2340
ttatgtacat gagatgtact aaaataagta atatagaatt tttcttgcta ggtaaatcca    2400
gtaagccaat aattttaaag attctttatc tgcatcattg ctgtttgtta ctataaatta    2460
aatgaacctc atggaaaggt tgaggtgtat acctttgtga ttttctaatg agtttttccat   2520 ggtgctacaa ataatccaga ctaccaggtc tggtagatat taaagctggg tactaagaaa    2580
tgttatttgc atcctctcag ttactcctga atattctgat ttcatacgta cccagggagc    2640
atgctgtttt gtcaatcaat ataaaatatt tatgaggtct cccccacccc caggaggtta    2700
tatgattgct cttctcttta taataagaga aacaaattct tattgtgaat cttaacatgc    2760
tttttagctg tggctatgat ggattttatt ttttcctagg tcaagctgtg taaaagtcat    2820
ttatgttatt taaatgatgt actgtactgc tgtttacatg gacgttttgt gcgggtgctt    2880
tgaagtgcct tgcatcaggg attaggagca attaaattat ttttcacgg gactgtgtaa     2940 agcatgtaac taggtattgc tttggtatat aactattgta gctttacaag agattgtttt    3000
atttgaatgg ggaaaatacc ctttaaatta tgacggacat ccactagaga tgggtttgag    3060
gattttccaa gcgtgtaata atgatgtttt tcctaacatg acagatgagt agtaaatgtt    3120
gatatatcct atacatgaca gtgtgagact ttttcattaa ataatattga aagatttaa     3180 aattcatttg aaagtctgat ggcttttaca ataaaagata ttaagaattg ttatccttaa    3240
cttaaaaaaa a                                                         3251
```

<210> SEQ ID NO 8
<211> LENGTH: 33
<212> TYPE: PRT
<213> ORGANISM: Salmo salar

<400> SEQUENCE: 8

```
Met Pro Arg Arg Arg Arg Ser Ser Ser Arg Pro Val Arg Arg Arg Arg
1               5                   10                  15

Arg Pro Arg Val Ser Arg Arg Arg Arg Arg Gly Gly Arg Arg Arg
            20                  25                  30

Arg
```

INHIBITION OF THYMINE DNA GLYCOSYLASE IN THE TREATMENT OF CANCER

CROSS REFERENCE TO RELATED APPLICATIONS

This application is a continuation of U.S. application Ser. No. 15/084,680, filed on Mar. 30, 2016, which is a continuation of International Application No. PCT/US14/58240, filed on Sep. 30, 2014, which claims priority to U.S. Provisional Application No. 61/884,478, filed on Sep. 30, 2013, the contents of which are incorporated herein by reference herein in their entireties.

STATEMENT OF GOVERNMENT SUPPORT

The inventions described herein were made, in part, with funds obtained from the National Cancer Institute, Grant No. CA078412. The U.S. government may have certain rights in these inventions.

REFERENCE TO A SEQUENCE LISTING

This application includes a Sequence Listing submitted electronically as a text file named TDG Inhibitors ST25.txt, created on Sep. 10, 2014, with a size of 5898 bytes. The Sequence Listing is incorporated by reference herein.

FIELD OF THE INVENTION

The invention relates generally to the field of cancer treatment. More particularly, the invention relates to inhibiting the expression or biologic activity of thymine DNA glycosylase (TDG) in cancer cells s such as melanoma cells, lung cancer cells, prostate cancer cells, colon cancer cells, recto-sigmoid colon cancer cells, pancreatic cancer cells, ovarian cancer cells, and breast cancer cells and, thereby reducing proliferation and/or cell growth and/or inducing differentiation and/or inducing senescence of the cancer cells.

BACKGROUND OF THE INVENTION

Various publications, including patents, published applications, technical articles and scholarly articles are cited throughout the specification. Each of these cited publications is incorporated by reference herein, in its entirety and for all purposes.

Melanoma is an aggressive cancer that derives from the malignant transformation of melanocytes, the pigment-producing cells that reside in the basal layer of the epidermis in the skin, and in other organs, including the eye and the intestine. Melanomas are caused by genetic and epigenetic alterations in melanocytes affecting MAP kinase pathway (RAS-RAF), PTEN-AKT axis, p16INK4 (regulation of senescence), and MITF. Although targeted therapy, e.g. using RAF inhibitors, has improved the clinical management of melanoma for fifty percent of the patients for a limited period (6 months), an effective treatment of melanoma is still lacking for the entire population and for a longer period of time.

SUMMARY OF THE INVENTION

The invention features methods for inhibiting the growth of premalignant or cancer cells in which TDG is expressed, methods for inducing differentiation of premalignant or cancer cells in which thymine DNA glycosylase (TDG) is expressed, and methods for inducing senescence in premalignant or cancer cells in which TDG is expressed. In general, the methods comprise inhibiting the expression or inhibiting the biologic activity of TDG in the premalignant or cancer cell. In some aspects, inhibiting the expression or the biologic activity of TDG in the premalignant or cancer cell inhibits the growth of the premalignant cell or cancer cell. In some aspects, inhibiting the expression or the biologic activity of TDG in the premalignant or cancer cell induces differentiation of the cancer cell or premalignant cell. In some aspects, inhibiting the expression or the biologic activity of TDG in the premalignant or cancer cell inhibits the growth of the cancer cell or premalignant cell and induces differentiation of the cancer cell or premalignant cell. In some aspects, inhibiting the expression or the biologic activity of TDG in the premalignant cell or cancer cell induces senescence in the cancer cell or premalignant cell. The premalignant or cancer cell may express a high level, an intermediate level, or a low level of thymine DNA glycosylase. Differentiation may comprise reversion of the cancer cell from a cancerous phenotype to a healthy phenotype. This reversion may include or otherwise be characterized, at least in part, by morphologic changes in the cell. The morphologic changes may include the loss of a spindle shape, and/or the acquisition of cellular processes emanating from the cell body. The morphologic changes may comprise characteristic of the morphology of a melanocyte, an oligodendrocyte, a neuron, or an astrocyte. The cancer cell may be any cancer cell in which TDG is expressed or in which TDG is a factor in the transformation of a healthy cell to a cancerous state or in which TDG is a factor in the progression of cancer. The cancer cell may be a melanoma cell, colon cancer cell, recto-sigmoid colon cancer cell, prostate cancer cell, pancreatic cancer cell, ovarian cancer cell, breast cancer cell, lung cancer cell, or brain cancer cell such as a glioblastoma cell. The premalignant cell may be a skin cell that may progress to a melanoma cell, a colon cell that may progress to a colon cancer cell, a rectal cell that may progress to a recto-sigmoid colon cancer cell, a prostate gland cell that may progress to a prostate cancer cell, an ovary cell that may progress to an ovarian cancer cell, a pancreas cell that may progress to a pancreatic cancer cell, a breast cell that may progress to a breast cancer cell, a lung cell that may progress to a lung cancer cell, or a brain cell that may progress to a brain cancer cell such as a glioblastoma cell.

The invention also features methods for treating cancer in a subject in need thereof. The cancer preferably is a cancer in which TDG is expressed. The methods generally comprise administering to a subject having a cancer an effective amount of an agent that inhibits the expression of TDG or an effective amount of an agent that inhibits biologic activity of TDG. Administration may comprise localized or direct administration to the cancer, or may comprise systemic administration, for example, to the blood of the patient. The subject may be any animal, and preferably is a human being. Non-limiting examples of cancer that may be treated according to this method comprise melanoma, colon cancer, recto-sigmoid colon cancer, prostate cancer, ovarian cancer, pancreatic cancer, breast cancer, lung cancer, and brain cancer, including glioblastoma.

Inhibiting the expression of thymine DNA glycosylase may comprise transfecting the cancer cell with a nucleic acid molecule that interferes with the expression of thymine DNA glycosylase. The nucleic acid molecule may comprise or encode a shRNA that specifically hybridizes under stringent conditions to mRNA encoding thymine DNA glycosylase. The nucleic acid molecule may comprise or encode a shRNA that specifically hybridizes under stringent conditions to mRNA encoding human thymine DNA glycosylase. The shRNA may comprise the nucleic acid sequence of SEQ ID NO: 3 or SEQ ID NO: 4, and/or may specifically hybridize to the nucleic acid of SEQ ID NO: 1, SEQ ID NO: 2, SEQ ID NO: 5, or SEQ ID NO: 6, or the complement thereof. Transfecting the cancer cell may comprise infecting the cell with a virus encoding the nucleic acid molecule that interferes with the expression of thymine DNA glycosylase. The virus preferably is a lentivirus.

Inhibiting biologic activity of TDG may comprise contacting a tumor cell with an effective amount of an agent that inhibits the biologic activity of TDG, for example, via administration of the agent to a subject. The agent may comprise an organic or inorganic chemical (including a composition comprising such an organic or inorganic chemical, including a small molecule, and a carrier such as a pharmaceutically acceptable carrier) that inhibits the biologic activity of TDG. The agent may comprise a biomolecule, including an antibody that specifically binds to TDG, or a polypeptide. The agent may comprise one or more of 6-keto-prostaglandin F1a, prostaglandin A1, E6 berbamine, juglone, GW-5074, rottlerin, cefixime, idarubicin, doxorubicin, methenamine, Congo red, sodium ferric gluconate, ferrous sulfate, aurothioglucose, Evans blue, closantel, cinchonine sulfate, hexadimethrine bromide, indigotindisulfonate, and protamine chloride, or any combination thereof. In some preferred aspects, the agent comprises juglone. In some preferred aspects, the agent comprises cefixime. In some preferred aspects, the agent comprises closantel. The tumor cell may comprise a melanoma cell, colon cancer cell, recto-sigmoid colon cancer cell, prostate cancer cell, breast cancer cell, pancreatic cancer cell, ovarian cancer cell, lung cancer cell, or brain cancer cell.

In some aspects, any method may further comprise contacting the m tumor cell with an effective amount of one or more of a RAD51 inhibitor, a DNA alkylating agent, temozolomide, dacarbazine, cisplatin, vincristine, or any combination thereof, for example, via administration to a subject.

The invention also features kits. The kits may comprise an agent that inhibits the expression of TDG, and/or an agent that inhibits biologic activity of TDG, and instructions for using the agent in a method for treating cancer, or in a method for inhibiting the growth of cancer cells, or in a method for inducing differentiation of cancer cells, or in a method for inducing senescence in cancer cells. Such methods may be any methods described or exemplified herein.

The TDG expression-inhibiting agent may comprise or encode shRNA that specifically hybridizes under stringent conditions to mRNA encoding thymine DNA glycosylase. The shRNA may comprise the nucleic acid sequence of SEQ ID NO: 3 or SEQ ID NO: 4, and/or may specifically hybridize to the nucleic acid of SEQ ID NO: 1, SEQ ID NO: 2, SEQ ID NO: 5, or SEQ ID NO: 6, or the complement thereof, or to the nucleic acid sequence corresponding to nucleotides 892-912 of SEQ ID NO: 7, or the complement thereof. The TDG expression-inhibiting agent may comprise a virus encoding the shRNA. The virus preferably is a lentivirus. The TDG biologic activity-inhibiting agent may comprise 6-keto-prostaglandin F1a, prostaglandin A1, E6 berbamine, juglone, GW-5074, rottlerin, cefixime, idarubicin, doxorubicin, methenamine, Congo red, sodium ferric gluconate, ferrous sulfate, aurothioglucose, Evans blue, closantel, cinchonine sulfate, hexadimethrine bromide, indigotindisulfonate, protamine chloride, or any combination thereof. Juglone, closantel, and cefixime are preferred. The agent may be comprised in a composition with a carrier such as a pharmaceutically acceptable carrier.

Use of one or more of 6-keto-prostaglandin F1a, prostaglandin A1, E6 berbamine, juglone, GW-5074, rottlerin, cefixime, idarubicin, doxorubicin, methenamine, Congo red, sodium ferric gluconate, ferrous sulfate, aurothioglucose, Evans blue, closantel, cinchonine sulfate, hexadimethrine bromide, indigotindisulfonate, or protamine chloride, or any combination thereof in the treatment of cancer is further provided. Use of one or more of 6-keto-prostaglandin F1a, prostaglandin A1, E6 berbamine, juglone, GW-5074, rottlerin, cefixime, idarubicin, doxorubicin, methenamine, Congo red, sodium ferric gluconate, ferrous sulfate, aurothioglucose, Evans blue, closantel, cinchonine sulfate, hexadimethrine bromide, indigotindisulfonate, or protamine chloride, or any combination thereof in the treatment of melanoma, colon cancer, recto-sigmoid colon cancer, prostate cancer, breast cancer, ovarian cancer, pancreatic cancer, lung cancer, and/or brain cancer, including glioblastoma, is further provided.

BRIEF DESCRIPTION OF THE DRAWINGS

FIG. 4 shows expression of Tuj1 (stained spindle shapes), a differentiated neuron-specific cell marker, in parental (right panels) and shC8 Mel501 (left panels). Nuclei were stained with DAPI.

FIG. 18 shows that TDG downregulation inhibits the tumorigenic potential of SK28 melanoma cells. Growth curves refer to two SCID mice injected with pLKO vector-infected (left flank) or shTDG C8-infected (right flank) SK28 cells.

FIG. 24 shows inhibition of TDG glycosylase activity in vitro by juglone, and reduction of SK28 cell viability (MTS assay) and colony-forming ability (clonogenic assay) upon treatment with juglone.

FIG. 25 shows inhibition of TDG glycosylase activity in vitro by closantel, and reduction of SK28 cell viability (MTS assay) and colony-forming ability (clonogenic assay) upon treatment with closantel.

FIG. 26 shows a reduction of clonogenic capacity of SK28 MEL melanoma cells by juglone, closantel, and cefixime.

FIG. 46 shows immunohistochemistry detection of TDG expression and 5caC expression levels.

DETAILED DESCRIPTION OF THE INVENTION

Figure 1:
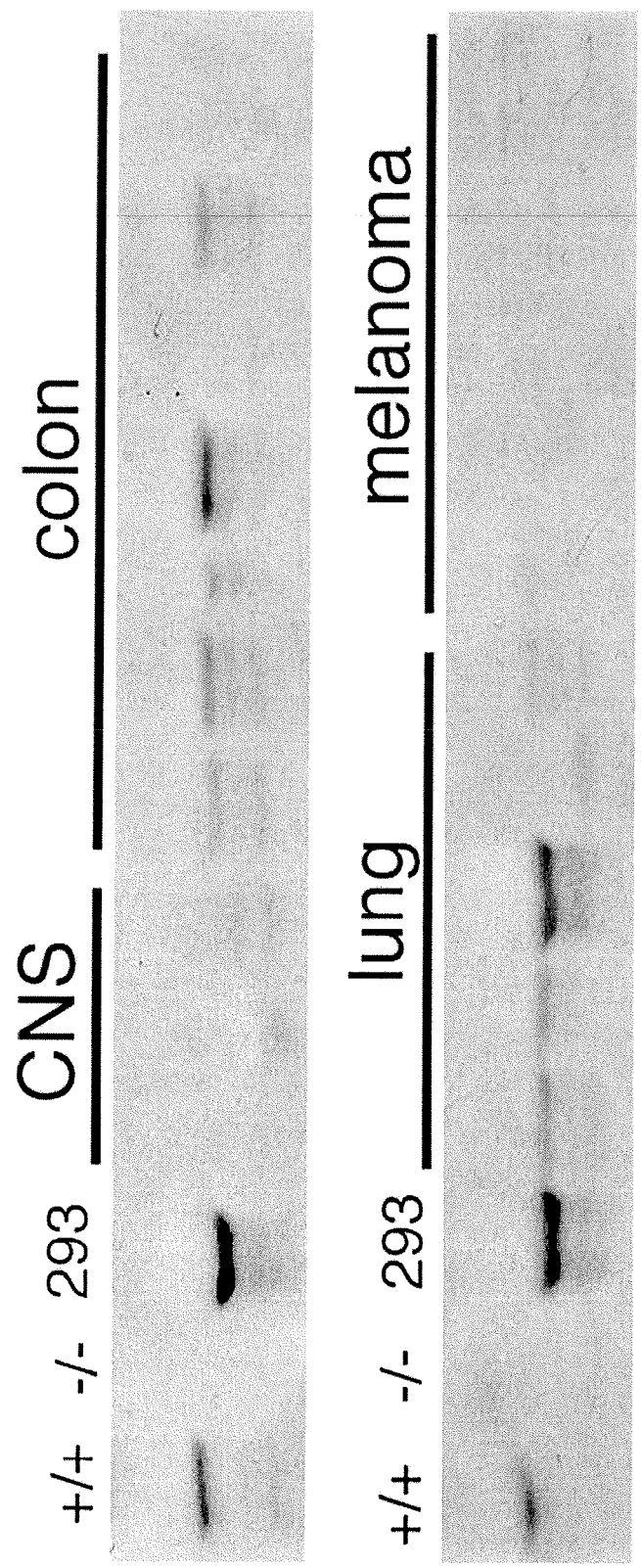
FIG. 1 shows a Western blot analysis of TDG in a portion of a panel of 60 cancer cell lines. +/+ and −/− are the positive and negative control lysates from wild type and Tdg-null mouse embryo fibroblasts (MEFs). 293 is an additional positive control.

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

Knockdown includes the reduced expression of a gene. A knockdown typically has at least about a 20% reduction in expression, preferably has at least about a 50% reduction in expression, and more preferably has at least about a 75% reduction in expression, and in some aspects has at least about an 80% to about an 85% reduction in expression, at least about an 85% to about a 90% reduction in expression, or about an 80% to about a 90% reduction in expression, and in some aspects has a greater than 90% reduction in expression, or a greater than 95% reduction in expression.

Transforming or transfecting a cell includes the introduction of exogenous or heterologous nucleic acid molecules into the cell. Cells may be stably or transiently transformed or transfected.

Nucleic acid molecules include any chain of at least two nucleotides, which may be unmodified or modified RNA or DNA, hybrids of RNA and DNA, and may be single, double, or triple stranded.

Expression of a nucleic acid molecule comprises the biosynthesis of a gene product. Expression includes the transcription of a gene into RNA, the translation of RNA into a protein or polypeptide, and all naturally occurring post-transcriptional and post-translational modifications thereof.

Inhibiting includes reducing, decreasing, blocking, preventing, delaying, inactivating, desensitizing, stopping, knocking down (e.g., knockdown), and/or downregulating the biologic activity or expression of a gene, molecule or pathway of interest or cell growth or proliferation.

It has been observed in accordance with the invention that inhibition of the DNA base excision repair enzyme thymine DNA glycosylase (TDG) arrests the growth of cancer cells, including melanoma cells and prostate cancer cells, and induces differentiation and/or senescence of cancer cells, including melanoma cells and prostate cancer as characterized by morphologic changes and phenotypes characteristic of non-cancerous cells. The inhibition of TDG produced similar results in melanoma cells that express high and intermediate levels of TDG. It was also observed that inhibition of TDG in melanoma cells, colon cancer cells, recto-sigmoid colon cancer cells, prostate cancer cells, breast cancer cells, ovarian cancer cells, pancreatic cancer cells, lung cancer cells, and/or brain cancer cells, including glioblastoma cells inhibits proliferation of such cells. These observations indicate TDG may be targeted in in various types of cancers.

For melanoma, it appeared that some melanoma cells that express low levels of TDG have tumor forming ability when injected into recipient mice in xenotransplantation experiments. It was initially believed that reducing the levels of TDG in melanoma cells that carry high or intermediate levels of TDG expression, would increase their tumor forming ability. Surprisingly, reducing levels of TDG in melanoma cells with relatively normal or intermediate expression of TDG resulted in a significant inhibition of cell growth and the differentiation of such cells toward a reversion to a healthy, non-cancerous phenotype and morphology.

Accordingly, the invention features methods for inhibiting the growth and/or proliferation of cancer cells in which TDG is expressed, and/or for inducing differentiation of TDG-expressing cells into non-cancerous cells, and/or for inducing senescence in TDG-expressing cells. In general, the methods comprise inhibiting the expression or biologic activity of TDG in the cells. Any of the methods of the invention may be carried out in vivo, ex vivo, in vitro, or in situ.

The invention also features compositions for inhibiting the growth and/or proliferation of premalignant and/or cancer cells, and/or for inducing differentiation of premalignant and/or cancer cells into non-cancerous cells or healthy cells, and/or for inducing senescence in premalignant and/or cancer cells. Such compositions comprise any of 6-keto-prostaglandin F1a, prostaglandin A1, E6 berbamine, juglone, GW-5074, rottlerin, cefixime, idarubicin, doxorubicin, methenamine, Congo red, sodium ferric gluconate, ferrous sulfate, aurothioglucose, Evans blue, closantel, cinchonine sulfate, hexadimethrine bromide, indigotindisulfonate, protamine chloride (e.g., SEQ ID NO: 8), or any pharmaceutically acceptable salt thereof, or any combination thereof. The compositions comprise a carrier such as a pharmaceutically acceptable carrier. The amount of the agent in the composition may be an amount effective to inhibit the growth and/or proliferation of cancer cells, and/or to induce differentiation of into non-cancerous cells, and/or to induce senescence in the cells. The amount of the agent may be tailored to the particular cancer, or to premalignant versus cancerous cells. The particular cancer (or premalignant state thereof) cells may comprise melanoma cells, colon cancer cells, recto-sigmoid colon cancer cells, prostate cancer cells, pancreatic cancer cells, ovarian cancer cells, breast cancer cells, lung cancer cells, and/or brain cancer cells, including glioblastoma cells.

Inhibiting the expression of TDG may comprise transfecting the cancer or premalignant cell with a nucleic acid molecule that interferes with the expression of TDG in the cell. For example, nucleic acid-based interference with TDG expression may take advantage of RNA interference.

RNA interference (RNAi) is a mechanism of post-transcriptional gene silencing mediated by double-stranded RNA (dsRNA), which is distinct from antisense and ribozyme-based approaches. RNA interference may be effectuated, for example, by administering a nucleic acid (e.g., dsRNA) that hybridizes under stringent conditions to the gene encoding thymine DNA glycosylase (including mRNA encoding thymine DNA glycosylase), thereby attenuating its expression. RNA interference provides shRNA or siRNA that comprise multiple sequences that target one or more regions of the target gene. dsRNA molecules (shRNA or siRNA) are believed to direct sequence-specific degradation of mRNA in cells of various types after first undergoing processing by an RNase III-like enzyme called DICER into smaller dsRNA molecules comprised of two 21 nucleotide (nt) strands, each of which has a 5' phosphate group and a 3' hydroxyl, and includes a 19 nt region precisely complementary with the other strand, so that there is a 19 nt duplex region flanked by 2 nt-3' overhangs. RNAi is thus mediated by short interfering RNAs (siRNA), which typically comprise a double-stranded region approximately 19 nucleotides in length with 1-2 nucleotide 3' overhangs on each strand, resulting in a total length of between approximately 21 and 23 nucleotides. In mammalian cells, dsRNA longer than approximately 30 nucleotides typically induces nonspecific mRNA degradation via the interferon response. However, the presence of siRNA in mammalian cells, rather than inducing the interferon response, results in sequence-specific gene silencing.

Viral vectors or DNA vectors encode short hairpin RNA (shRNA) which are processed in the cell cytoplasm to short interfering RNA (siRNA). In general, a short, interfering RNA (siRNA) comprises an RNA duplex that is preferably approximately 19 basepairs long and optionally further comprises one or two single-stranded overhangs or loops. A siRNA may comprise two RNA strands hybridized together, or may alternatively comprise a single RNA strand that includes a self-hybridizing portion. siRNAs may include one or more free strand ends, which may include phosphate and/or hydroxyl groups. siRNAs typically include a portion that hybridizes under stringent conditions with a target transcript. One strand of the siRNA (or, the self-hybridizing portion of the siRNA) is typically precisely complementary with a region of the target transcript (e.g., thymine DNA glycosylase transcript), meaning that the siRNA hybridizes to the target transcript without a single mismatch. In aspects in which perfect complementarity is not achieved, it is generally preferred that any mismatches be located at or near the siRNA termini.

siRNAs have been shown to downregulate gene expression when transferred into mammalian cells by such methods as transfection, electroporation, cationic liposome-mediated transfection, or microinjection, or when expressed in cells via any of a variety of plasmid-based approaches. The siRNA may comprise two individual nucleic acid strands or of a single strand with a self-complementary region capable of forming a hairpin (stem-loop) structure. A number of variations in structure, length, number of mismatches, size of loop, identity of nucleotides in overhangs, etc., are consistent with effective siRNA-triggered gene silencing. While not wishing to be bound by any theory, it is believed that intracellular processing (e.g., by DICER) of a variety of different precursors results in production of siRNA capable of effectively mediating gene silencing. Generally, it is preferred to target exons rather than introns, and it may also be preferable to select sequences complementary to regions within the 3' portion of the target transcript. Generally it is preferred to select sequences that contain an approximately equimolar ratio of the different nucleotides and to avoid stretches in which a single residue is repeated multiple times.

siRNAs may thus comprise RNA molecules having a double-stranded region approximately 19 nucleotides in length with 1-2 nucleotide 3' overhangs on each strand, resulting in a total length of between approximately 21 and 23 nucleotides. siRNAs also include various RNA structures that may be processed in vivo to generate such molecules. Such structures include RNA strands containing two complementary elements that hybridize to one another to form a stem, a loop, and optionally an overhang, preferably a 3' overhang. Preferably, the stem is approximately 19 bp long, the loop is about 1-20, more preferably about 4-10, and most preferably about 6-8 nt long and/or the overhang is about 1-20, and more preferably about 2-15 nt long. In certain aspects, the stem is minimally 19 nucleotides in length and may be up to approximately 29 nucleotides in length. Loops of 4 nucleotides or greater are less likely subject to steric constraints than are shorter loops and therefore may be preferred. The overhang may include a 5' phosphate and a 3' hydroxyl. The overhang may, but need not comprise a plurality of U residues, e.g., between 1 and 5 U residues. Classical siRNAs as described above trigger degradation of mRNAs to which they are targeted, thereby also reducing the rate of protein synthesis. In addition to siRNAs that act via the classical pathway, certain siRNAs that bind to the 3' UTR of a template transcript may inhibit expression of a protein encoded by the template transcript by a mechanism related to but distinct from classic RNA interference, e.g., by reducing translation of the transcript rather than decreasing its stability. Such RNAs are referred to as microRNAs (miRNAs) and are typically between approximately 20 and 26 nucleotides in length, e.g., 22 nt in length. It is believed that they are derived from larger precursors known as small temporal RNAs (stRNAs) or mRNA precursors, which are typically approximately 70 nt long with an approximately 4-15 nt loop. Endogenous RNAs of this type have been identified in a number of organisms including mammals, suggesting that this mechanism of post-transcriptional gene silencing may be widespread. MicroRNAs have been shown to block translation of target transcripts containing target sites.

siRNAs such as naturally occurring or artificial (i.e., designed by humans) mRNAs that bind within the 3' UTR (or elsewhere in a target transcript) and inhibit translation may tolerate a larger number of mismatches in the siRNA/template duplex, and particularly may tolerate mismatches within the central region of the duplex. In fact, there is evidence that some mismatches may be desirable or required as naturally occurring stRNAs frequently exhibit such mismatches as do mRNAs that have been shown to inhibit translation in vitro. For example, when hybridized with the target transcript such siRNAs frequently include two stretches of perfect complementarity separated by a region of mismatch. A variety of structures are possible. For example, the mRNA may include multiple areas of nonidentity (mismatch). The areas of nonidentity (mismatch) need not be symmetrical in the sense that both the target (e.g., thymine DNA glycosylase) and the mRNA include non-paired nucleotides. Typically the stretches of perfect complementarity are at least 5 nucleotides in length, e.g., 6, 7, or more nucleotides in length, while the regions of mismatch may be, for example, 1, 2, 3, or 4 nucleotides in length.

Hairpin structures designed to mimic siRNAs and mRNA precursors are processed intracellularly into molecules capable of reducing or inhibiting expression of target transcripts (e.g., thymine DNA glycosylase). These hairpin structures, which are based on classical siRNAs consisting of two RNA strands forming a 19 bp duplex structure are classified as class I or class II hairpins. Class I hairpins incorporate a loop at the 5' or 3' end of the antisense siRNA strand (i.e., the strand complementary to the target transcript whose inhibition is desired) but are otherwise identical to classical siRNAs. Class II hairpins resemble mRNA precursors in that they include a 19 nt duplex region and a loop at either the 3' or 5' end of the antisense strand of the duplex in addition to one or more nucleotide mismatches in the stem. These molecules are processed intracellularly into small RNA duplex structures capable of mediating silencing. They appear to exert their effects through degradation of the target mRNA rather than through translational repression as is thought to be the case for naturally occurring mRNAs and stRNAs.

Thus, a diverse set of RNA molecules containing duplex structures is able to mediate silencing through various mechanisms. Any such RNA, one portion of which binds to a target transcript (e.g., thymine DNA glycosylase) and reduces its expression, whether by triggering degradation, by inhibiting translation, or by other means, may be considered an siRNA, and any structure that generates such an siRNA (i.e., serves as a precursor to the RNA) is useful.

A further method of RNA interference is the use of short hairpin RNAs (shRNA). A plasmid containing a DNA sequence encoding for a particular desired siRNA sequence is delivered into a target cell (e.g., melanoma cells, colon cancer cells, recto-sigmoid colon cancer cells, prostate cancer cells, pancreatic cancer cells, ovarian cancer cells, breast cancer cells, lung cancer cells, and/or brain cancer cells, including glioblastoma cells) via transfection or virally-mediated infection. Once in the cell, the DNA sequence is continuously transcribed into RNA molecules that loop back on themselves and form hairpin structures through intramolecular base pairing. These hairpin structures, once processed by the cell, are equivalent to transfected siRNA molecules and are used by the cell to mediate RNAi of the desired protein. The use of shRNA has an advantage over siRNA transfection as the former can lead to stable, long-term inhibition of protein expression. Inhibition of protein expression by transfected siRNAs is a transient phenomenon that does not occur for times periods longer than several days. In some cases, though, this may be preferable and desired. In cases where longer periods of protein inhibition are necessary, shRNA mediated inhibition is preferable. The use of shRNA is preferred for some aspects of the invention. Typically, siRNA-encoding vectors are constructs comprising a promoter, a sequence of the target gene to be silenced in the sense orientation, a spacer, the antisense of the target gene sequence, and a terminator.

Inhibition of the expression of thymine DNA glycosylase can also be effectuated by other means that are known and readily practiced in the art. For example, antisense nucleic acids can be used. Antisense RNA transcripts have a base sequence complementary to part or all of any other RNA transcript in the same cell. Such transcripts modulate gene expression through a variety of mechanisms including the modulation of RNA splicing, the modulation of RNA transport and the modulation of the translation of mRNA. Accordingly, in certain aspects, inhibition of the expression of thymine DNA glycosylase in a cancer cell can be accomplished by expressing an antisense nucleic acid molecule in the cancer cell. The cancer cell may comprise one or more of melanoma cells, colon cancer cells, recto-sigmoid colon cancer cells, prostate cancer cells, pancreatic cancer cells, ovarian cancer cells, breast cancer cells, lung cancer cells, and/or brain cancer cells, including glioblastoma cells.

Antisense nucleic acids are generally single-stranded nucleic acids (DNA, RNA, modified DNA, or modified RNA) complementary to a portion of a target nucleic acid (e.g., an mRNA transcript) and therefore able to bind to the target to form a duplex. Typically, they are oligonucleotides that range from 15 to 35 nucleotides in length but may range from 10 up to approximately 50 nucleotides in length. Binding typically reduces or inhibits the expression of the target nucleic acid, such as the gene encoding the target signal protein. For example, antisense oligonucleotides may block transcription when bound to genomic DNA, inhibit translation when bound to mRNA, and/or lead to degradation of the nucleic acid. Inhibition of the expression of thymine DNA glycosylase can be achieved by the administration of antisense nucleic acids comprising sequences complementary to those of the mRNA that encodes thymine DNA glycosylase.

Antisense oligonucleotides can be synthesized with a base sequence that is complementary to a portion of any RNA transcript in the cancer cell. Antisense oligonucleotides can modulate gene expression through a variety of mechanisms including the modulation of RNA splicing, the modulation of RNA transport and the modulation of the translation of mRNA. Various properties of antisense oligonucleotides including stability, toxicity, tissue distribution, and cellular uptake and binding affinity may be altered through chemical modifications including (i) replacement of the phosphodiester backbone (e.g., peptide nucleic acid, phosphorothioate oligonucleotides, and phosphoramidate oligonucleotides), (ii) modification of the sugar base (e.g., 2'-O-propylribose and 2'-methoxyethoxyribose), and (iii) modification of the nucleoside (e.g., C-5 propynyl U, C-5 thiazole U, and phenoxazine C).

Inhibition of thymine DNA glycosylase can also be effectuated by use of ribozymes. Certain nucleic acid molecules referred to as ribozymes or deoxyribozymes have been shown to catalyze the sequence-specific cleavage of RNA molecules. The cleavage site is determined by complementary pairing of nucleotides in the RNA or DNA enzyme with nucleotides in the target RNA. Thus, RNA and DNA enzymes can be designed to cleave to any RNA molecule, thereby increasing its rate of degradation.

In some aspects, the cancer cells can be specifically transformed with transcription-silencing nucleic acids such as shRNA or siRNA, or can be transformed with vectors encoding such nucleic acids such that the cell expresses the inhibitory nucleic acid molecules. Transfection of the cancer cells can be carried out according to any means suitable in the art.

A cancer cell can be transfected with such nucleic acid molecules according to any means available in the art such as those described or exemplified herein. It is preferred that the cancer cells are stably transformed with a vector comprising a nucleic acid sequence encoding such regulatory nucleic acid molecules, although transiently transformations are suitable. Any vector suitable for transformation of the particular cell of interest can be used. In preferred embodiments, the vector is a viral vector. In some embodiments, the viral vector is a lentivirus vector.

In some preferred aspects, the nucleic acid molecule is a siRNA that specifically hybridizes under stringent conditions to mRNA encoding thymine DNA glycosylase. In some preferred aspects, the nucleic acid molecule is a shRNA that specifically hybridizes under stringent conditions to mRNA encoding thymine DNA glycosylase. The shRNA may comprise the nucleic acid sequence of SEQ ID NO: 3 or the nucleic acid sequence of SEQ ID NO: 4. The shRNA may hybridize to a nucleic acid encoding thymine DNA glycosylase including the nucleic acid sequence of SEQ ID NO: 1, SEQ ID NO: 2, SEQ ID NO: 5, or SEQ ID NO: 6. Preferably, the thymine DNA glycosylase is human thymine DNA glycosylase (SEQ ID NO: 7).

Inhibiting the biologic activity of TDG may comprise contacting the cell with an effective amount of an agent that inhibits the biologic activity of TDG. The agent may comprise an organic or inorganic chemical (including a composition comprising such an organic or inorganic chemical, including a small molecule, and a carrier such as a pharmaceutically acceptable carrier) that inhibits the biologic activity of TDG. The agent may comprise a biomolecule, including an antibody that specifically binds to TDG, or a polypeptide.

Biologic activity of TDG includes DNA/thymine glycosylase activity and excision repair of thymine and uracil mismatches, including G/T, G/U, C/T, and T/T mismatches, as well as repair of hydroxymethyluracil, formylcytosine and carboxylcytosine opposite G. Biologic activity also includes transcriptional co-activator activity. In some aspects, it may be preferable to selectively inhibit glycosylase activity, for example, while retaining transcriptional co-activator activity.

The agent may comprise one or more of 6-keto-prostaglandin F1a, prostaglandin A1, E6 berbamine, juglone, GW-5074, rottlerin, cefixime, idarubicin, doxorubicin, methenamine, Congo red, sodium ferric gluconate, ferrous sulfate, aurothioglucose, Evans blue, closantel, cinchonine sulfate, hexadimethrine bromide, indigotindisulfonate, and protamine chloride, or any combination thereof. In some preferred aspects, the agent comprises juglone. In some preferred aspects, the agent comprises cefixime. In some preferred aspects, the agent comprises closantel. Protamine may comprise the amino acid sequence of SEQ ID NO: 8. Any of the agents may comprise a pharmaceutically acceptable salt thereof. Any of these agents may be comprised in a composition comprising the agent and a pharmaceutically acceptable carrier. Such compositions are within the scope of the invention.

Pharmaceutically acceptable salts may be acid or base salts. Non-limiting examples of pharmaceutically acceptable salts include sulfates, methosulfates, methanesulfates, pyrosulfates, bisulfates, sulfites, bisulfites, nitrates, besylates, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, dioates, benzoates, chlorobenzoates, methylbenzoates, dinitromenzoates, hydroxybenzoates, methoxybenzoates, phthalates, sulfonates, toluenesulfonates, xylenesulfonates, pheylacetates, phenylpropionates, phenylbutyrates, citrates, lactates, γ-hydroxybutyrates, glycollates, tartrates, methanesulfonates, propanesulfonates, mandelates, and other salts customarily used or otherwise FDA-approved.

The inhibition of the expression or biologic activity of TDG may synergize with other agents for an enhanced cancer-treating effect. Thus, in some aspects, the method may further comprise contacting the cancer cell with one or more of a RAD51 inhibitor, a DNA alkylating agent, temozolomide, dacarbazine, cisplatin, vincristine, or any combination thereof. The cancer cell may comprise melanoma cells, colon cancer cells, recto-sigmoid colon cancer cells, prostate cancer cells, pancreatic cancer cells, ovarian cancer cells, breast cancer cells, lung cancer cells, and/or brain cancer cells, including glioblastoma cells.

In some aspects, the level of 5-carboxylcytosine may serve as a biomarker for efficacy of TDG inhibition. Preferably, elevated levels of 5-carboxylcytosine indicate that TDG inhibition has occurred. Thus, the methods may optionally comprise, after inhibiting the expression or biologic activity of TDG, detecting the level of 5-carboxylcytosine in the cell, and if the level of 5-carboxylcytosine is not elevated, contacting the cell with a modulated, preferably increased, amount of the agent or with a different agent. These detecting and contacting steps may be repeated any number of times sufficient in order to alter the dosing of the agent, or at least to determine whether TDG inhibition has occurred. 5-carboxylcytosine levels reflecting TDG inhibition preferably are elevated over a baseline. The baseline preferably relates back to a level of 5-carboxylcytosine in a cancer cell in which TDG has not been inhibited, or in which TDG has been inhibited at a low or insufficient level. The agent is preferably the same agent initially contacted to the cells, but in some aspects, the agent is a different agent. For example, if it is determined that the level of 5-carboxylcytosine is not elevated, it may indicate that the first agent has not inhibited the expression or biologic activity of TDG such that a different agent may be used.

Inhibiting the expression or biologic activity of TDG may cause the cancer cell to arrest growth in either the S phase of the cell cycle, or at the G2/M DNA damage checkpoint. It is preferred in some aspects that this arrest is sustained, such that the cell no longer grows. Sustenance at either such point of the cell cycle may be maintained until the cell dies, enters senescence, or differentiates into a non-malignant cell.

The invention also features methods for treating a cancer comprising cells that express thymine DNA glycosylase, whether at high, intermediate, or low levels of expression, in a subject in need thereof. Subjects include, without limitation, mammals such as farm animals (e.g., horse, cow, sheep, pig), laboratory animals (e.g., mouse, rat, rabbit), companion animals (e.g., dog, cat), or non-human primates (e.g., new world monkey and old world monkey). In preferred aspects, the subject is a human being. In general, the methods comprise inhibiting the expression or inhibiting the biologic activity of TDG in the tumor, for example, by administering to the subject an effective amount of an agent that inhibits the expression of TDG and/or an agent that inhibits the biologic activity of TDG. The cancer/tumor cells may comprise melanoma cells, colon cancer cells, recto-sigmoid colon cancer cells, prostate cancer cells, pancreatic cancer cells, ovarian cancer cells, breast cancer cells, lung cancer cells, and/or brain cancer cells, including glioblastoma cells Administration may be directly to the tumor or indirectly to the tumor, for example, by administering the agent to the blood and allowing the agent to reach the tumor through the blood flow. The administration may comprise active targeting of the agent to the tumor. The agent may be administered systemically, or may be administered proximally or locally to the tumor.

Inhibiting the expression of TDG may comprise transfecting a tumor cell in which TDG is expressed with a nucleic acid molecule that interferes with the expression of TDG, including an RNA interference nucleic acid molecule. Such transfection occurs following administration of the nucleic acid molecule to the subject. In some aspects, the nucleic acid molecule is a siRNA that specifically hybridizes under stringent conditions to mRNA encoding TDG. In some preferred aspects, the nucleic acid molecule is a shRNA that specifically hybridizes under stringent conditions to mRNA encoding thymine DNA glycosylase. The shRNA may comprise the nucleic acid sequence of SEQ ID NO: 3 or the nucleic acid sequence of SEQ ID NO: 4. The shRNA may hybridize to a nucleic acid encoding thymine DNA glycosylase including the nucleic acid sequence of SEQ ID NO: 1, SEQ ID NO: 2, SEQ ID NO: 5, or SEQ ID NO: 6. Preferably, the thymine DNA glycosylase is human thymine DNA glycosylase (SEQ ID NO: 7). Transforming a tumor cell may comprise infecting the tumor cell with a virus or other suitable delivery vehicle encoding the RNA interference nucleic acid molecule. The virus may comprise a lentivirus.

Inhibiting the biologic activity of TDG may comprise contacting a tumor cell in which TDG is expressed with an effective amount of an agent that inhibits the biologic activity of TDG. Such contacting occurs following administration of the agent to the subject. The agent may comprise an organic or inorganic chemical (including a composition comprising such an organic or inorganic chemical, including a small molecule, and a carrier such as a pharmaceutically acceptable carrier) that inhibits the biologic activity of TDG. The agent may comprise a biomolecule, including an antibody that specifically binds to TDG, or a polypeptide. The agent may comprise one or more of 6-keto-prostaglandin F1a, prostaglandin A1, E6 berbamine, juglone, GW-5074, rottlerin, cefixime, idarubicin, doxorubicin, methenamine, Congo red, sodium ferric gluconate, ferrous sulfate, aurothioglucose, Evans blue, closantel, cinchonine sulfate, hexadimethrine bromide, indigotindisulfonate, and protamine chloride, or any combination thereof. In some preferred aspects, the agent comprises juglone. In some preferred aspects, the agent comprises cefixime. In some preferred aspects, the agent comprises closantel.

Biologic activity of TDG includes DNA/thymine glycosylase activity and excision repair of thymine and uracil mismatches, including G/T, G/U, C/T, and T/T mismatches, as well as repair of hydroxymethyluracil, formylcytosine and carboxylcytosine opposite G. Biologic activity also includes transcriptional co-activator and transcriptional co-repressor activity. In some aspects, it may be preferable to selectively inhibit glycosylase activity, for example, while retaining transcriptional co-activator and transcriptional co-repressor activity, in the subject.

In some aspects, the method may further comprise administering to the subject an effective amount of one or more of a RAD51 inhibitor, a DNA alkylating agent, temozolomide, dacarbazine, cisplatin, vincristine, or any combination thereof. Administration of any such agents or combination may be prior to, substantially at the same time as, or following administering to the subject an effective amount of an agent that inhibits the expression of TDG and/or an agent that inhibits the biologic activity of TDG.

In some aspects, the methods may optionally comprise detecting the level of 5-carboxylcytosine in a sample of tumor tissue obtained from the subject, for example, after administering the TDG expression- or biologic activity-inhibiting agent and/or the RAD51 inhibitor, a DNA alkylating agent, temozolomide, dacarbazine, cisplatin, and/or vincristine, and if the level of 5-carboxylcytosine is not elevated in the sample, administering to the subject a modulated, preferably increased, amount of the TDG expression- or biologic activity-inhibiting agent or administering to the subject a different TDG expression- or biologic activity-inhibiting agent. Thus, for example, monitoring 5-carboxylcytosine levels in the subject's tumor may serve as a way to monitor treatment efficacy and make adjustments to the treatment schedule in order to optimize treatment in the subject. Sampling of patient tumors and assessment of 5-carboxylcytosine levels may take place as frequently or infrequently as appropriate for guiding melanoma treatment in the subject. The tumor may comprise melanoma, colon cancer, recto-sigmoid colon cancer, prostate cancer, pancreatic cancer, ovarian cancer, breast cancer, lung cancer, and/or brain cancer, including glioblastoma.

5-carboxylcytosine elevation is believed to serve as a proxy for effective TDG inhibition and, thus, effective cancer treatment, particularly for melanoma. 5-carboxylcytosine elevation also may be used as a biomarker for certain cancers such as melanoma. Thus, in order to determine whether 5-carboxylcytosine is elevated in a patient's tumors, it may be appropriate to determine a baseline level of 5-carboxylcytosine in the tumor before initiating a TDG inhibition therapeutic regimen. Thus, in some aspects, the methods may optionally comprise detecting the level of 5-carboxylcytosine in a sample of tumor tissue obtained from the subject before administering the TDG expression- or biologic activity-inhibiting agent and/or the RAD51 inhibitor, a DNA alkylating agent, temozolomide, dacarbazine, cisplatin, and/or vincristine. In some alternative aspects, post-TDG inhibitor administration-patient 5-carboxylcytosine levels may be compared against population-derived 5-carboxylcytosine baseline levels, rather than a patient-derived baseline level.

Detection of 5-carboxylcytosine may comprise a cancer diagnostic. For example, a method may comprise isolation of a tissue sample from a subject, and determination of whether 5-carboxylcytosine is expressed, or expressed at elevated levels indicative of a cancerous state may be made. Determination of whether 5-carboxylcytosine is expressed, or expressed at elevated levels in the tissue may indicate that the patient has melanoma. colon cancer, recto-sigmoid colon cancer, prostate cancer, pancreatic cancer, ovarian cancer, breast cancer, lung cancer, and/or brain cancer, including glioblastoma.

The invention also features kits. The kits may be used, for example, to practice any of the methods described or exemplified herein. In some aspects, a kit comprises a nucleic acid molecule that interferes with the expression of thymine DNA glycosylase, and instructions for using the nucleic acid molecule in a method for inhibiting the growth of melanoma cells, and/or for inducing differentiation of cancer or premalignant cells into non-cancerous cells, and/or for inducing senescence in cancer or premalignant cells, and/or for treating cancer in a subject in need thereof. The cancer cells may comprise melanoma cells, colon cancer cells, recto-sigmoid colon cancer cells, prostate cancer cells, pancreatic cancer cells, ovarian cancer cells, breast cancer cells, lung cancer cells, and/or brain cancer cells, including glioblastoma cells. In some aspects, a kit comprises a nucleic acid molecule that interferes with the expression of thymine DNA glycosylase, and instructions for using the nucleic acid molecule in a method for treating cancer such as any method described or exemplified herein. The nucleic acid molecule may be a siRNA and/or a shRNA that specifically hybridizes under stringent conditions to mRNA encoding thymine DNA glycosylase. The shRNA may comprise the nucleic acid sequence of SEQ ID NO: 3 or the nucleic acid sequence of SEQ ID NO: 4. The shRNA may hybridize to a nucleic acid encoding thymine DNA glycosylase including the nucleic acid sequence of SEQ ID NO: 1, SEQ ID NO: 2, SEQ ID NO: 5, or SEQ ID NO: 6. Preferably, the thymine DNA glycosylase is human thymine DNA glycosylase (SEQ ID NO: 7). The non-cancerous cells may comprise one or more of cells comprising a morphology characteristic of melanocytes, oligodendrocytes, astrocytes, or neurons. The non-cancerous cells may comprise one or more of melanocytes, oligodendrocytes, astrocytes, or neurons.

In some aspects, the kit comprises an agent that inhibits biologic activity of thymine DNA glycosylase (TDG) and instructions for using the nucleic acid molecule in a method for inhibiting the growth of cancer or premalignant cells, and/or for inducing differentiation of cancer cells into non-cancerous cells, and/or for inducing senescence in premalignant or cancer cells, and/or for treating cancer in a subject in need thereof. The biologic activity-inhibiting agent may comprise 6-keto-prostaglandin F1a, prostaglandin A1, E6 berbamine, juglone, GW-5074, rottlerin, or any combination thereof. The biologic activity-inhibiting agent may comprise cefixime, idarubicin, doxorubicin, methenamine, Congo red, sodium ferric gluconate, ferrous sulfate, aurothioglucose, Evans blue, closantel, cinchonine sulfate, hexadimethrine bromide, indigotindisulfonate, protamine chloride, or any combination thereof. Juglone, cefixime, and closantel are preferred.

In some aspects, the kit further comprises a RAD51 inhibitor, temozolomide, cisplatin, or vincristine, and instructions for using the RAD51 inhibitor, temozolomide, cisplatin, or vincristine in a synergistically-effective amount with the agent that inhibits the expression of thymine DNA glycosylase or with the agent that inhibits biologic activity of thymine DNA glycosylase in a method for inhibiting the growth of premalignant or cancer cells, and/or for inducing differentiation of cancer cells into non-cancerous cells, and/or for inducing senescence in premalignant or cells, and/or for treating cancer in a subject in need thereof. In some aspects, the kit further comprises instructions for determining the level of 5-carboxylcytosine in a sample obtained from the tumor, and modulating, preferably increasing, the amount of the TDG expression- or biologic activity-inhibiting agent or administering to the subject a different TDG expression- or biologic activity-inhibiting agent, in order to enhance TDG inhibition.

The disclosure also features use of 6-keto-prostaglandin F1a, prostaglandin A1, E6 berbamine, juglone, GW-5074, rottlerin, cefixime, idarubicin, doxorubicin, methenamine, Congo red, sodium ferric gluconate, ferrous sulfate, aurothioglucose, Evans blue, closantel, cinchonine sulfate, hexadimethrine bromide, indigotindisulfonate, or protamine chloride, or a pharmaceutically acceptable salt thereof, or a composition thereof, or any combination thereof in the manufacture of a medicament for the treatment of cancer, including melanoma, lung cancer, breast cancer, colon cancer, recto-sigmoid colon cancer, prostate cancer, pancreatic cancer, ovarian cancer, brain cancer, and/or glioblastoma.

The following examples are provided to describe the invention in greater detail. They are intended to illustrate, not to limit, the invention.

Example 1

Reduced TDG Expression in Melanoma Cells

Because G:T and G:U repair systems are generally effective in protecting cells from spontaneous mutagenesis, it was hypothesized that inactivating mutations of TDG may accelerate the accumulation of these types of mutation in certain cancer genes. In preliminary evaluations, it was observed that TDG expression is frequently reduced or absent in certain cancer cell lines, particularly with respect to melanoma (FIG. 1). From these results, it was hypothesized that reducing the levels of TDG in melanoma cells would increase their tumor forming ability. As the Examples below illustrate, however, reducing TDG levels in melanoma cells not only did not increase their tumor forming ability, it reduced their growth and induced differentiation toward a healthy phenotype.

Example 2

Knockdown of TDG in Melanoma Cells that Express High Levels of TDG

The base excision repair thymine DNA glycosylase (TDG) has a dual role in prevention of mutations that may originate from deamination of 5-methylcytosine and in transcriptional regulation. Based on work on TDG knockout mouse embryos, whose phenotypes suggested an involvement of neural crest cells, the precursors of melanocytes, and the fact that melanoma cell lines were observed to have low levels of TDG proteins, it was hypothesized that modulation of TDG levels may affect the biology of melanoma.

Initial experiments demonstrated that downregulation of TDG levels in Mel501, a melanoma line characterized by high endogenous levels of TDG, caused reduced growth and induced characteristic morphological changes. As explained below, upon shTDG silencing, Mel501 cells lost the typical spindle shape to present higher quantities of cellular processes resembling dendrites, a characteristic of melanocytes, oligodendrocytes, astrocytes, and neurons. Thus, it is believed that downregulation of TDG levels, and perhaps even inhibition of its glycosylase activity, may represent a valuable therapeutic opportunity in a fraction of melanoma cases, exemplified by Mel501 cells, causing growth inhibition and differentiation.

Figure 2:
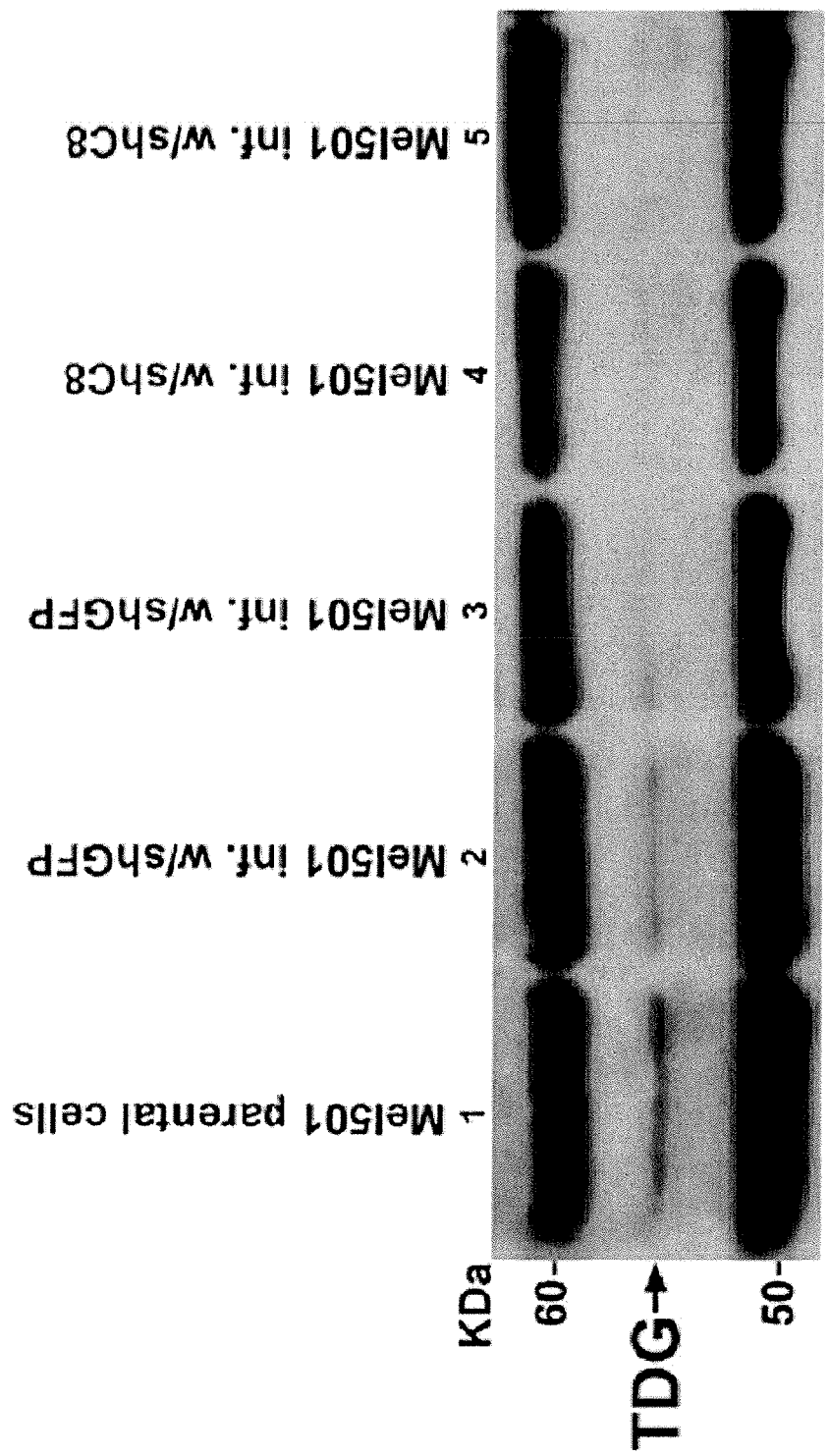
FIG. 2 shows down-regulation of TDG in Mel501 cells.

Mel501 cell lines were infected with a sh lentivirus specific for TDG, named shC8, and in parallel, Mel501 cells were infected with a control lentivirus specific for green fluorescent protein, named shGFP. Stable cell lines expressing each lentivirus were selected using the Puromycin selectable marker. All the experiments were conducted in duplicate and performed twice in order to further validate every result obtained with biological duplicates. After 2 weeks of antibiotic selection, the down-regulation of TDG by lentiviral vector shC8, but not shGFP, was confirmed by Western blot analysis of lysates from parental and infected Mel501 cells (FIG. 2).

Figure 3:
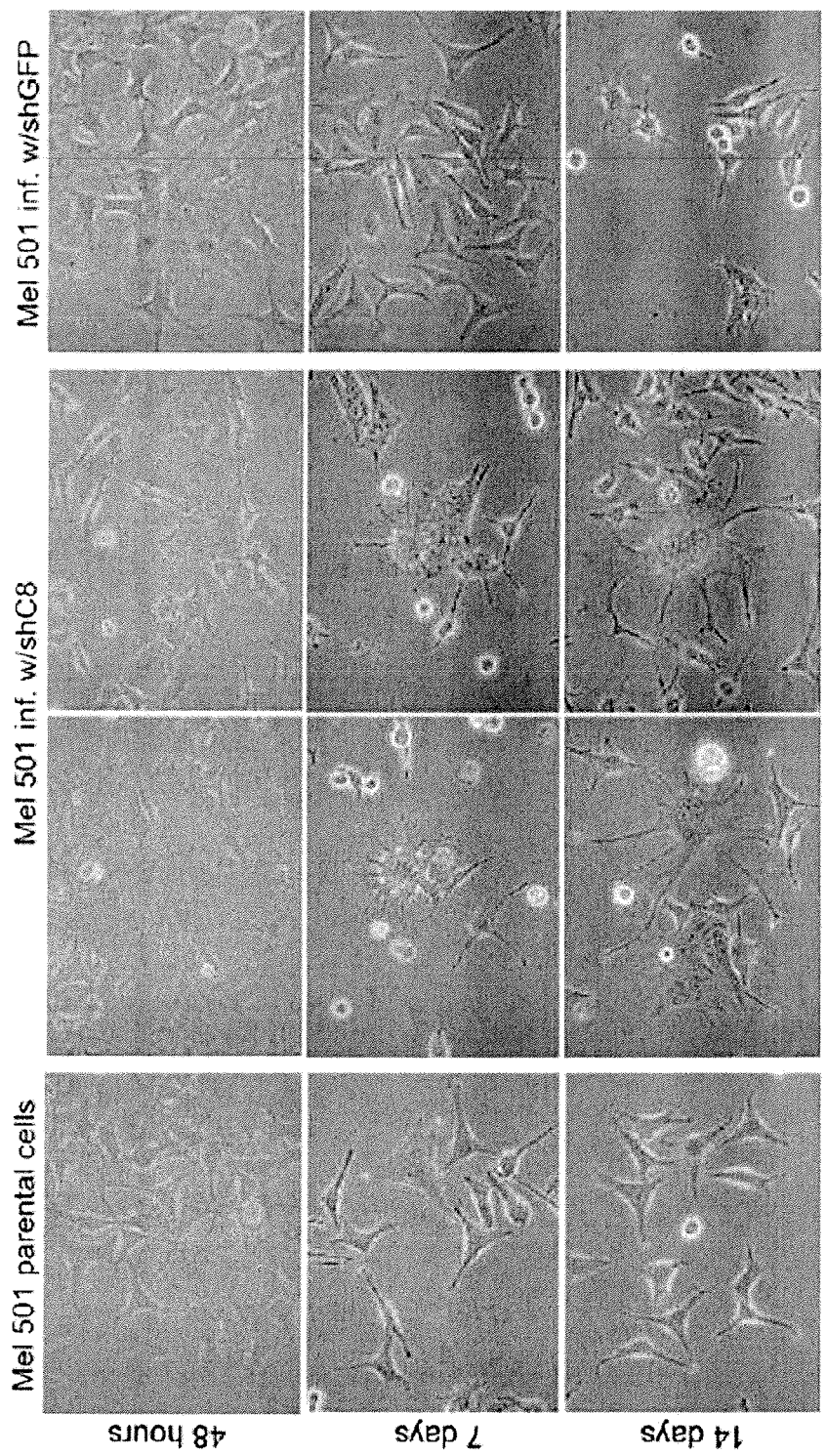
FIG. 3 shows TDG down-regulation induces morphological changes in Mel501 cells.

A significant morphological change was observed in Mel501 cells, which, upon infection with the shC8 lentivirus downregulating TDG, lost the typical spindle shape (FIG. 3, left) and assumed a morphology characteristic of melanocytes, oligodendrocytes, astrocytes, or neurons (FIG. 3, center). This effect was specific for TDG downregulation, because the changes induced by the shGFP control lentivirus were more subtle, though some cells resembling astrocytes were observed upon shGFP infection (FIG. 3, right). Initial evidence of neuronal differentiation was obtained by showing that Mel501 cells with TDG downregulation express the neuronal marker Tuj1 (FIG. 4).

Example 3

Knockdown of TDG in Melanoma Cells that Express Intermediate Levels of TDG

In Example 2 above, the data show that downregulation of TDG levels in Mel501, a melanoma cell line characterized by high endogenous levels of TDG, caused reduced proliferation and induced characteristic morphological changes such as the appearance of dendrites, which are cellular processes characteristic of melanocytes, oligodendrocytes, astrocytes, and neurons. Follow-up experiments were conducted in a second melanoma cell line, which expresses intermediate levels of TDG, or in any event, lower levels of TDG relative to Mel501 cells. These experiments, conducted in MULL cells, showed similar results to those observed as part of the experiments of Example 2.

MULL cells were infected with a sh lentivirus specific for TDG, named shC8, and parallel MULL cell cultures were infected with an empty vector control lentivirus, named shPLKO. Stable cell lines expressing each lentivirus were selected using the Puromycin selectable marker. All of these experiments were conducted in duplicate and performed twice in order to further validate every result obtained with biological duplicates.

Figure 5:
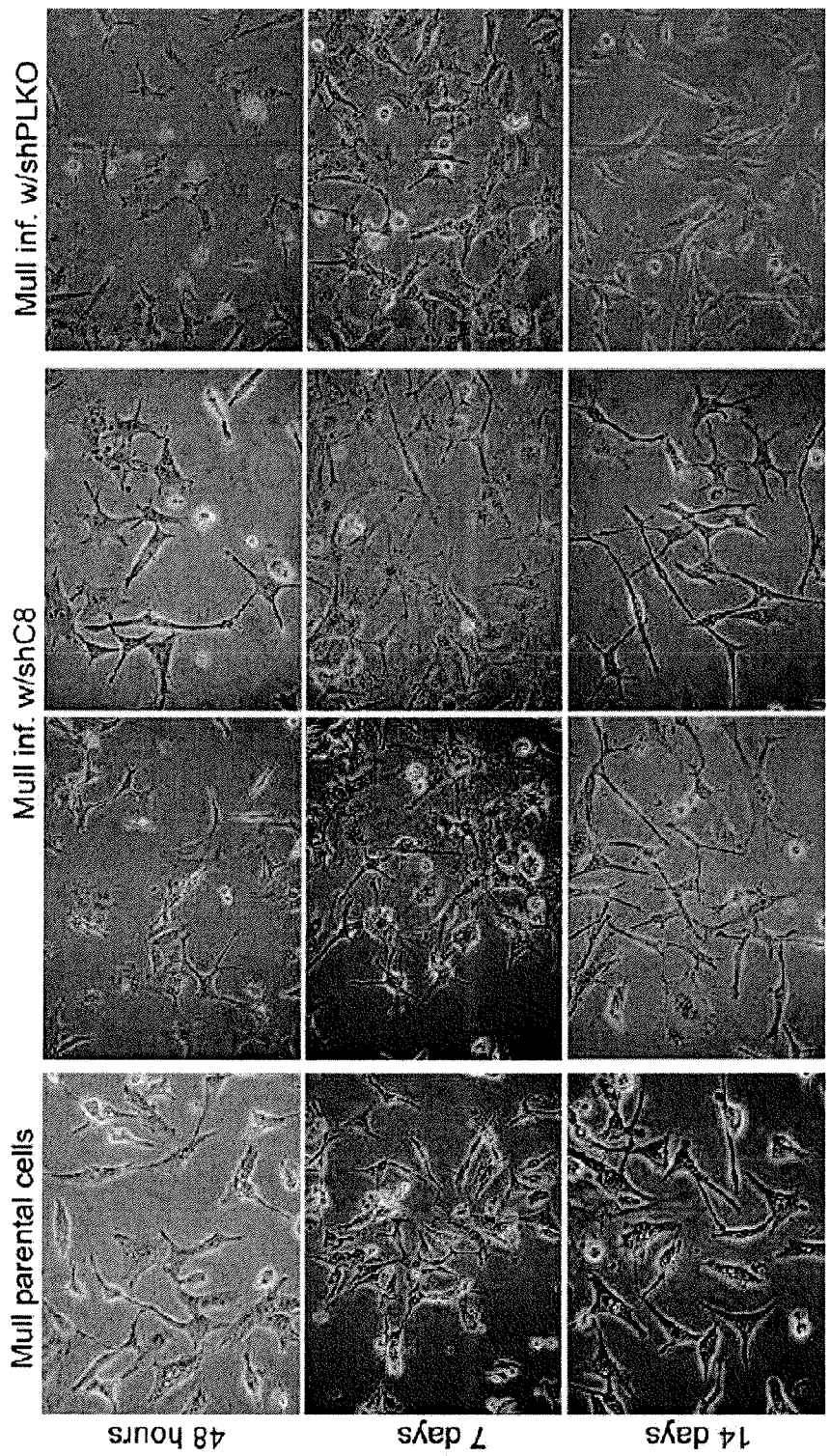
FIG. 5 shows TDG down-regulation induces morphological changes in Mull cells.
Figure 6:
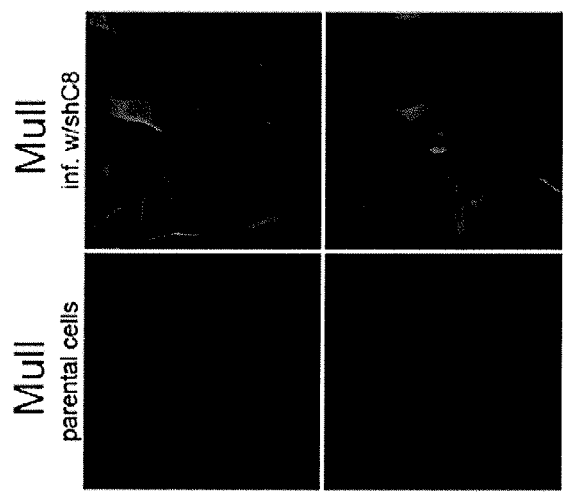
FIG. 6 shows expression of Tuj1 (stained spindle shapes), a differentiated neuron-specific cell marker, in parental (right panels) and shC8 MULL cells (left panels). Nuclei were stained with DAPI.

A significant morphological change was observed in MULL cells upon infection with the shC8 lentivirus downregulating TDG. Specifically, MULL cells lost the typical triangular, elongated, spindle shape (FIG. 5, left), and each developed several dendritic processes, thus acquiring a morphology characteristic of melanocytes, oligodendrocytes, astrocytes or neurons (FIG. 5, center). This effect was specific for TDG downregulation, because the changes induced by the shPLKO control empty lentivirus were more subtle, though some cells resembling astrocytes were observed upon shPLKO infection (FIG. 5, right). Similar to the results observed for experiments in Mel501 cells (Example 2), MULL cells with TDG downregulation showed evidence of neuronal differentiation by expressing the neuronal marker Tuj1 (FIG. 6).

Example 4

Figure 7:
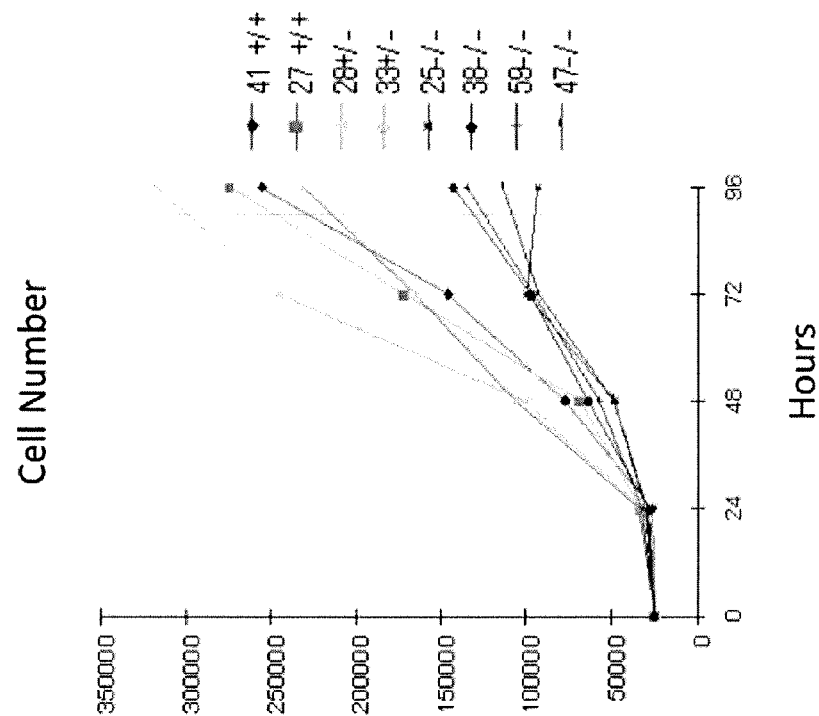
FIG. 7 shows reduced proliferation of TDG knock-out mouse embryo fibroblast lines (MEFs, indicated as −/−), in comparison to wild type and heterozygous MEFs (indicated as +/+ and +/−, respectively).
Figure 8:
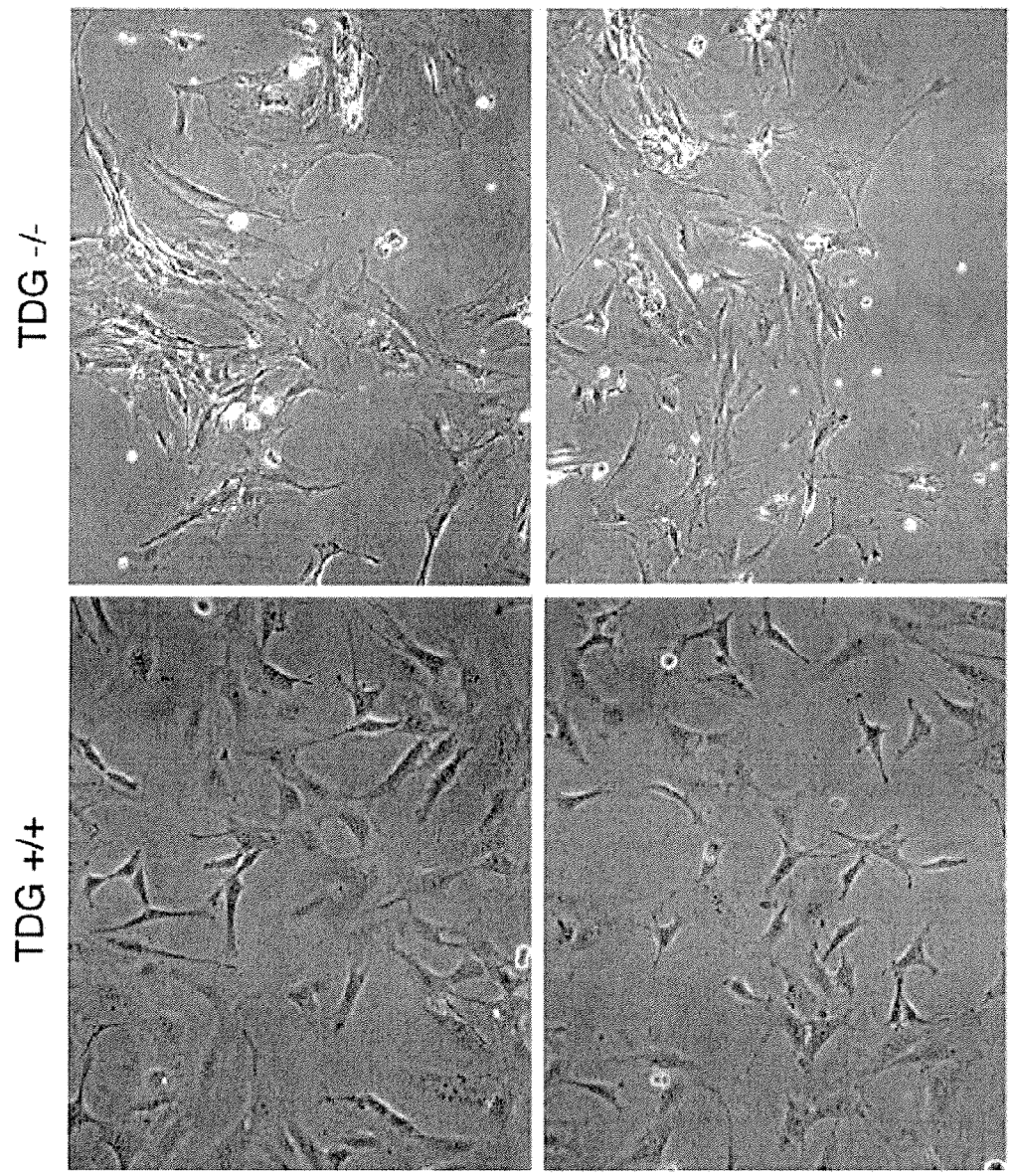
FIG. 8 shows the morphology of TDG wild type (+/+) and knock-out (−/−) MEFs.

Targeted Inactivation of TDG is Associated with Reduced Cellular Proliferation in Mouse Embryo Fibroblasts As described in Examples 2 and 3 above, both Mel501 and MULL cells showed reduced proliferation upon downregulation of their endogenous levels of TDG. A similar effect was noted in mouse embryo fibroblasts (MEFs) derived from mouse embryos with targeted inactivation (knock-out) of TDG. Compared to their wild type (no TDG knock-out) counterpart, TDG knock-out MEFs exhibited reduced proliferation (FIG. 7). This decreased proliferation rate was associated with morphological changes (flattened, enlarged, elongated cytoplasm), resembling those of senescent cells (FIG. 8).

Example 5

Analysis of Cellular Processes

Figure 9:
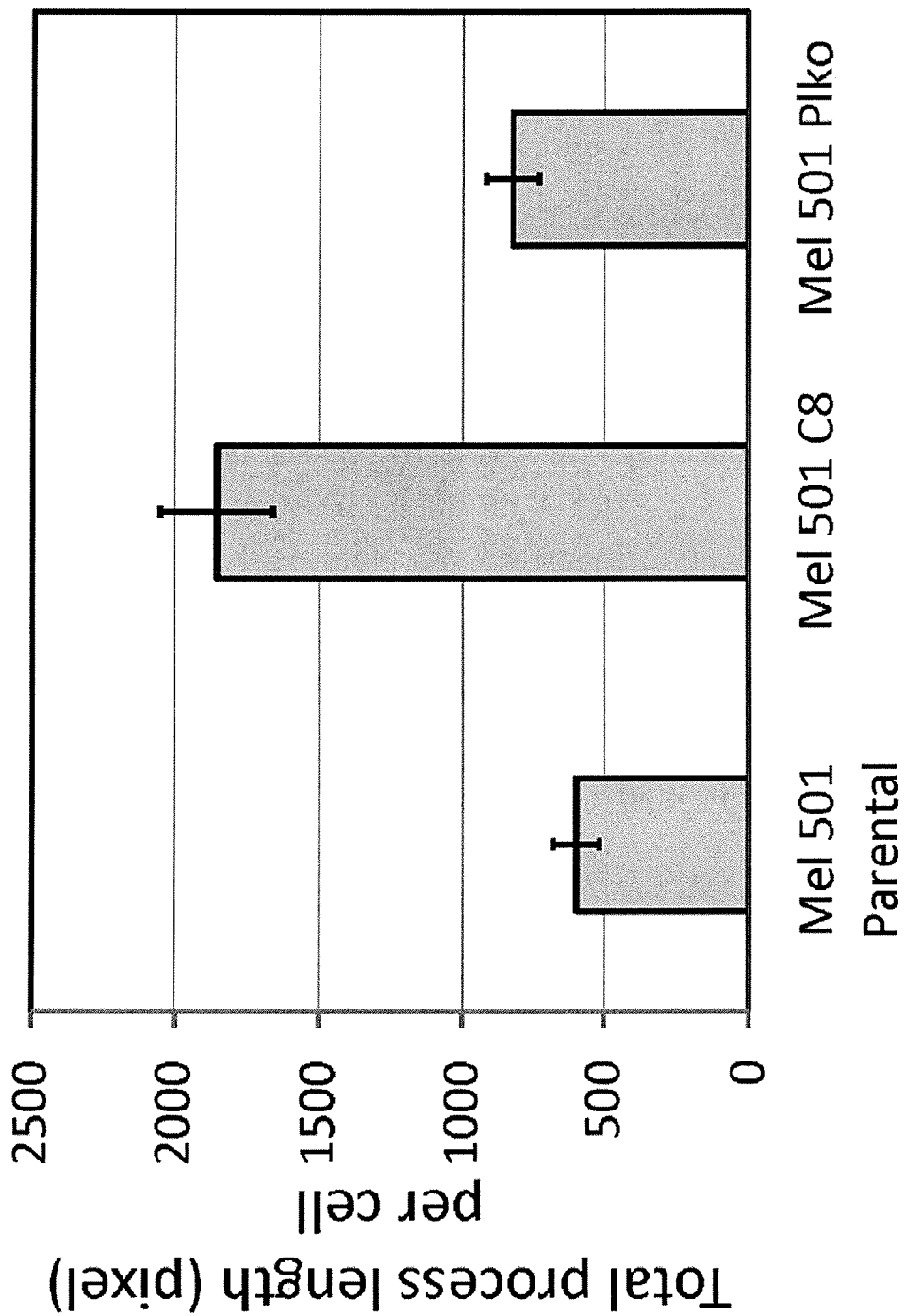
FIG. 9 shows the total process length in parental Mel501 cells, shC8 Mel501 cells and pLKO Mel 501 cells.
Figure 10:
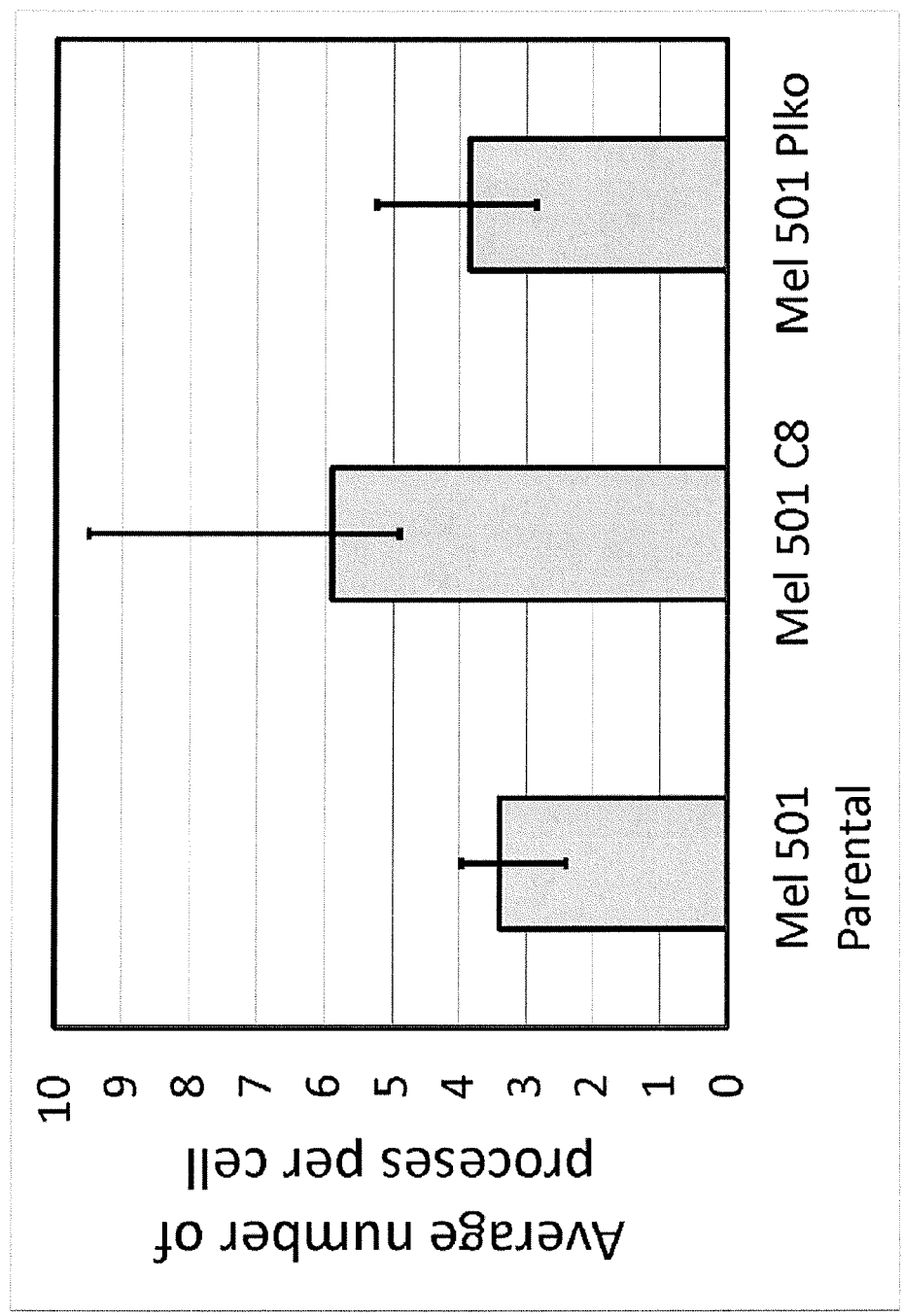
FIG. 10 shows a quantitation of cellular processes in parental Mel501 cells, shC8 Mel501 cells and pLKO Mel 501 cells.

To quantify the effect of TDG downregulation on the differentiation of lentivirus-infected Mel501 cells, further analysis was conducted on the cellular processes resembling dendrites, since it is believed that these represent a significant feature of differentiation. Image analysis-based approaches similar to the ones used to quantify dendrite development during neurogenesis were used. By using Image J software on microscope images of the different cultures, total length of processes per cell (in pixels) was measured, as well as the number of processes per cell. The results showed that Mel501 cells infected with the sh lentivirus C8 directed against TDG mRNA exhibit an increase in both total length of processes per cell (FIG. 9) and in the number of processes per cell (FIG. 10).

Example 6

Cell Cycle Arrest and Multinucleation

Figure 11:
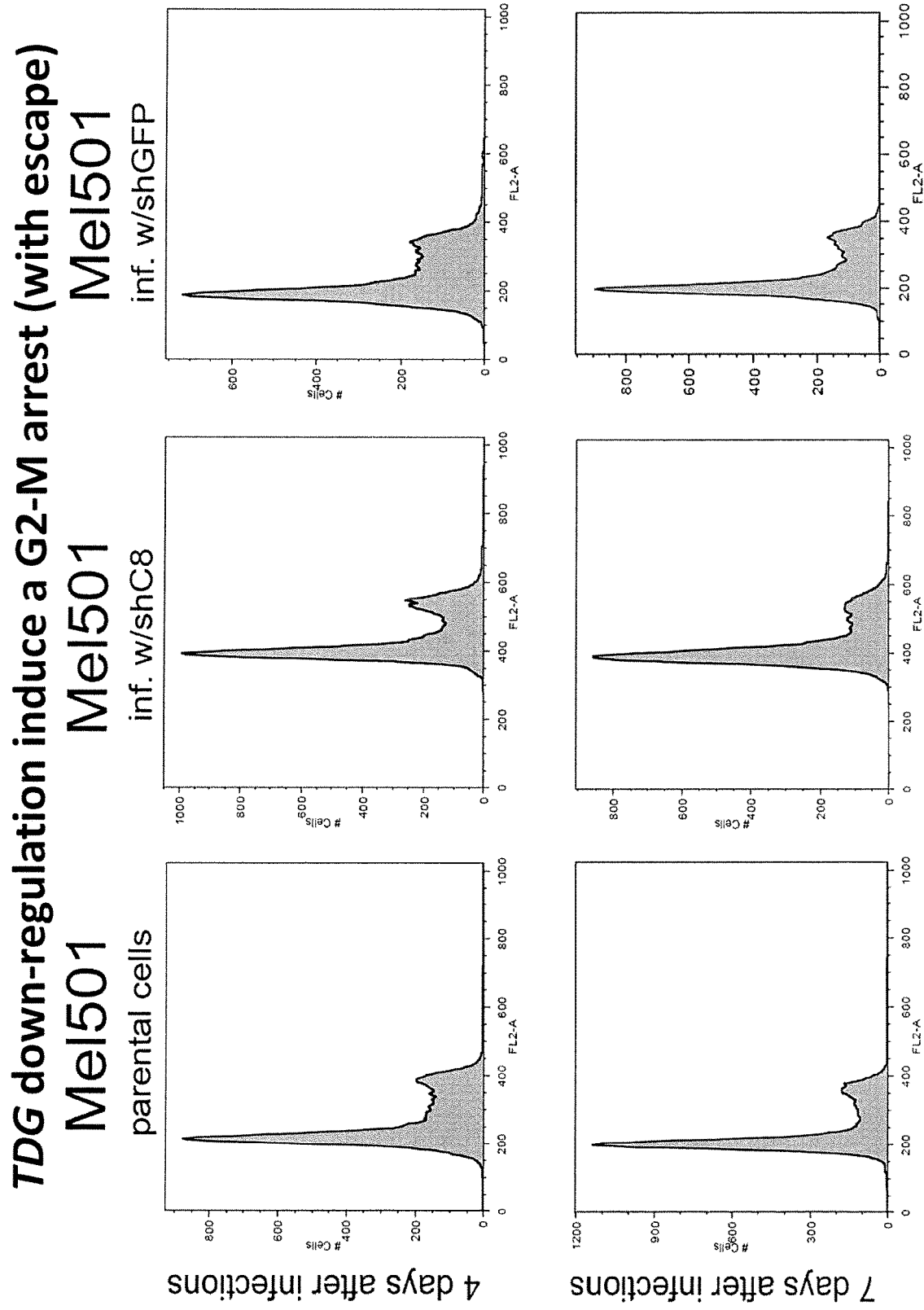
FIG. 11 shows a G2-M phase cell cycle arrest in TDG-downregulated MEL501 cells.
Figure 12:
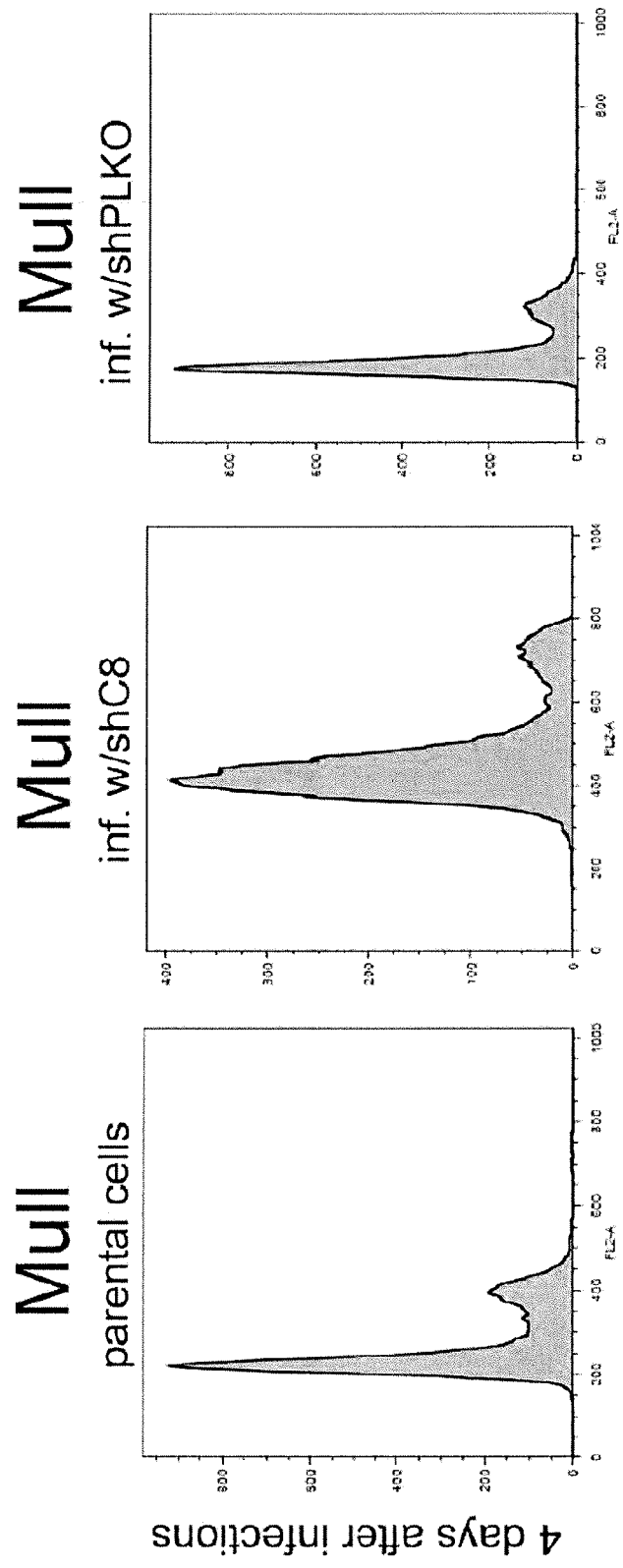
FIG. 12 shows a G2-M phase cell cycle arrest in TDG-downregulated Mull cells.
Figure 13:
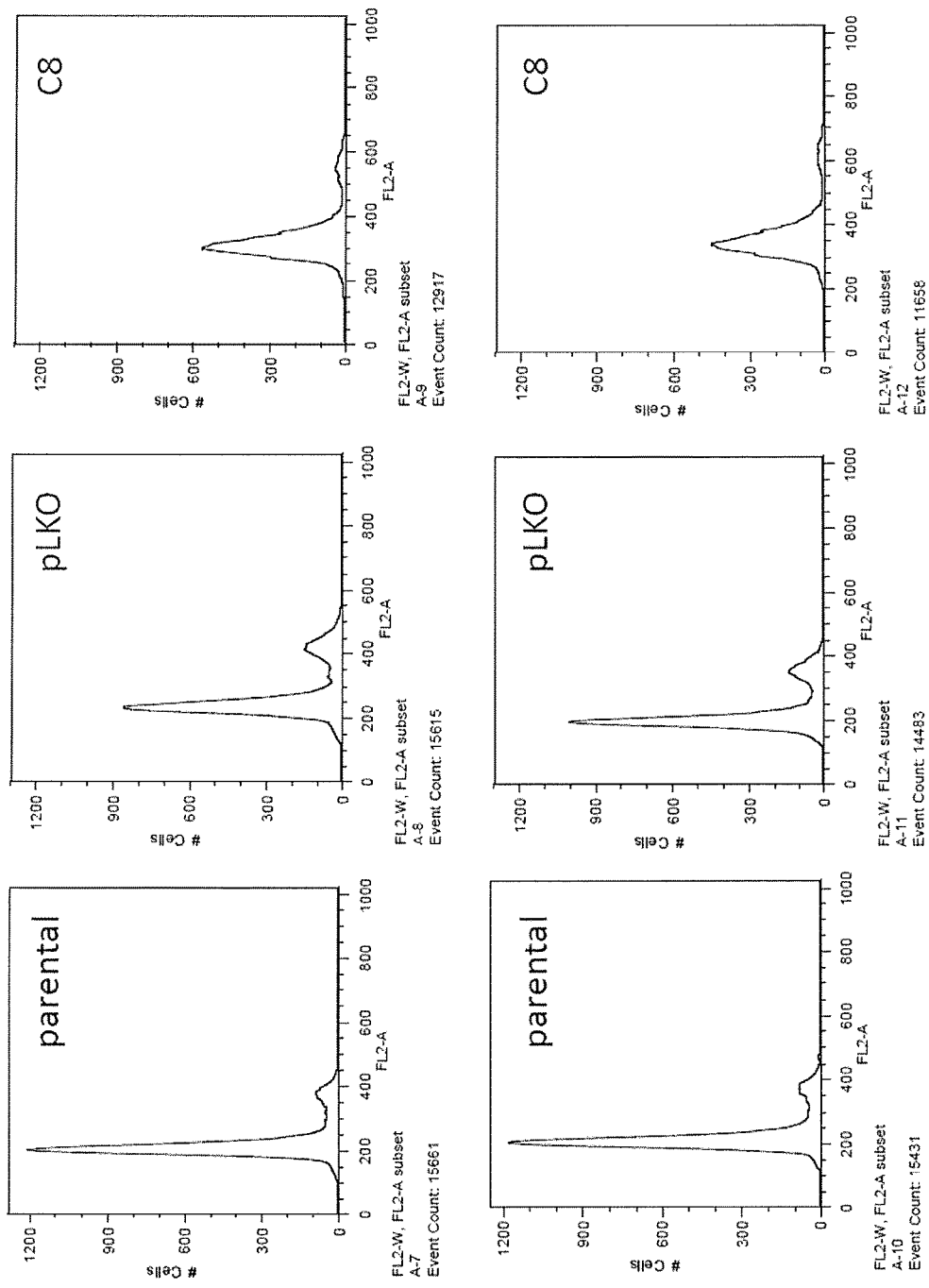
FIG. 13 shows an S phase cell cycle arrest in TDG-downregulated SK28 cells.
Figure 14:
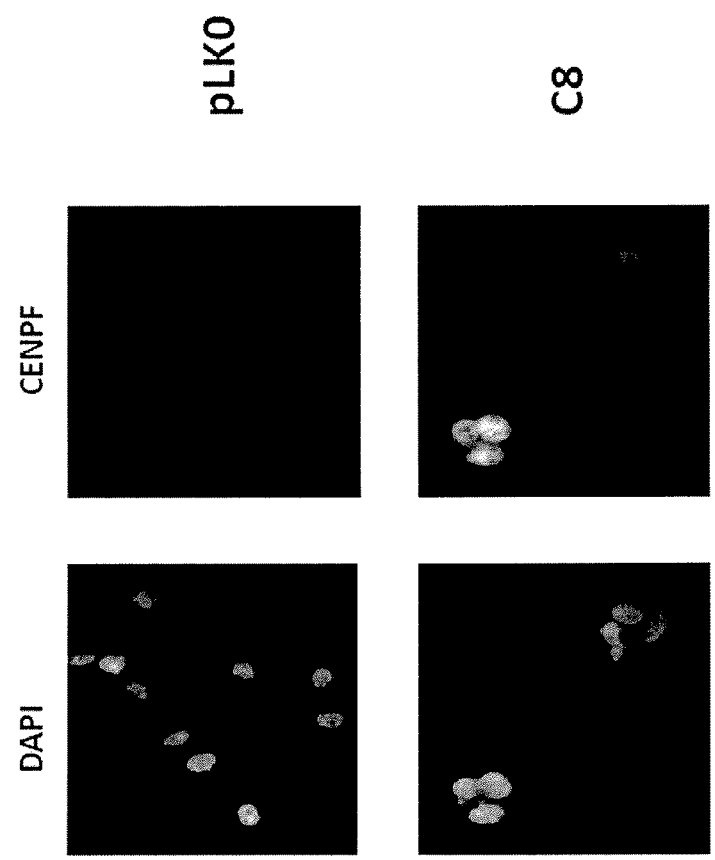
FIG. 14 shows a staining with an antibody against CENPF of TDG-downregulated MEL501 cells.
Figure 15:
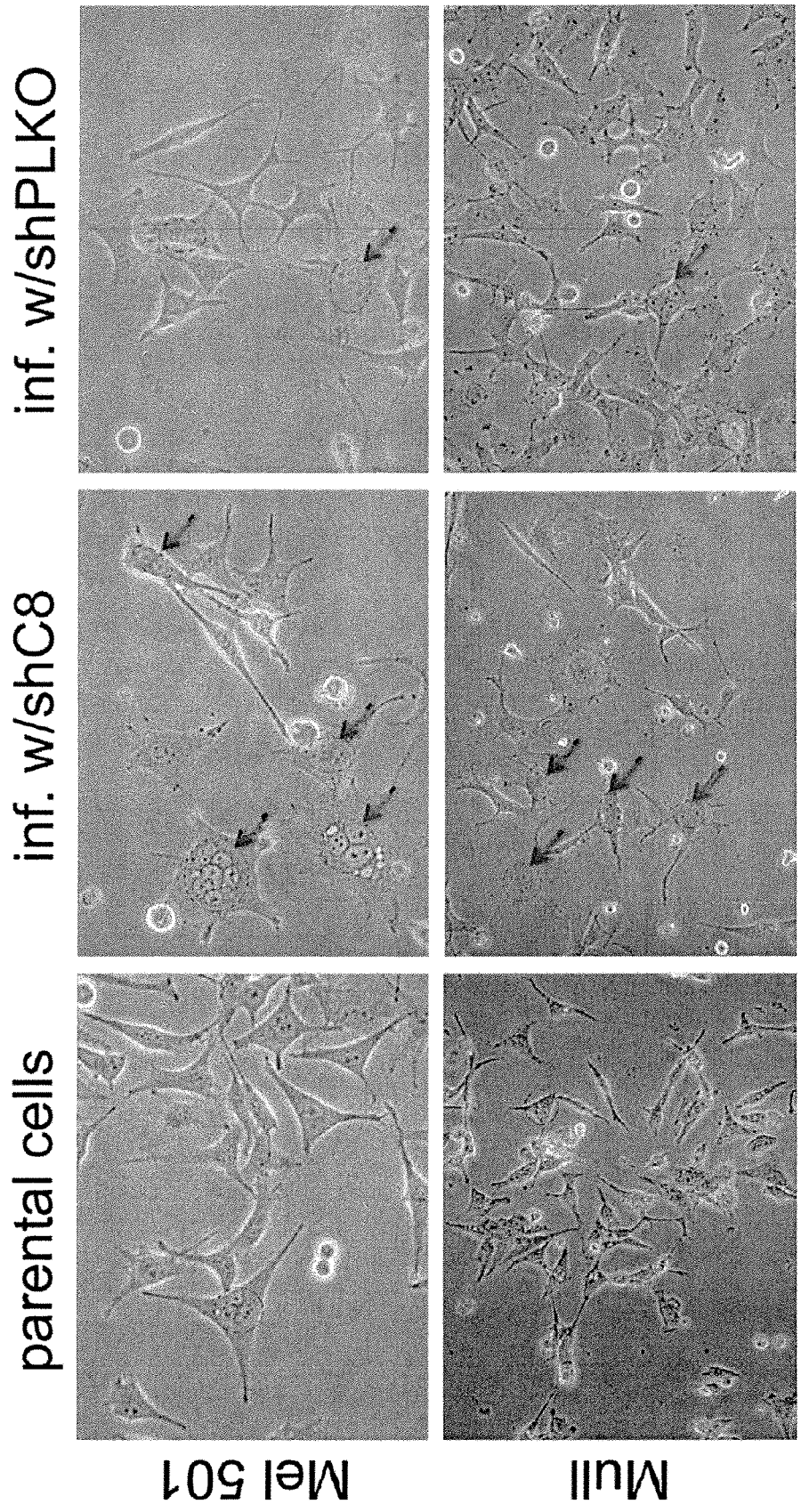
FIG. 15 shows multinucleated MEL501 cells following downregulation of TDG.

The foregoing examples indicate that downregulation of TDG induces growth arrest in melanoma cell lines. Additional experiments further characterized this growth arrest, and showed that downregulation of TDG induces cell cycle arrest either in the G2-M phase (as an example, MEL501 or Mull melanoma cell lines) or S phase (as an example SK28 melanoma cell lines) of the cell cycle, as shown by florescence activated cell sorting (FACS) (FIGS. 11-13). In addition, staining of TDG-downregulated MEL501 cells with an antibody against CENPF indicated that these cells are arrested in either late S phase or G2 phase of the cell cycle (FIG. 14). Some MEL501, Mull and SK28 cells with TDG downregulation escaped the cell cycle arrest and accumulated >4n DNA content, in agreement with the appearance of multinucleated cells following TDG downregulation (FIG. 15).

Example 7

Decrease of MITF Levels and Induction of Senescence

Figure 16:
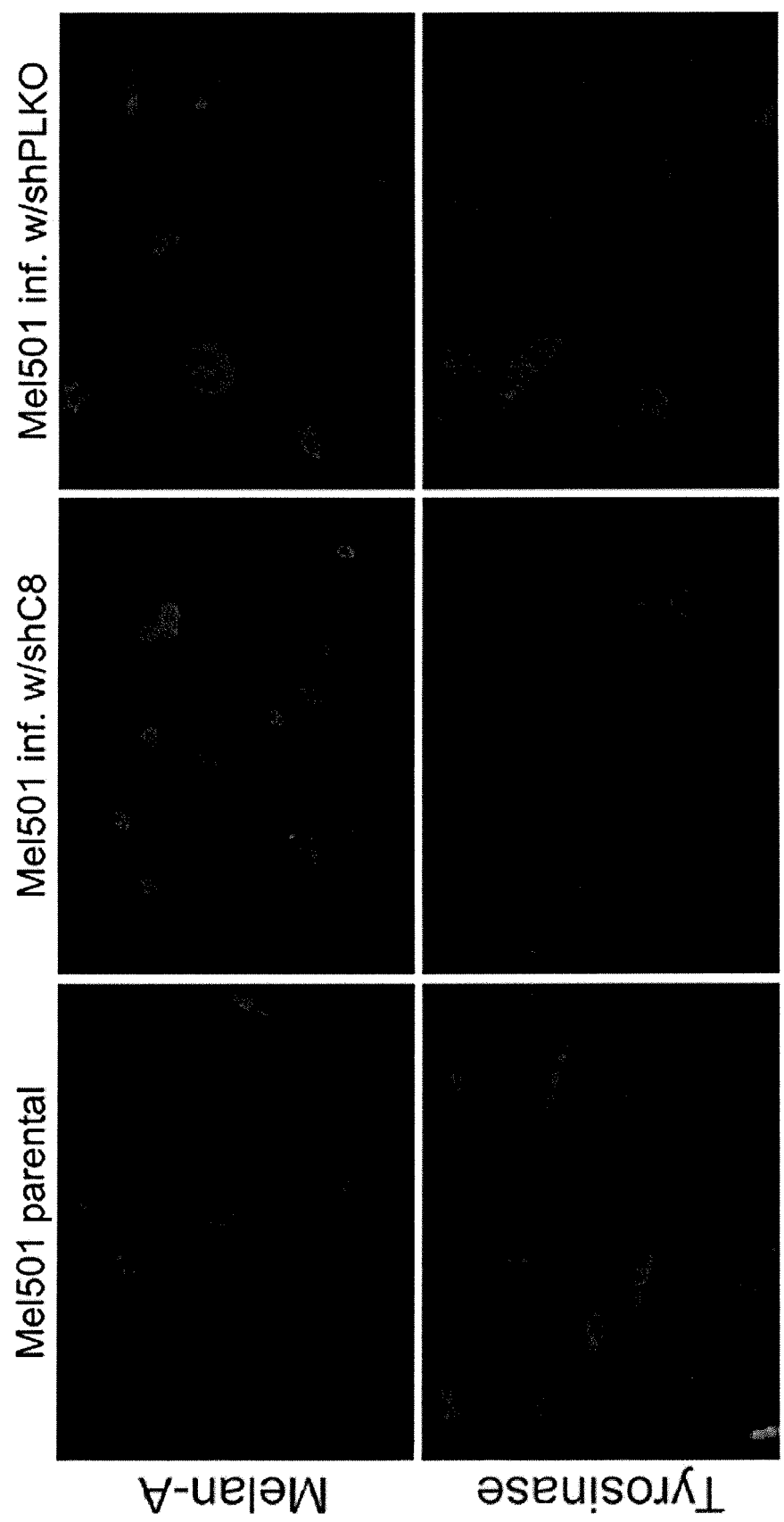
FIG. 16 shows reduced staining of melanocytic markers MelanA/Mart1 and Tyrosinase in TDG-downregulated MEL501 cells.

Downregulation of TDG is associated with increased expression of Tuj-1, a neuronal differentiation marker. It has now been observed that the levels of melanocytic differentiation markers Tyrosinase and Melan-A/MART1 were reduced by TDG downregulation (FIG. 16). The main transcriptional regulator of Tyrosinase and Melan-A/MART1 expression is the Microphtalmia Transcription Factor (MITF). Accordingly, MITF levels were assessed in melanoma cell lines with TDG downregulation.

Figure 17:
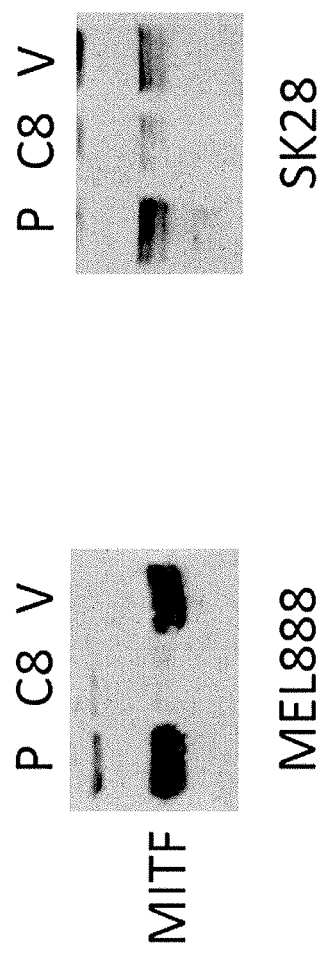
FIG. 17 shows reduced MITF expression in TDG-downregulated melanoma cell lines.

In TDG-downregulated melanoma cells, a dramatic decrease of MITF expression level was detected by Western blotting (FIG. 17). Without intending to be limited to any particular theory or mechanism of action, it is hypothesized that the morphological changes induced by TDG downregulation may be a reflection not only of differentiation, but also of senescence, because MITF silencing has been shown to induce senescence. Thus, it is believed that TDG inhibition may cause senescence of melanoma cells by decreasing MITF levels. It is believed that the growth arrest may be related to the induction of senescence.

Example 8

Reduction of Tumor Formation in Xenotransplants

Cells with TDG downregulation are growth-arrested and exhibit reduction of viability. Therefore, it was hypothesized that their tumorigenic potential should be compromised. Accordingly, the tumorigenicity of such cells was evaluated in a xenotransplant assay. Cells were injected subcutaneously, in either flank, of two SCID mice: SK28 cells infected with the shRNA lentivirus against TDG or SK28 cells infected with control pLKO lentivirus. Only the latter were able to form tumors, whereas the cells with TDG downregulation failed to form tumors (FIG. 18).

Example 9

Identification of Candidate TDG Inhibitors

In order to identify inhibitors of TDG glycosylase activity, an in vitro assay that employs a molecular beacon, a hairpin-shaped oligonucleotide with a G:T or G:U mismatch (substrate) and highly active preparations of recombinant TDG and recombinant AP endonuclease (APE) was employed. In the folded hairpin substrate, the fluorescence of 6-FAM, used as fluorescent label at the 5' end, is quenched by a dabsyl "black hole" moiety at the 3' end. Upon removal of the mismatched T or U by TDG, and incision of the resulting apurinic/apyrimidinic (AP site) by APE, a short oligonucleotide containing 6-FAM was released. The resulting fluorescence was monitored by real-time qPCR over a 2-hour incubation period at 37° C., providing a sensitive and quantitative measurement of repair activity.

Figure 19:
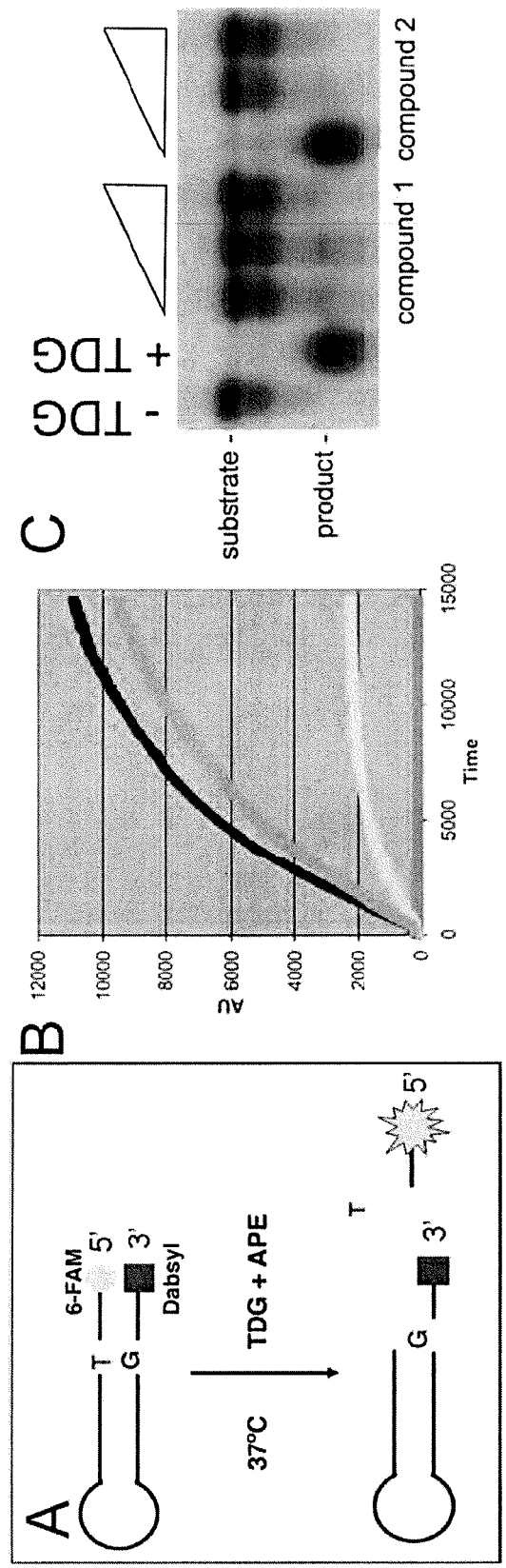
FIG. 19 shows the analysis of TDG activity using qPCR-based assay and identification of candidate inhibitors. (A) Schematic of the molecular beacon assay for G:T repair. (B) Dose dependent inhibition of juglone, a candidate TDG inhibitor at 0 (blue), 5 (teal), 50 (yellow) and 500 (fuchsia) μg/ml. (C) A conventional glycosylase assay confirms inhibition of TDG activity; inhibitors were tested at 100 nM, 10 μM and 1 mM; compound 1, cefixime, is more potent than compound 2, closantel, in this assay.

This assay was optimized for a 96-well and 384-well format. Upon screening the ICCB known bioactive library (approximately 500 compounds) and the Johns Hopkins clinical compound library (approximately 1500 drugs), eighteen and fourteen candidates, respectively (Tables 1 and 2) were identified. Some of these compounds confirmed TDG inhibition in a standard, radioactive-based glycosylase assay (FIG. 19).

TABLE 1
Candidate TDG inhibitors identified by screening the ICCB library.
6-Keto-prostaglandin F1a
7-[(1R,2S)-2-[(E,3S)-3-hydroxyoct-1-enyl]-5-oxocyclopent-3-en-1-yl]heptanoic acid
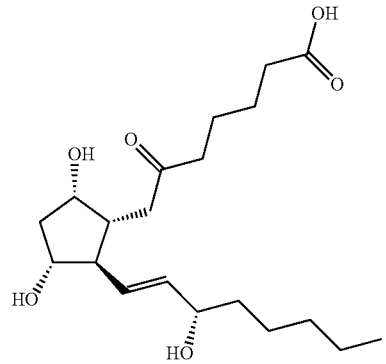 [SMILES: CCCCC[C@H](O)/C=C/[C@@H]1[C@@H](CC(=O)CCCCC(=O)O)[C@@H](O)C[C@H]1O]
E6 Berbamine
6,6',7-Trimethoxy-2,2'-dimethylberbaman-12-yl acetate
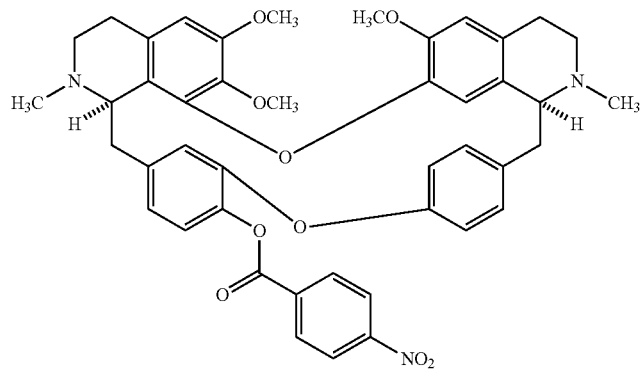
Prostaglandin A1
9-oxo-15S-hydroxy-prosta-10,13E-dien-1-oic acid
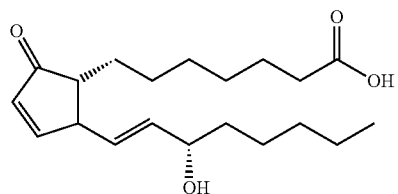
Juglone
5-hydroxynaphthoquinone
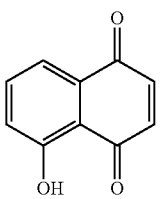
GW-5074
3-(3,5-Dibromo-4-hydroxybenzylidine-5-iodo-1,3-dihydro-indol-2-one
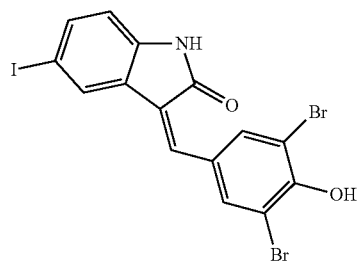 [SMILES: O=C1Nc2ccc(I)cc2/C1=C/c1cc(Br)c(O)c(Br)c1]

TABLE 1-continued

Candidate TDG inhibitors identified by screening the ICCB library.

Rottlerin
(E)-1-[6-[(3-acetyl-2,4,6-trihydroxy-5-
methylphenyl)methyl]-5,7-dihydroxy-2,2-
dimethylchromen-8-yl]-3-phenylprop-2-en-1-
one

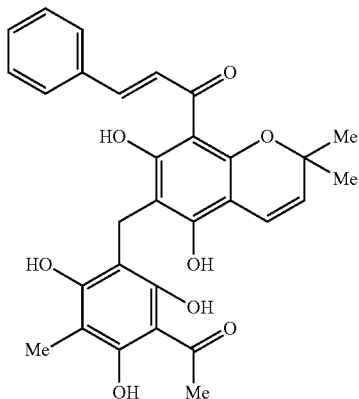 [SMILES: CC(=O)c1c(O)c(C)c(O)c(Cc2c(O)c3c(c(C(=O)/C=C/c4ccccc4)c2O)OC(C)(C)C=C3)c1O]

TABLE 2

Candidate TDG inhibitors identified by screening the JHCC library.

Cefixime
(6R,7R)-7-{[2-(2-amino-1,3-thiazol-
4-yl)-2-
(carboxymethoxyimino)acetyl]
amino}-3-ethenyl-8-oxo-5-thia-1-
azabicyclo[4.2.0]oct-2-ene-2-
carboxylic acid

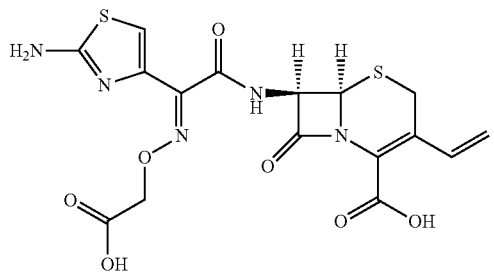 [SMILES: C=CC1=C(C(=O)O)N2C(=O)[C@@H](NC(=O)/C(=N/OCC(=O)O)c3csc(N)n3)[C@H]2SC1]

Idarubicin
(1S,3S)-3-acetyl-3,5,12-trihydroxy-
6,11-dioxo-1,2,3,4,6,11-
hexahydrotetracen-1-yl 3-amino-
2,3,6-trideoxo-α-L-lyxo-
hexopyranoside

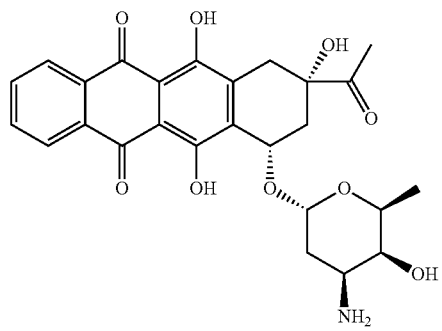 [SMILES: CC(=O)[C@]1(O)Cc2c(O)c3c(c(O)c2[C@@H](O[C@H]2C[C@H](N)[C@H](O)[C@H](C)O2)C1)C(=O)c1ccccc1C3=O]

Doxorubicin
(7S,9S)-7-[(2R,4S,5S,6S)-4-amino-5-
hydroxy-6-methyloxan-2-yl]oxy-
6,9,11-trihydroxy-9-(2-
hydroxyacetyl)-4-methoxy-8,10-
dihydro-7H-tetracene-5,12-dione

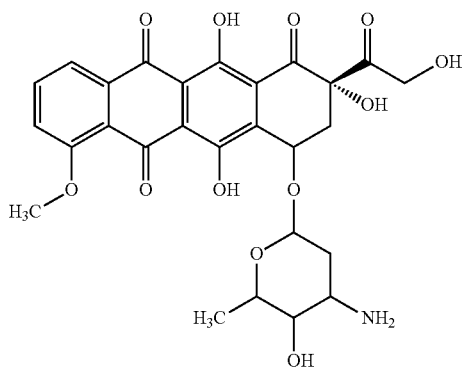 [SMILES: COc1cccc2c1C(=O)c1c(O)c3c(c(O)c1C2=O)C(=O)[C@@](O)(C(=O)CO)CC3OC1CC(N)C(O)C(C)O1]

TABLE 2-continued

Candidate TDG inhibitors identified by screening the JHCC library.

Methenamine
(Hexamethylenetetramine)

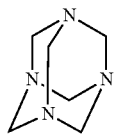

Congo red
disodium 4-amino-3-[4-[4-(1-amino-4-sulfonato-naphthalen-2-yl)diazenylphenyl]phenyl]diazenyl-naphthalene-1-sulfonate

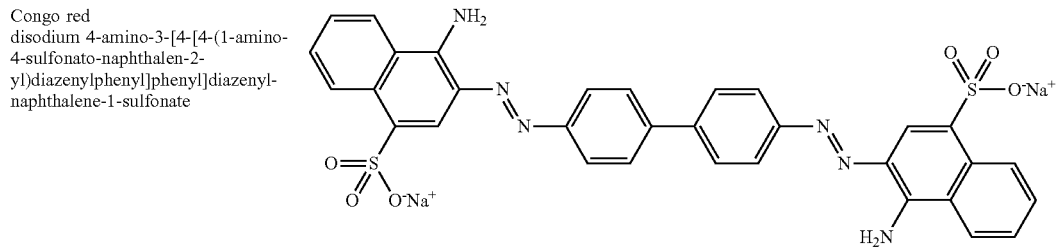

Sodium ferric gluconate (Ferrlecit ®)

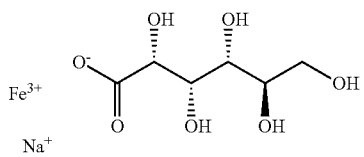

Ferrous sulfate

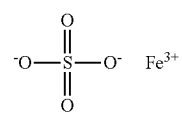

Aurothioglucose
gold(I) (2S,3S,4R,5S)-3,4,5-trihydroxy-6-(hydroxymethyl)-oxane-2-thiolate

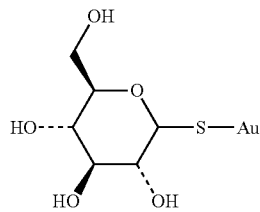

Evans blue
tetrasodium (6E,6'E)-6,6-[(3,3'-dimethylbiphenyl-4,4'-diyl)di(1E)hydrazin-2-yl-1-ylidene]bis(4-amino-5-oxo-5,6-dihydronaphthalene-1,3-disulfonate)

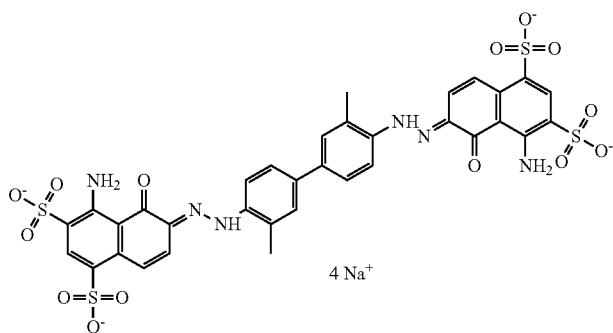 [SMILES: Cc1cc(-c2ccc(N/N=C3\C=Cc4c(S(=O)(=O)[O-])cc(S(=O)(=O)[O-])c(N)c4C3=O)c(C)c2)ccc1N/N=C1\C=Cc2c(S(=O)(=O)[O-])cc(S(=O)(=O)[O-])c(N)c2C1=O]

Closantel
5'-Chloro-4'-(4-chloro-α-cyanobenzyl)-3,5-diiodo-2'-methylsalicylanilide, N-[5-Chloro-4-(4-chloro-α-cyanobenzyl)-2-methylphenyl]-2-hydroxy-3,5-diiodobenzamide

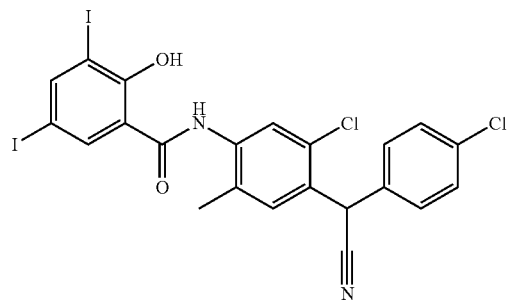 [SMILES: Cc1cc(C(C#N)c2ccc(Cl)cc2)c(Cl)cc1NC(=O)c1cc(I)cc(I)c1O]

TABLE 2-continued

Candidate TDG inhibitors identified by screening the JHCC library.

| | |
|---|---|
| Cinchonine sulfate | 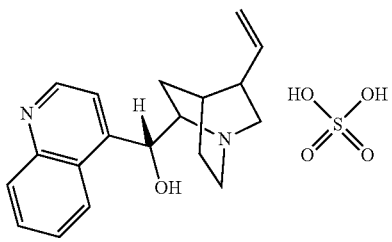 |
| Hexadimethrine bromide (Polybrene) 1,5-dimethyl-1,5-diazaundecamethylene polymethobromide, hexadimethrine bromide- | 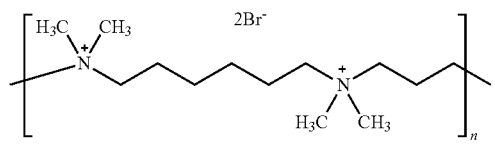 |
| Indigotindisulfonate (Indigo Carmine) 3,3'-dioxo-2,2'-bis-indolyden-5,5'-disulfonic acid disodium salt | 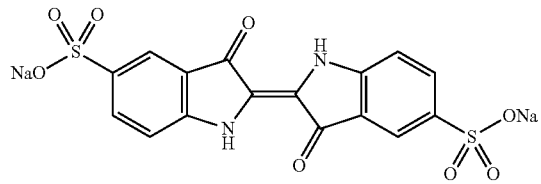 |
| Protamine chloride, grade V | MPRRRRSSSRPVRRRRRPRVSRRRRRRGGRRRR (SEQ ID NO: 8) |

Example 10

Downregulation or Inhibition of TDG Causes Elevated Levels of 5-carboxylcytosine (5caC)

Figure 20:
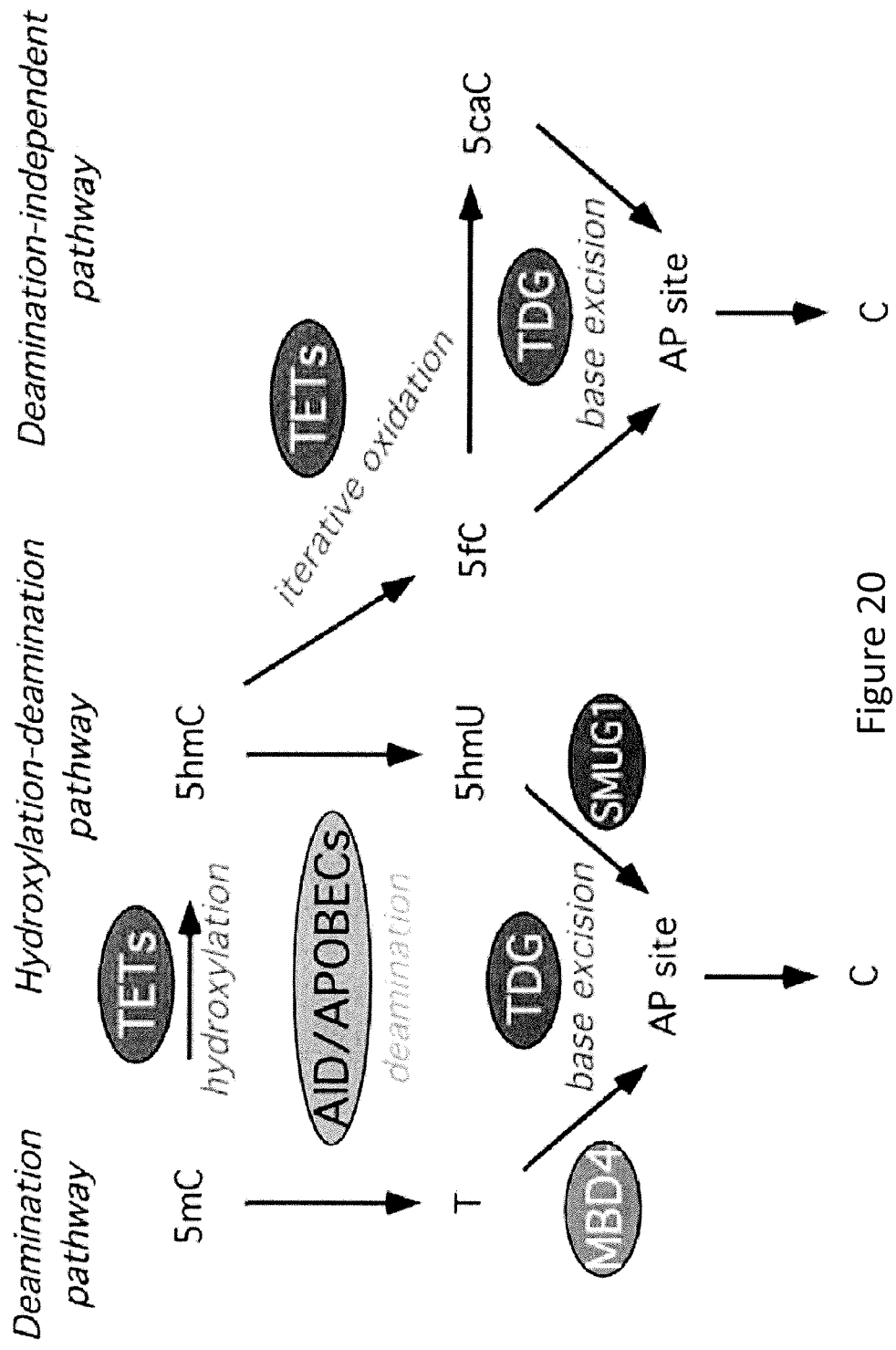
FIG. 20 shows a schematic of the central role of TDG in DNA demethylation pathways: the deamination (left), hydroxylation-deamination (center) and deamination-independent (right) pathways are shown. 5 mC: 5-methylcytosine; 5hmC: 5-hydroxymethylcytosine; T: thymine; 5hmU: 5-hydroxymethyluracil; 5fC: 5-formylcytosine; 5caC: 5-carboxylcytosine; AP site: apurinic/apyrimidinic site; C: cytosine.
Figure 21:
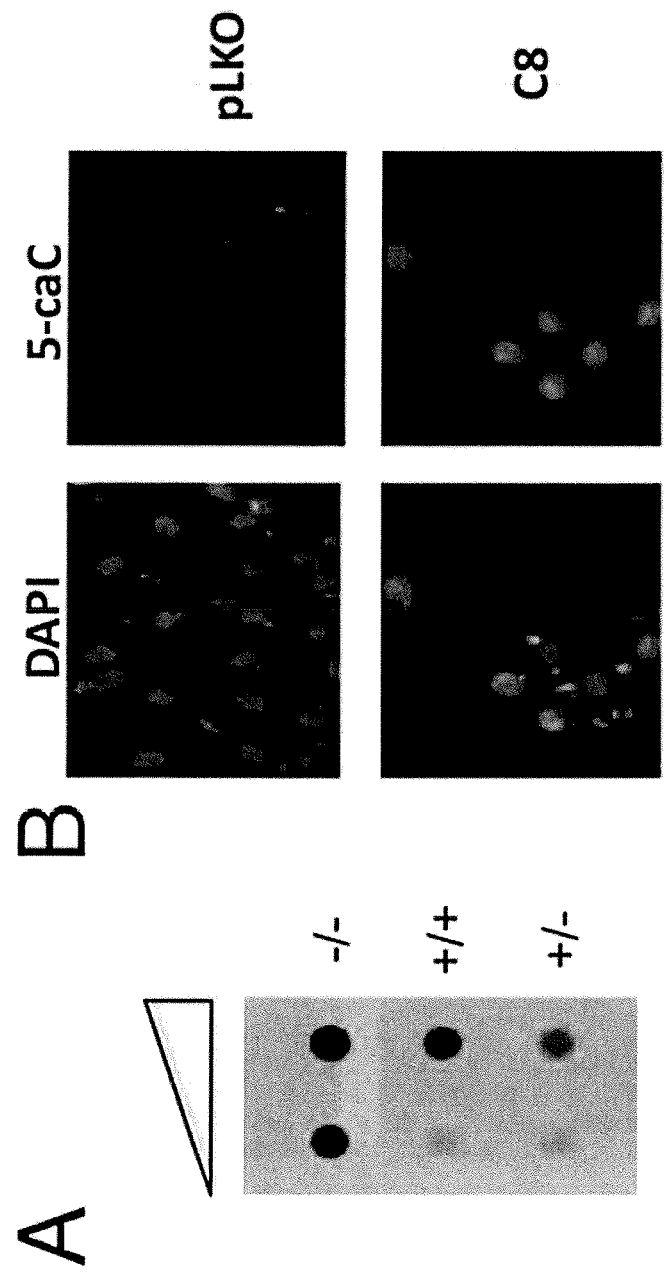
FIG. 21 shows elevated 5-carboxylcytosine levels associated with targeted inactivation or downregulation of TDG. (A) Decreasing dilutions of genomic DNA from embryos of the indicated Tdg genotype were blotted and detected with antibody anti-5caC. (B) Immuno-fluorescence documenting elevated levels of 5caC in SK28 melanoma cell line infected with sh lentivirus against TDG (C8) or vector control (pLKO).

DNA modifying enzymes of the ten-eleven translocation (TET) family and base excision repair DNA glycosylases are involved in DNA demethylation, an epigenetic de-modification associated with gene activation. Specifically, TET family proteins TET1, 2 and 3 are dioxygenases that oxidize 5-methylcytosine to 5-hydroxymethylcytosine (5hmC). TET proteins subsequently convert the 5hmC to 5-formylcytosine (5fC) and 5-carboxylcytosine (5caC), and TDG removes 5fC and 5caC opposite G. While potential accessory roles of the glycosylases MED1/MBD4 and SMUG1, and deaminases of the AID/APOBEC family cannot be ruled out completely, the bulk of the currently available data point to the TET-TDG axis as a central component of the pathways mediating active cytosine demethylation via conversion of 5 mC to 5hmC, and then sequentially to 5fC and 5caC (FIG. 20). By immunodot-blot of DNA extracted from cells and immunofluorescence staining of cells, elevated levels of 5caC were detected in embryos genetically deleted of TDG and cell lines downregulated of TDG. Without intending to be limited to any particular theory or mechanism of action, it is believed that inhibition or loss of TDG alters the epigenome (FIG. 21).

Figure 22:
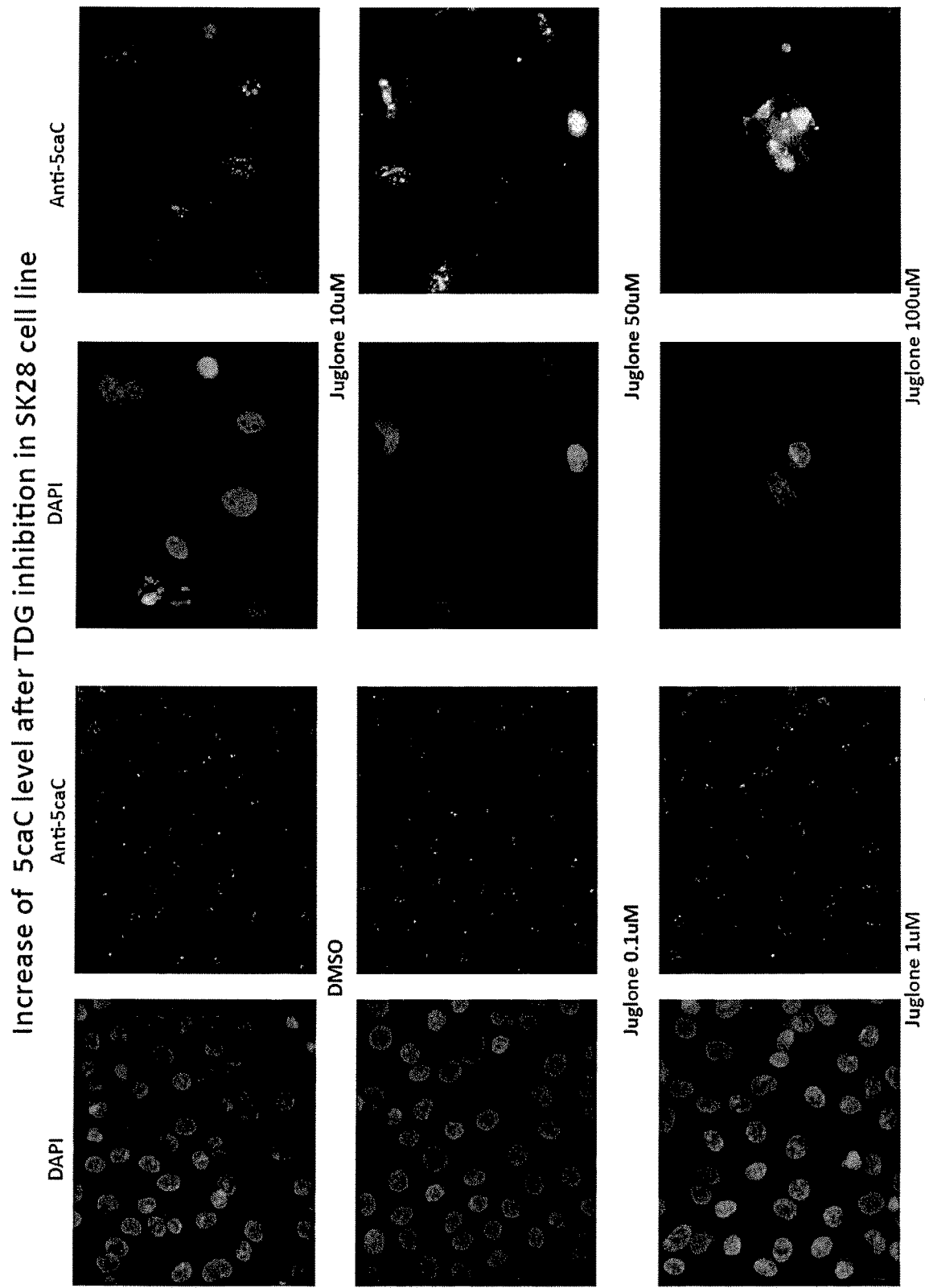
FIG. 22 shows elevated 5-carboxylcytosine levels associated with treatment of SK28 melanoma cells with the candidate TDG inhibitor, juglone.
Figure 23:
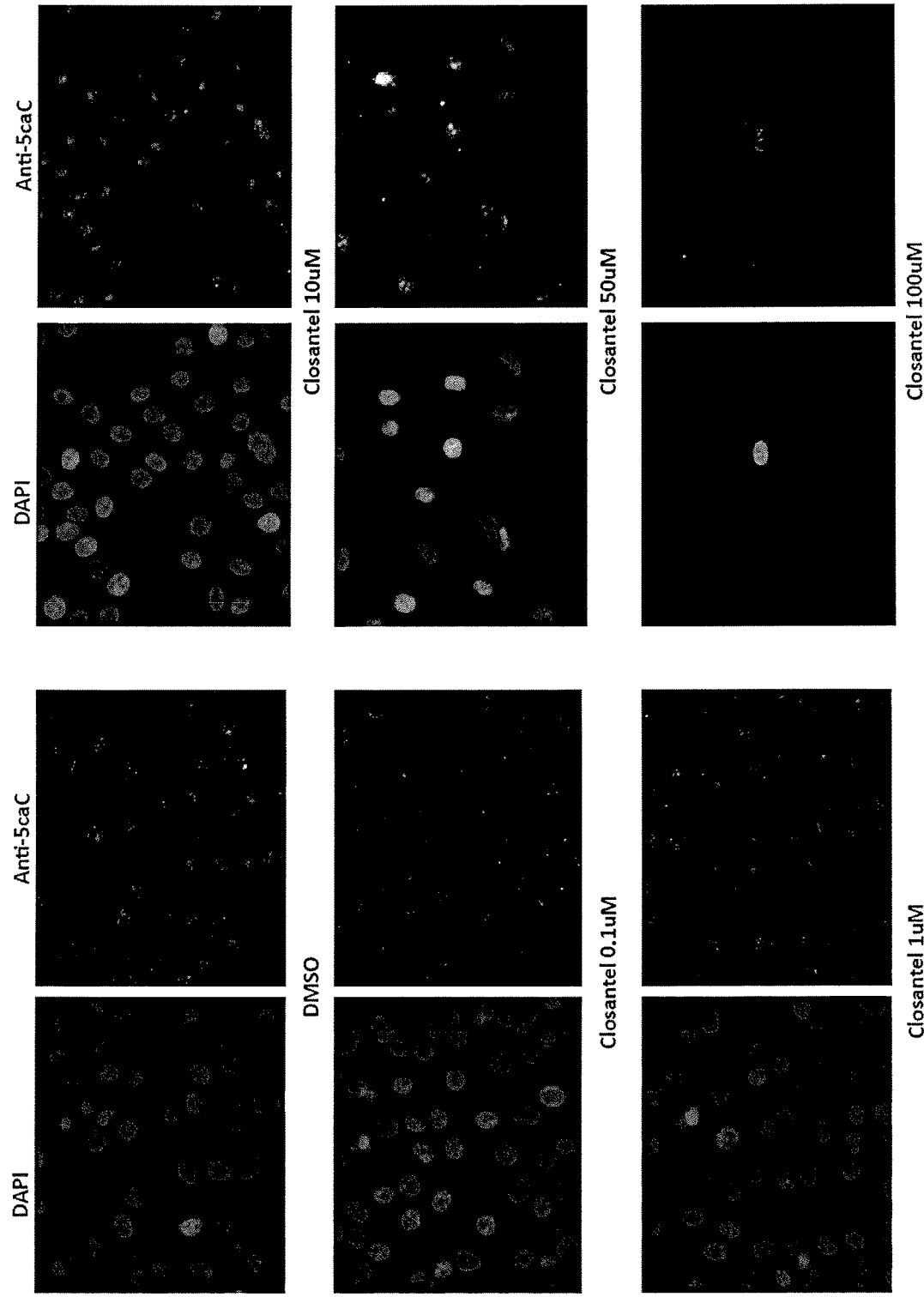
FIG. 23 shows elevated 5-carboxylcytosine levels associated with treatment of SK28 melanoma cells with the candidate TDG inhibitor, closantel.

Two compounds from the screen described in Example 9, juglone and closantel, were found to increase 5caC staining in the nuclei of cells in culture, confirming TDG inhibition (FIGS. 22-23).

Example 11

Two Putative TDG Inhibitors Reduce Cell Viability and Clonogenic Capacity

Juglone, a quinone chemopreventive agent extracted from the black walnut, closantel, an anti-helminth drug, and cefixime, an antibiotic from the cephalosporin family were found to reduce cell viability and clonogenic capacity of SK28 cells in a concentration-dependent fashion (FIG. 24-26). Tests were conducted in quadruplicate.

Example 12

Downregulation of TDG Causes the Appearance of RAD51 Foci

Figure 27:
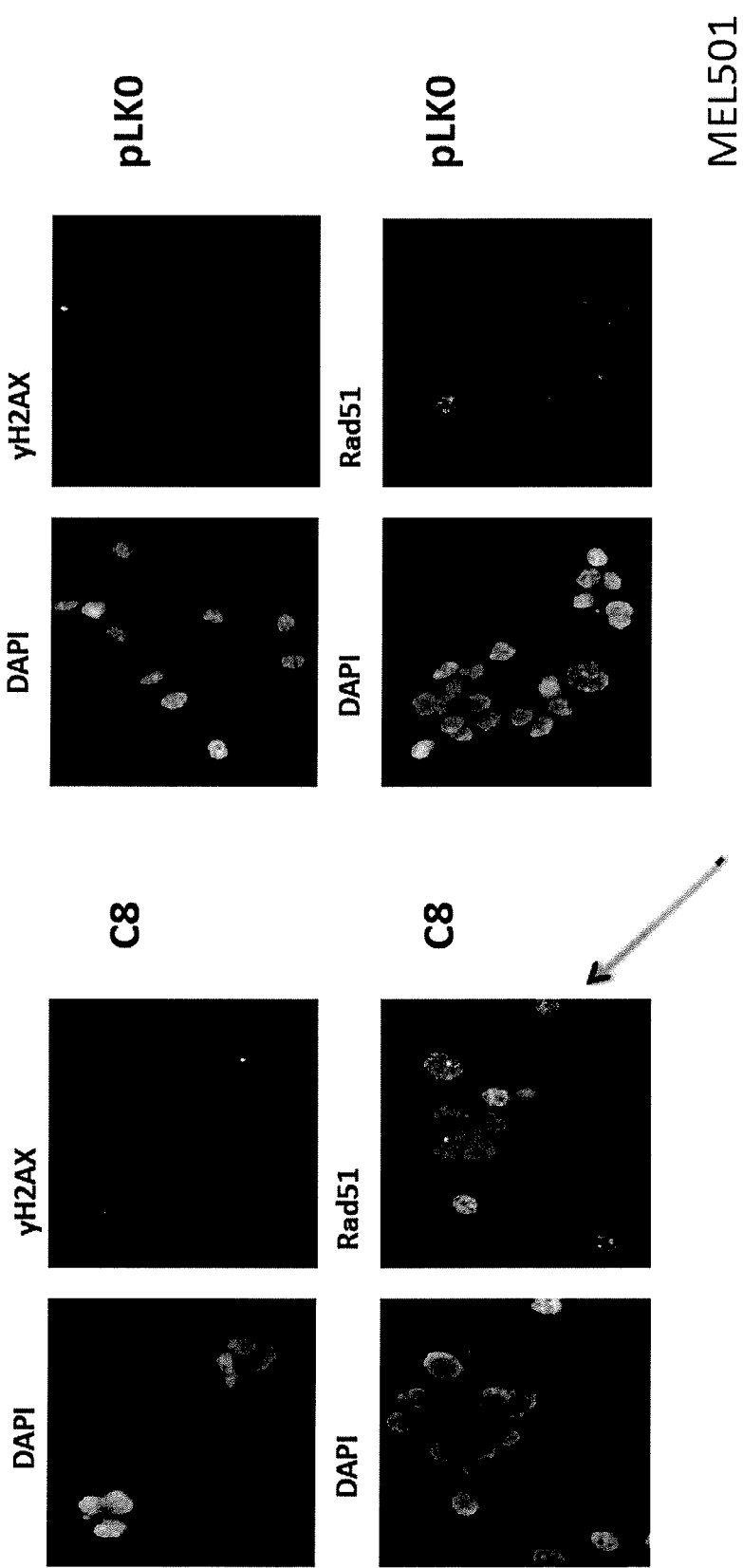
FIG. 27 shows that TDG downregulation leads to RAD51 activation, as assessed by the formation of RAD51 foci, in the absence of gamma-H2AX activation, a marker of DNA damage response.

RAD51 is an important protein in the repair of DNA double strand breaks by homologous recombination. Specifically, RAD51 is involved in the search for homology, forming helical nucleoprotein filaments on DNA that appear as "foci" upon staining with a specific antibody. It was observed that cells with downregulation of TDG accumulate RAD51 foci (FIG. 27). It is believed that TDG downregulation/inhibition potentially may synergize with RAD51 inhibitors for cancer treatment.

Example 13

Downregulation/Inhibition of TDG Synergizes with Temozolomide

Alkylating agents are a class of DNA damaging and anti-cancer drugs whose main mechanism of action consists in the alkylation of guanine in DNA to form 06-methylguanine. Two alkylating agents are used in the clinic, temozolomide and dacarbazine.

Figure 28:
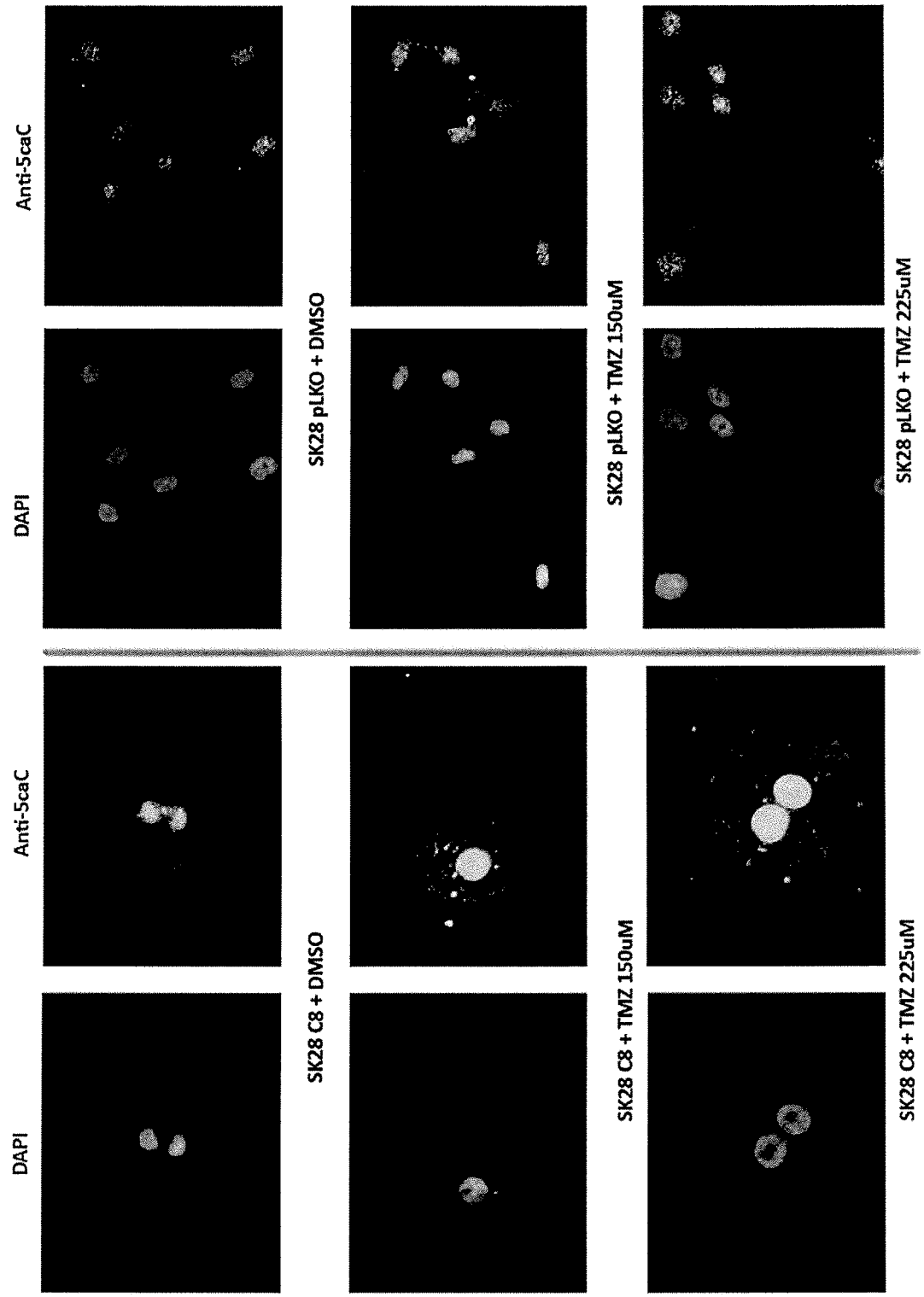
FIG. 28 shows highly elevated 5-carboxylcytosine levels associated with temozolomide treatment combined with downregulation of TDG, suggesting a synergistic effect.
Figure 29:
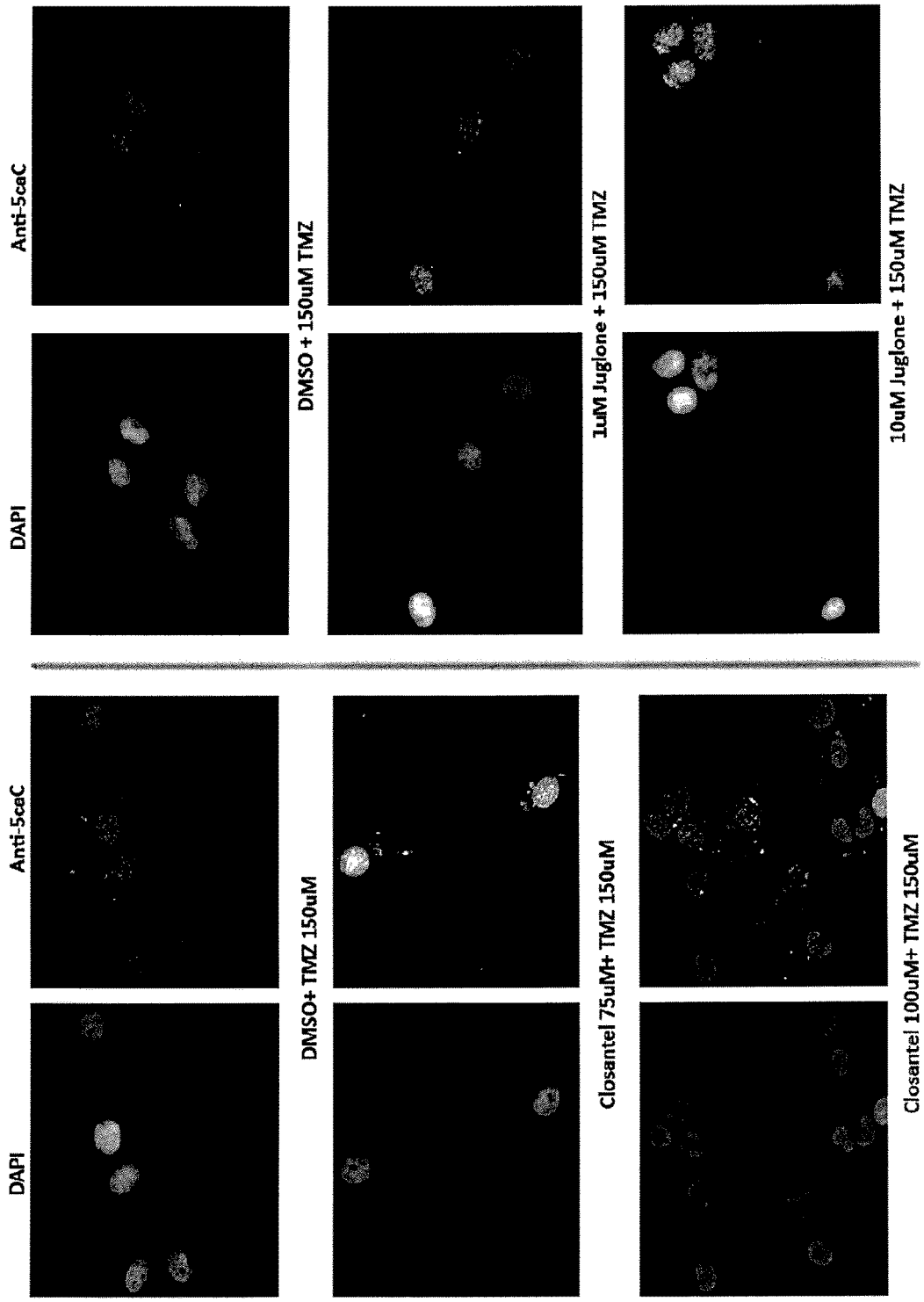
FIG. 29 shows highly elevated 5-carboxylcytosine levels associated with temozolomide treatment combined with treatment of the cells with candidate inhibitors of TDG, juglone and closantel, suggesting a synergistic effect.

Treatment of cancer cells with temozolomide was observed to cause a dramatic increase of 5caC levels when combined with TDG downregulation (FIG. 28) or inhibition (FIG. 29). This indicates that combinatorial treatment of cancer cells with alkylating agents plus TDG downregulation/inhibition can have a synergistic effect in killing cancer cells.

Example 14

Downregulation of TDG Synergizes with Cisplatin

Figure 30:
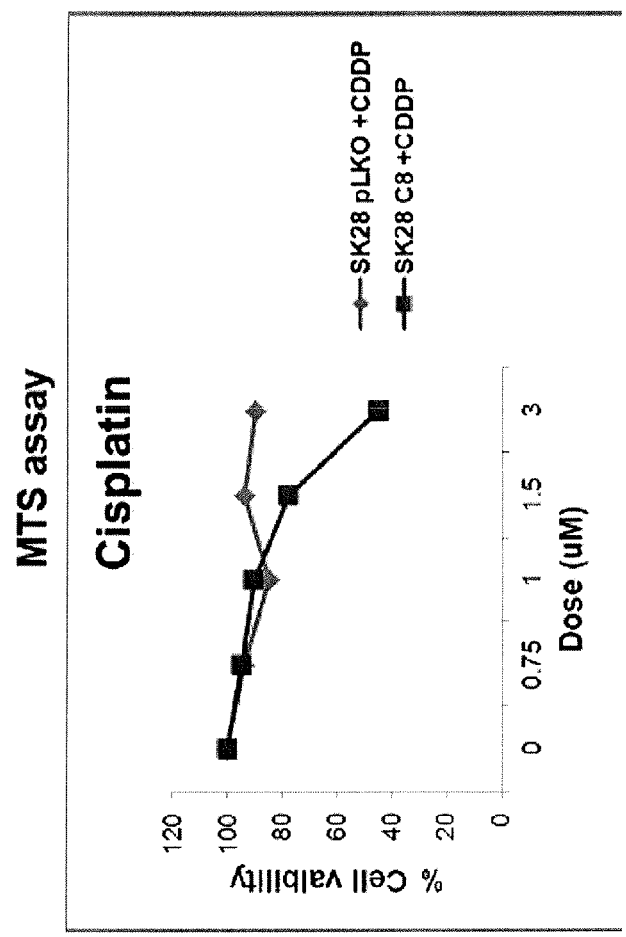
FIG. 30 shows reduction of SK28 cell viability (MTS assay) when cisplatin treatment is combined with TDG downregulation (C8).

Cisplatin is a chemotherapeutic agent that forms intra- and interstrand adducts. It was observed that treatment of cancer cells with cisplatin caused a reduction in viability when combined with TDG downregulation (FIG. 30).

Example 15

Downregulation of TDG Synergizes with Vincristine

Figure 31:
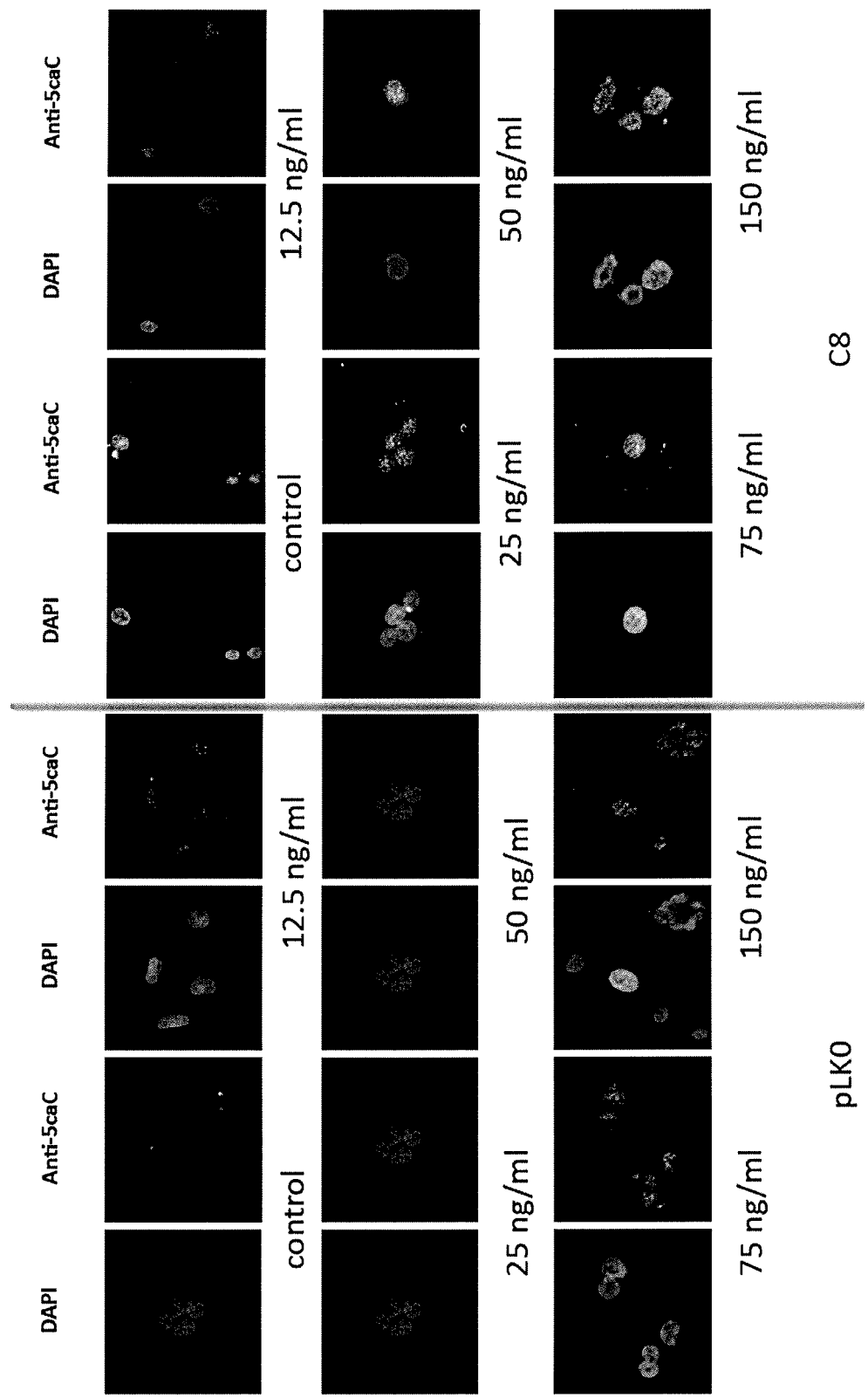
FIG. 31 shows elevated 5caC levels when cells are treated with vincristine even in the absence of TDG downregulation (pLKO); 5caC levels are further increased when vincristine treatment is combined with TDG downregulation (C8).
Figure 32:
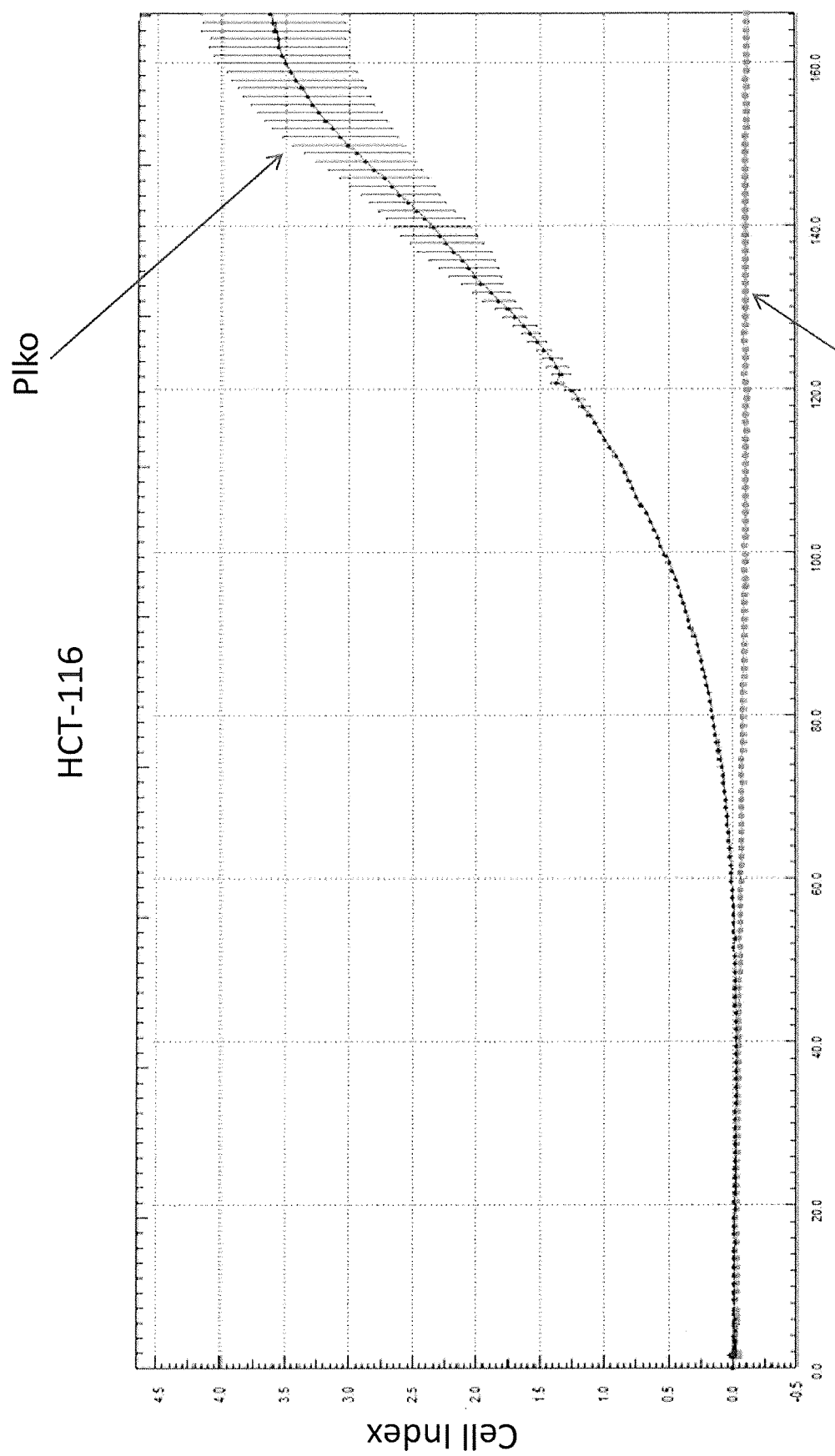
FIG. 32 shows the cell index from HCT-116 (colon cancer) cells infected with an empty vector or C8 lentivirus encoding shRNA for TDG knockdown.
Figure 33:
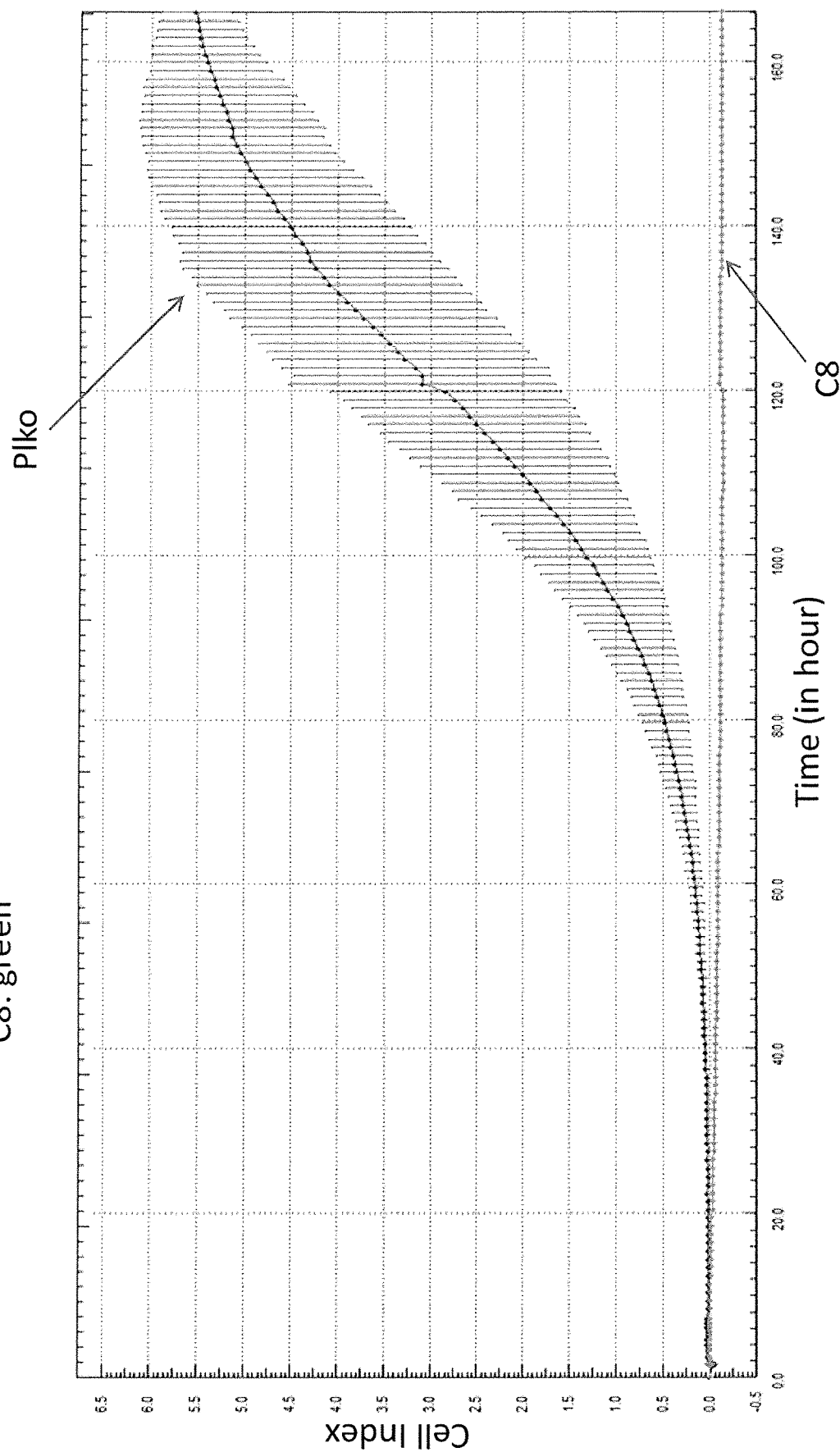
FIG. 33 shows the cell index from A549 (lung cancer) cells infected with an empty vector or C8 lentivirus encoding shRNA for TDG knockdown.
Figure 34:
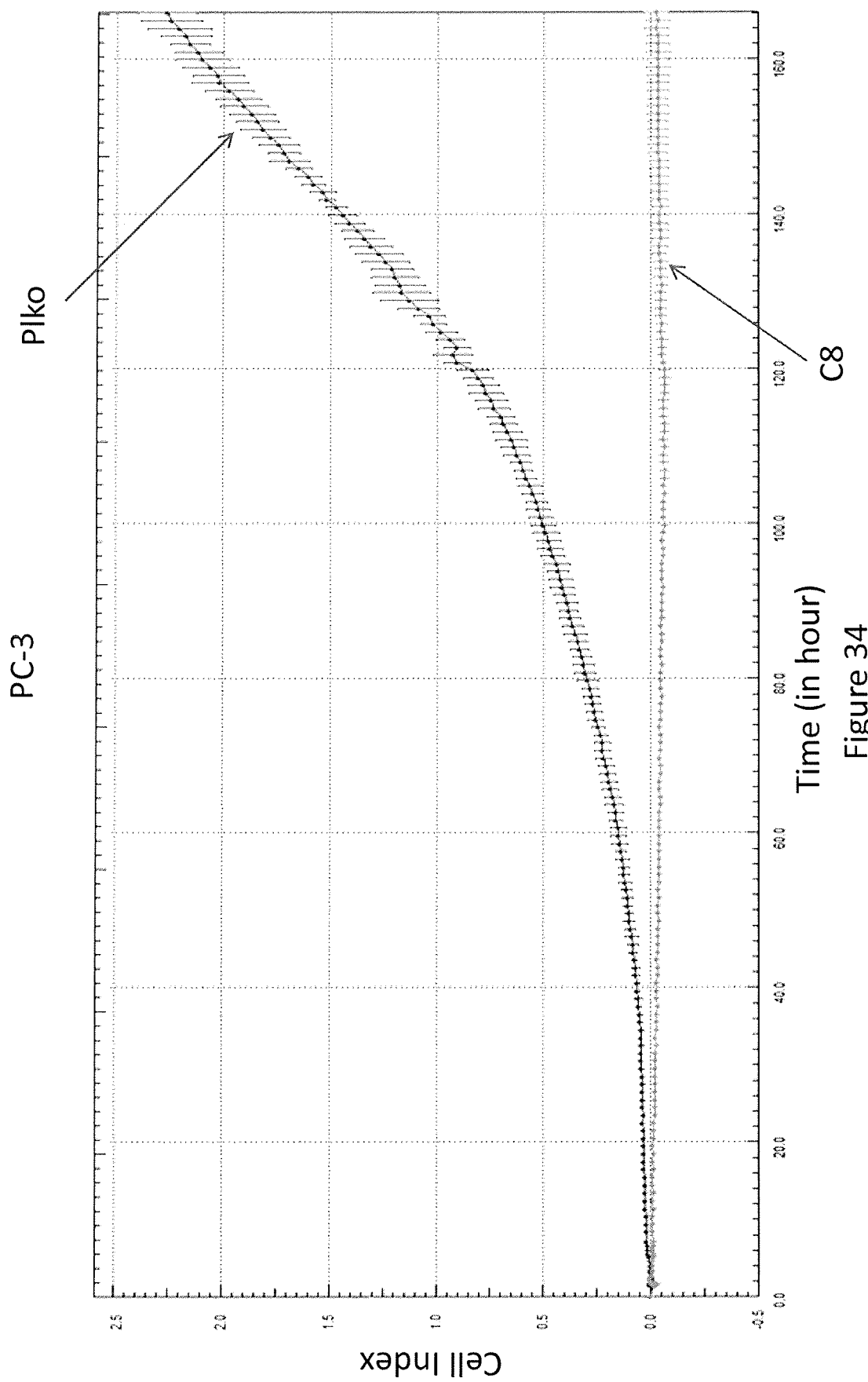
FIG. 34 shows the cell index from PC-3 (prostate cancer) cells infected with an empty vector or C8 lentivirus encoding shRNA for TDG knockdown.
Figure 35:
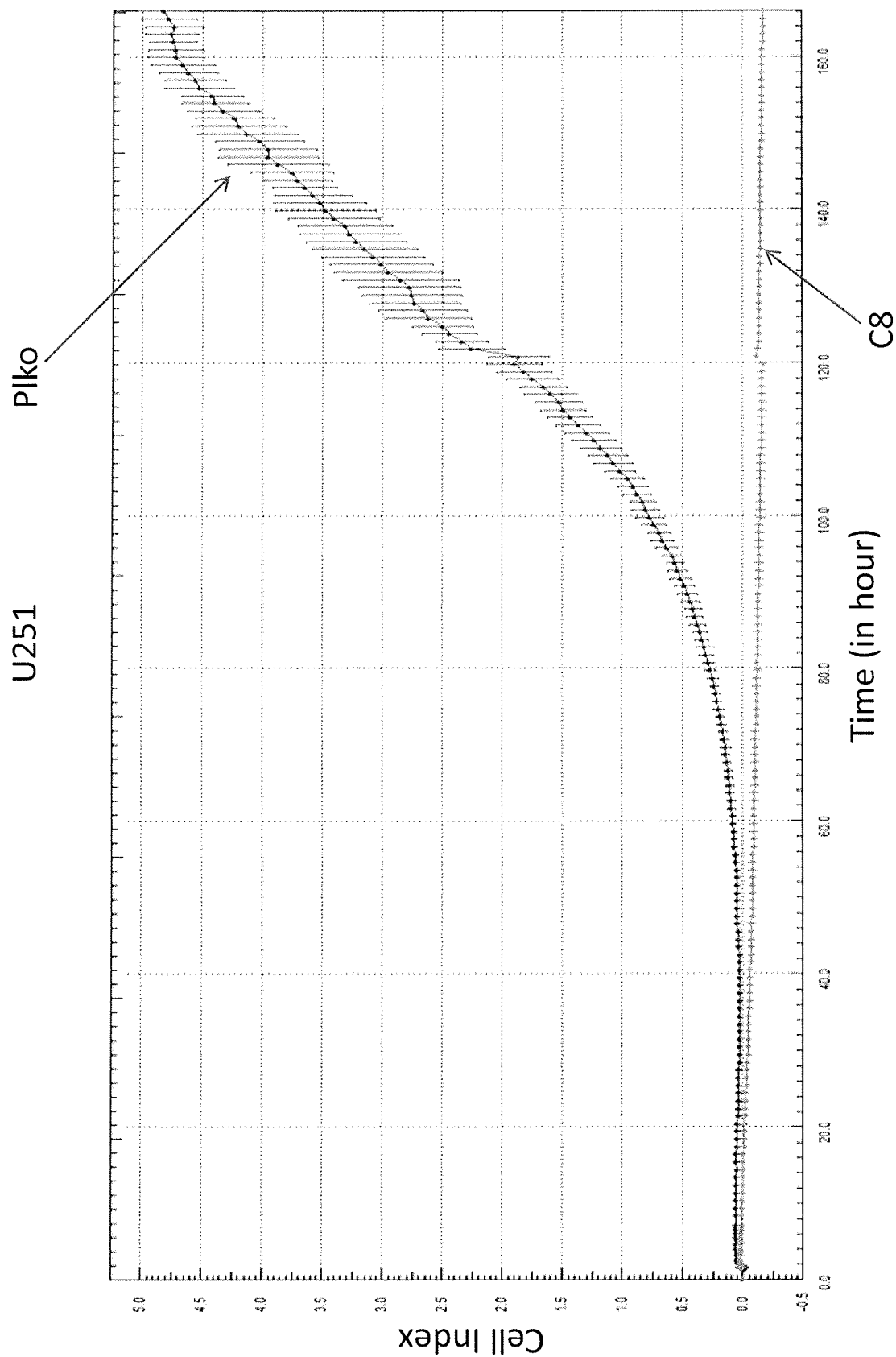
FIG. 35 shows the cell index from U251 (glioblastoma/brain cancer) cells infected with an empty vector or C8 lentivirus encoding shRNA for TDG knockdown.
Figure 36:
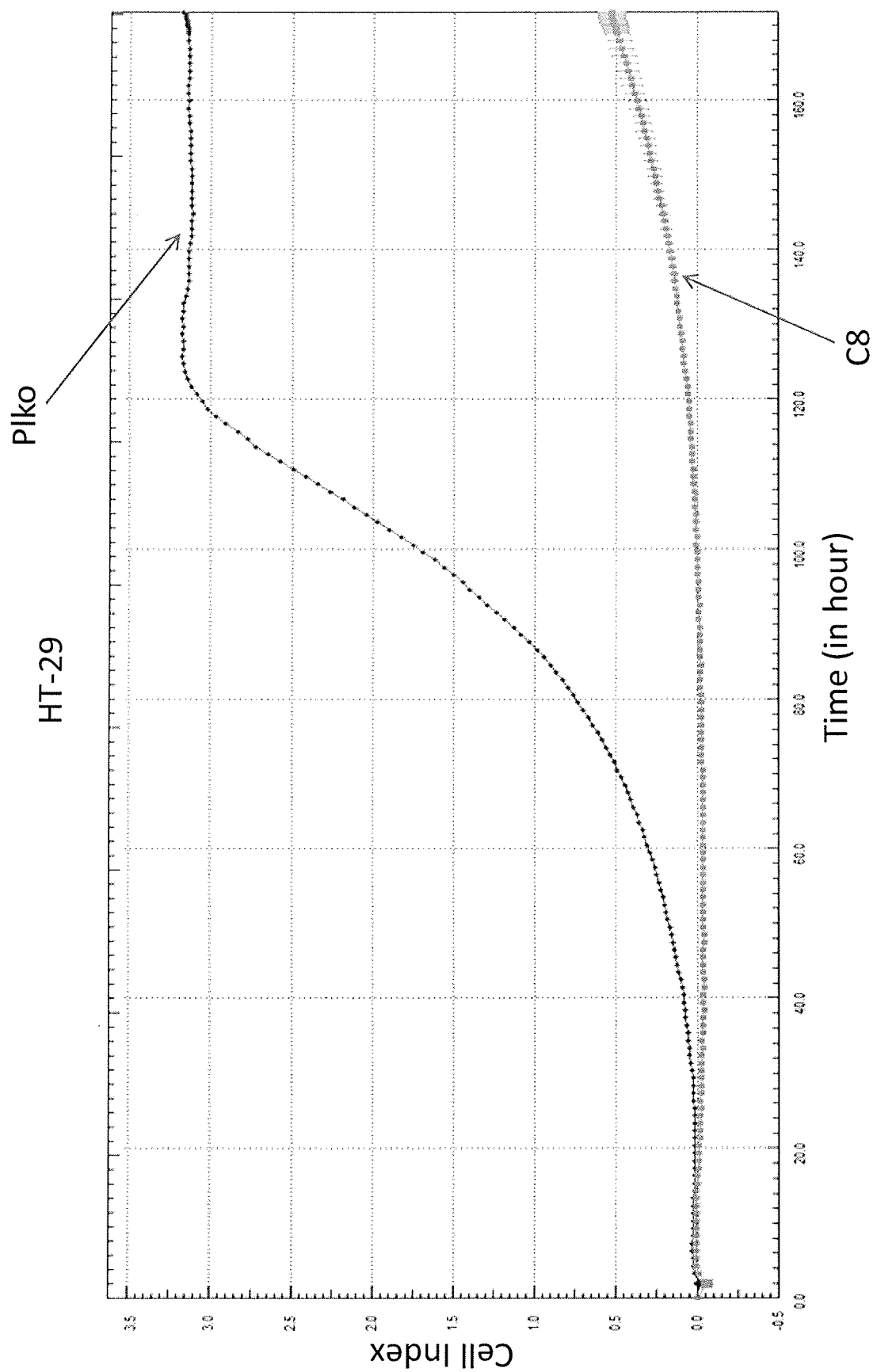
FIG. 36 shows the cell index from HT-29 (recto-sigmoid colon cancer) cells infected with an empty vector or C8 lentivirus encoding shRNA for TDG knockdown.
Figure 37:
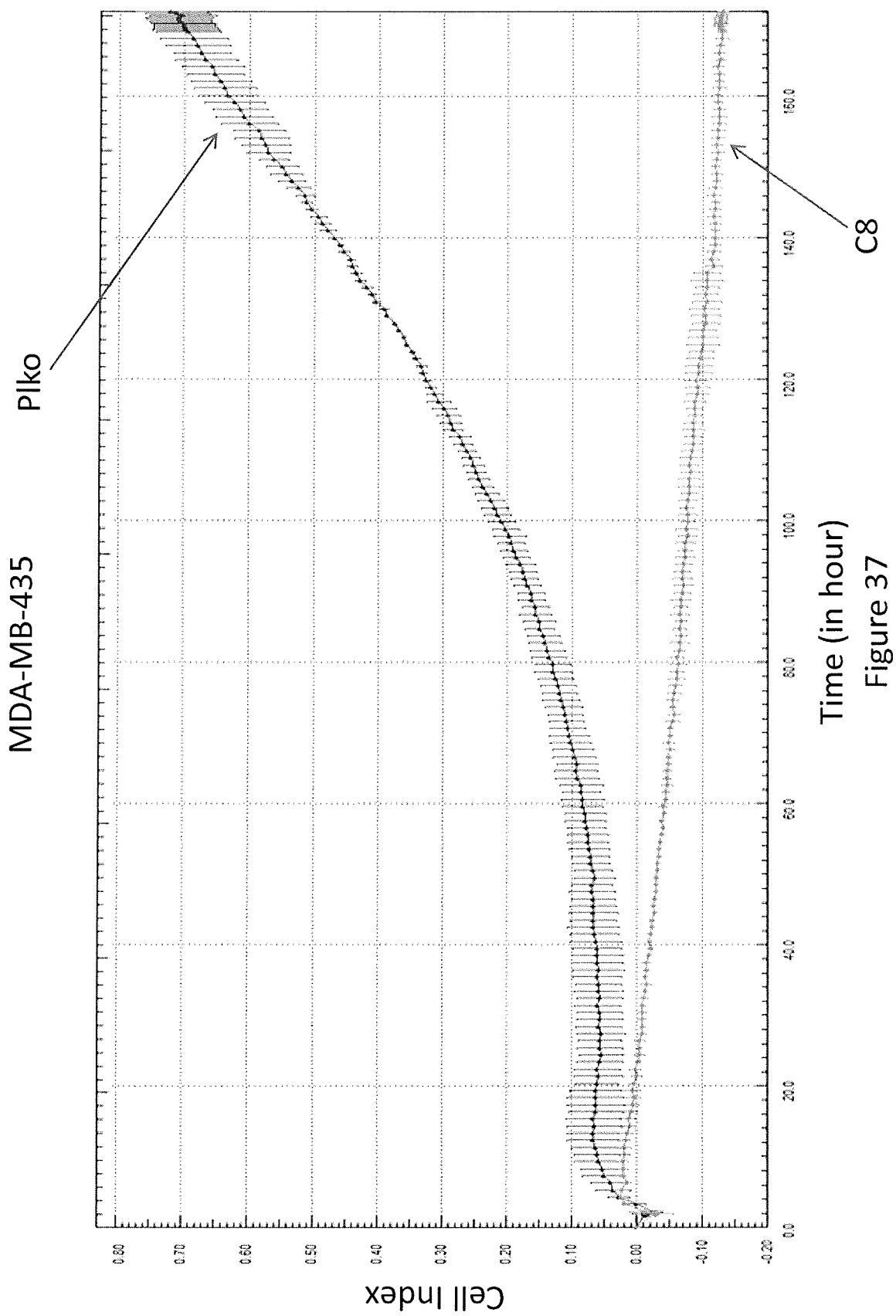
FIG. 37 shows the cell index from MDA-MB-435 (breast cancer) cells infected with an empty vector or C8 lentivirus encoding shRNA for TDG knockdown.
Figure 38:
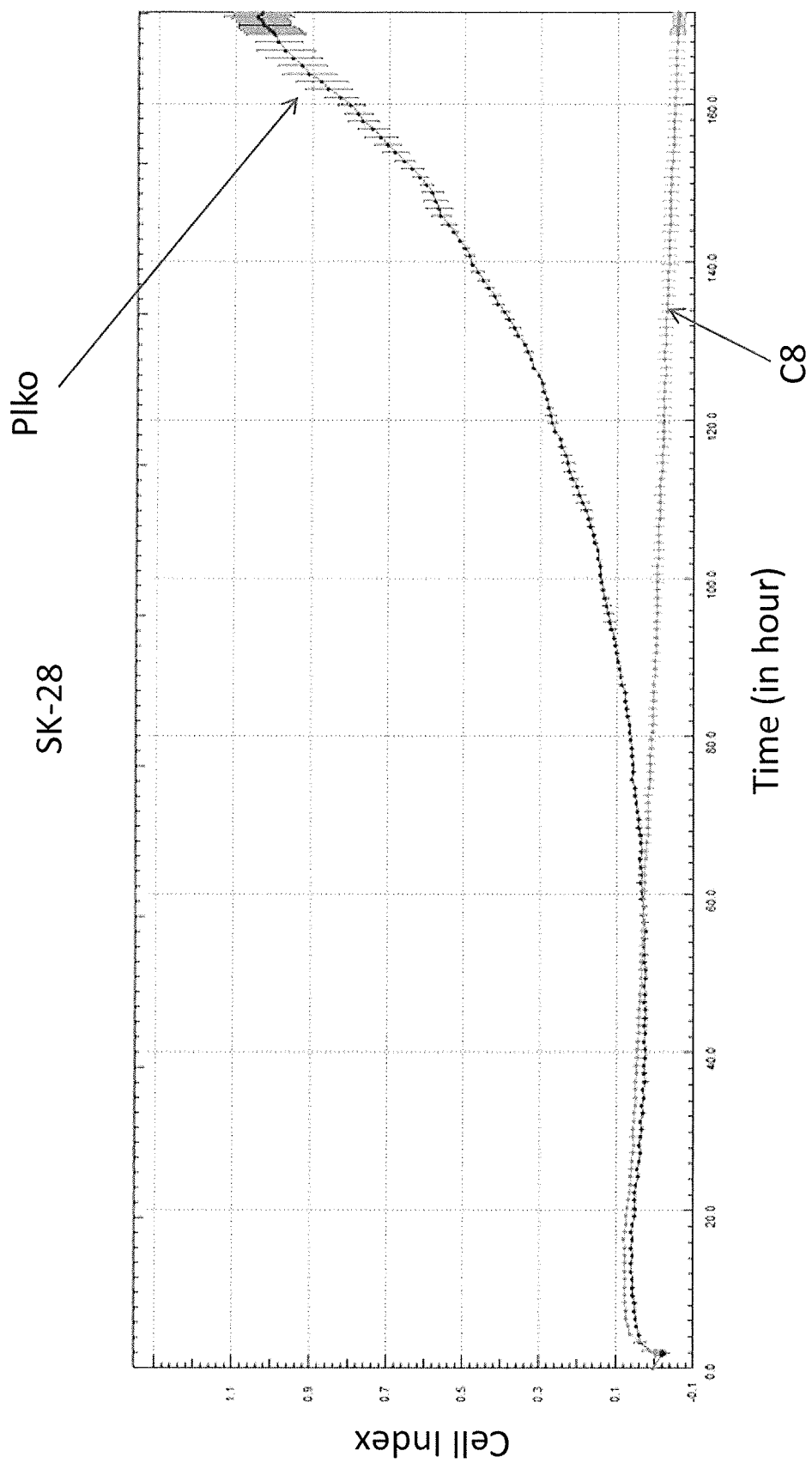
FIG. 38 shows the cell index from SK 28 (melanoma) cells infected with an empty vector or C8 lentivirus encoding shRNA for TDG knockdown.
Figure 39:
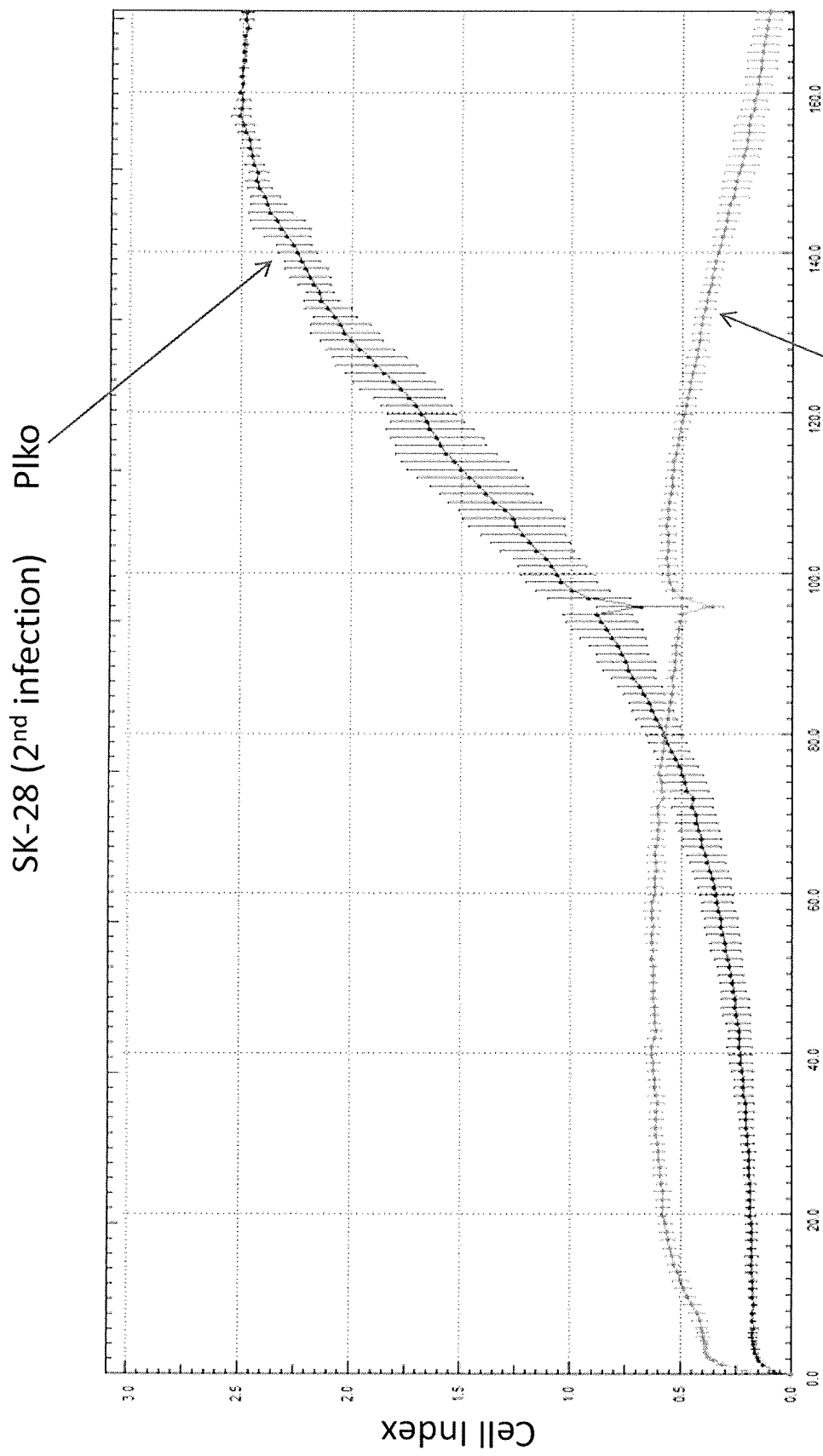
FIG. 39 shows the cell index from SK28 melanoma) cells infected (second infection) with an empty vector or C8 lentivirus encoding shRNA for TDG knockdown.
Figure 40:
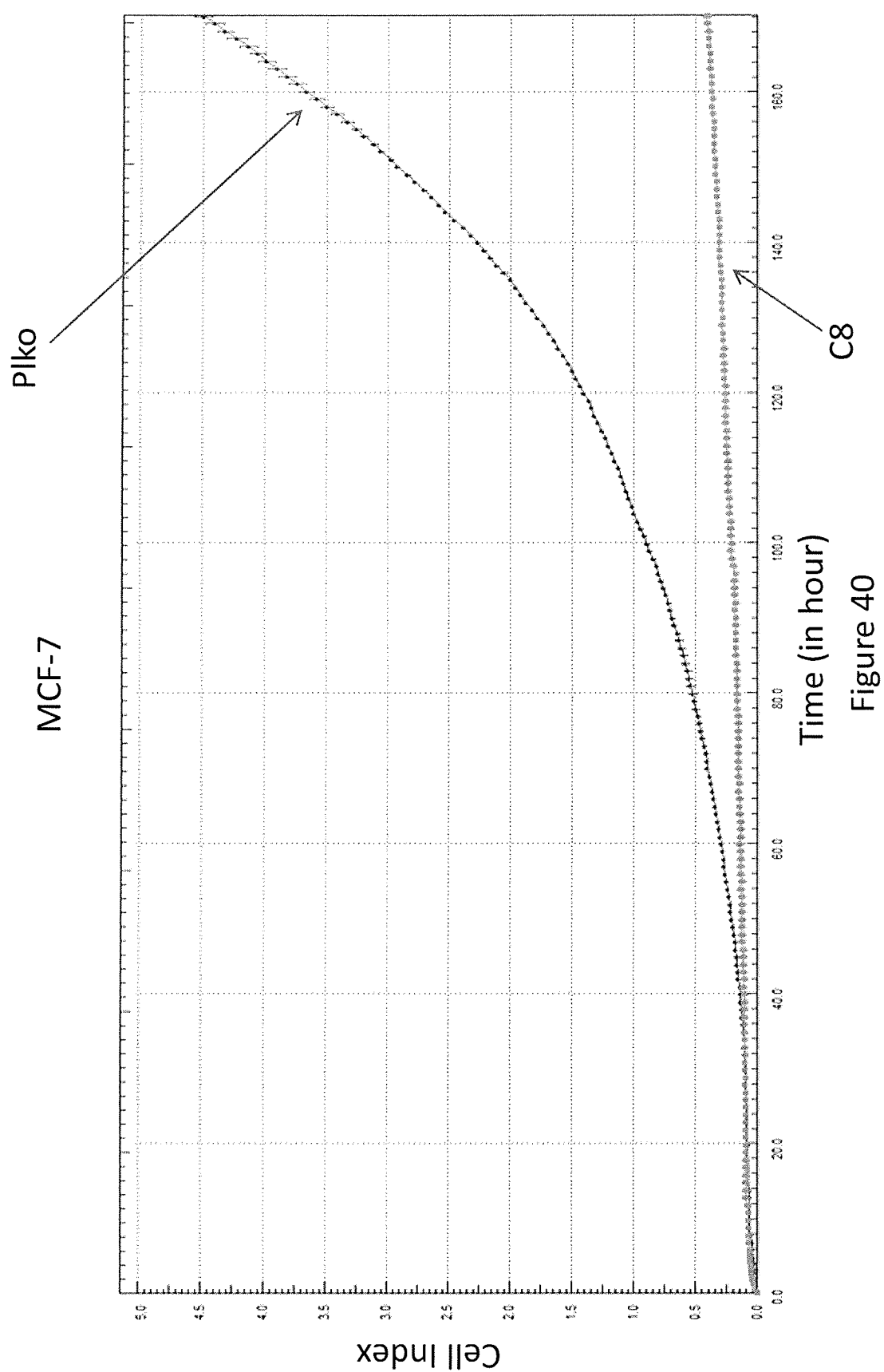
FIG. 40 shows the cell index from MCF-7 (breast cancer) cells infected with an empty vector or C8 lentivirus encoding shRNA for TDG knockdown.
Figure 41:
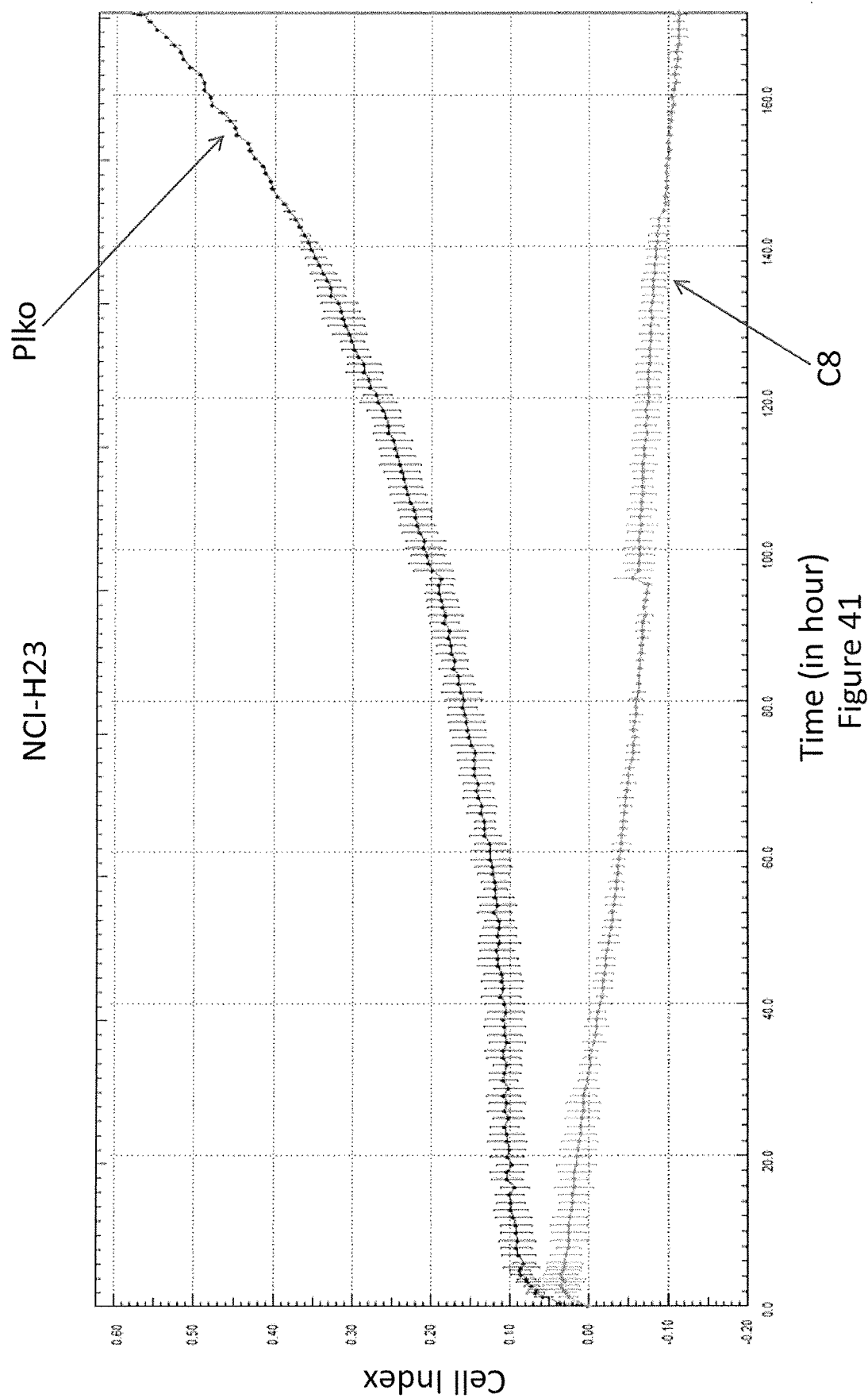
FIG. 41 shows the cell index from NCI-H23 (lung cancer) cells infected with an empty vector or C8 lentivirus encoding shRNA for TDG knockdown.

Vincristin is an inhibitor of mitosis that arrests cells in metaphase; it is used as a chemotherapeutic agent for leukemia/lymphoma and melanoma. It was observed that treatment of cancer cells with vincristine caused an increase of 5caC levels even in the absence of TDG downregulation; however, 5caC levels were further increased when vincristine treatment was combined with TDG downregulation (FIG. 31). This indicates that combinatorial treatment of cancer cells with vincristine plus TDG downregulation/inhibition can have a synergistic effect in killing cancer cells.

Example 16

TDG Down-Regulation Suppresses Proliferation of Multiple Cancer Cell Types

The effect of TDG down-regulation on the growth of various cancer cell types was investigated using the xCEL-Ligence® (Roche Diagnostics GmbH) real-time cell analyzer, a label-free, non-invasive method to monitor adherent cell behavior, including proliferation, spreading and compound-mediated cytotoxicity. The system is based on detecting impedance differences within an electrical circuit created in microelectrodes at the base of culture wells; these differences are converted into a cell index (CI), a value that is influenced by a variety of factors, such as cell number, cell size and cell adhesion. Over an incubation time of 160 hours, a marked difference in cell index was detected for cancer cell pairs, infected with either empty vector or C8 lentivirus, indicating that their proliferation was suppressed by TDG down-regulation (FIGS. 32-41). Cell lines from different cancer types decreased their proliferation upon TDG downregulation, including HCT-116 (colon cancer), HT-29 (rectosigmoid colon cancer), A549 and NCI-H23 (lung cancer), PC3 (prostate cancer), U251 (glioblastoma/brain cancer), MDA-MB-435 and MCF-7 (breast cancer); this analysis also confirmed that TDG downregulation decreased the proliferation of SK28 melanoma cells (FIG. 32-41). Similar data were obtained for pancreatic and ovarian cancer cells (data not shown).

Example 17

TDG Down-Regulation Induces Morphological Changes in Prostate Cancer Cells

Figure 42:
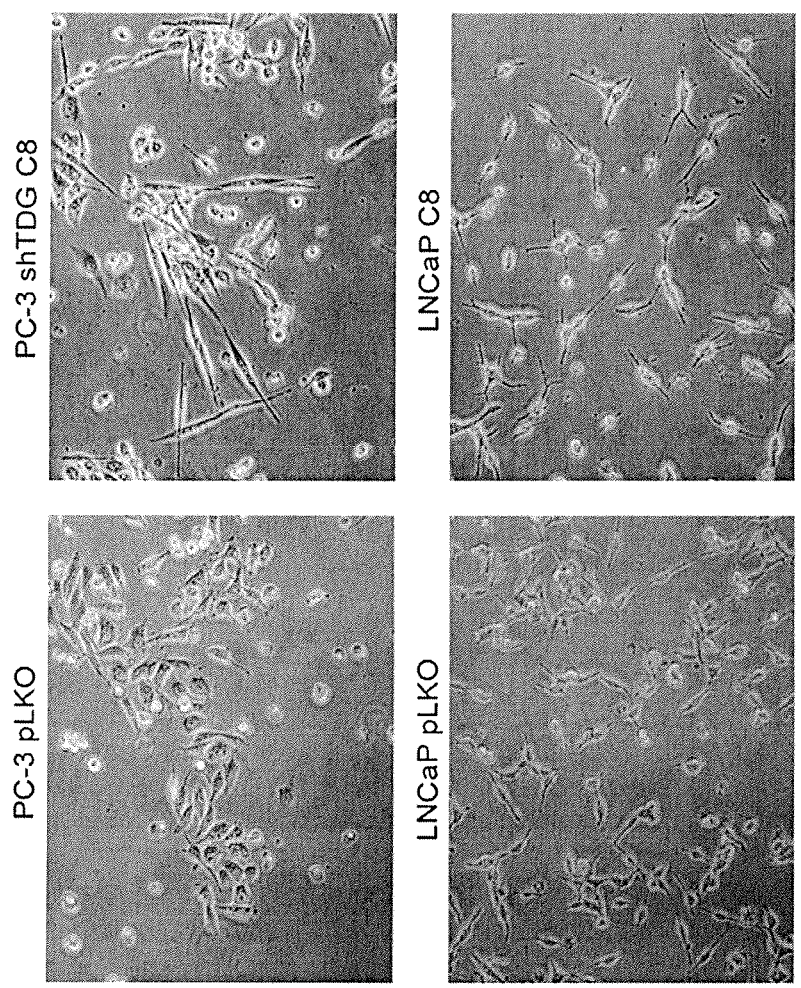
FIG. 42 shows morphologic changes in PC-3 and LNCap prostate cancer cells from TDG knockdown.

The effect of TDG down-regulation on the morphology of prostate cancer cells was tested. Much like what was observed in melanoma cell lines (FIG. 3, FIG. 5), both PC3 and LNCap cells developed numerous and long dendritic processes (FIG. 42). Without intending to be limited to any particular characterization, theory, or mechanism of action, it is believed that these changes, by analogy with the melanoma results, are likely due to the induction of senescence; however, it is also believed that it is possible that these changes may represent differentiation of the cells. These results were also observed in many other cancer cell types upon TDG downregulation (data not shown) such that it is believed that such morphologic changes may be a more generalized phenomenon beyond melanoma, prostate, and other cancers tested in accordance with this Example.

Example 18

Candidate TDG Inhibitors Induce Killing of Prostate Cancer Cells

Figure 43:
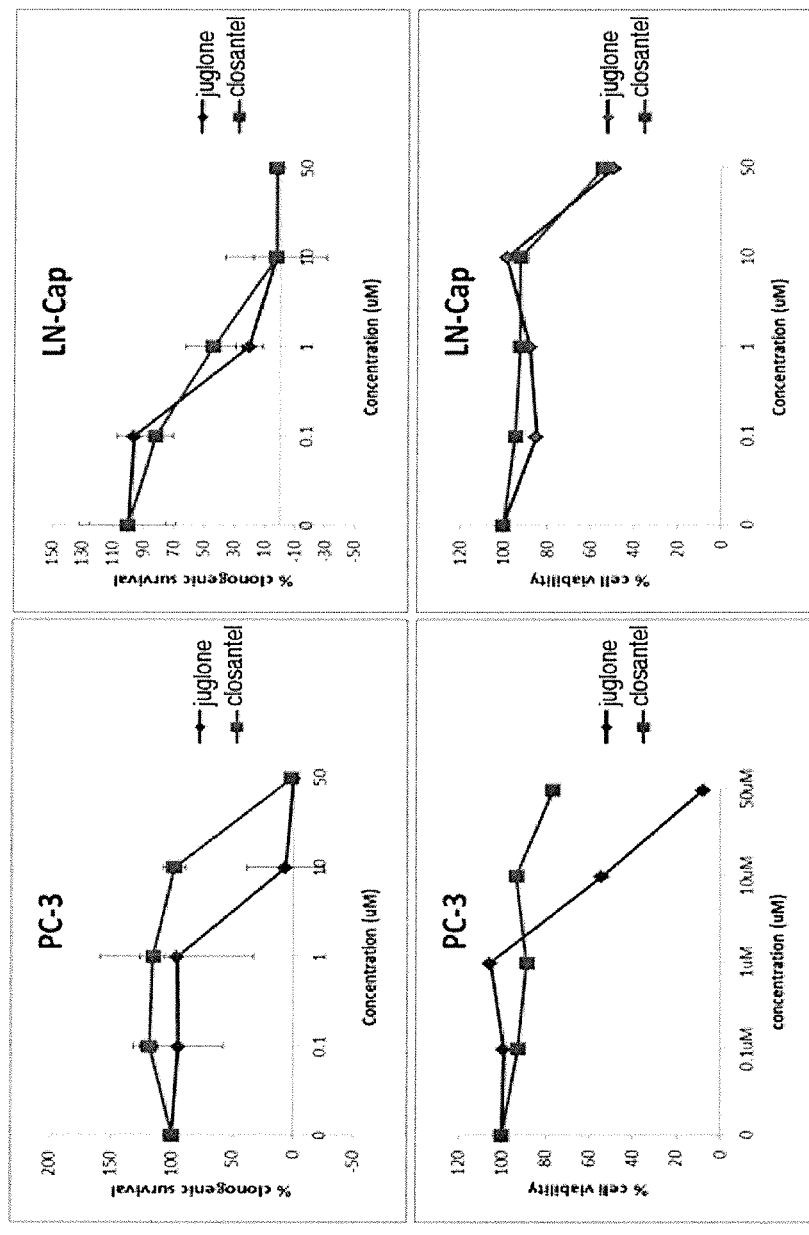
FIG. 43 shows TDG inhibitors induce the killing of prostate cancer cells.

The TDG inhibitors, juglone and closantel, were tested for their ability to kill PC3 and LNCaP prostate cancer cells. Consistent with the shRNA results, these compounds stopped proliferation of the prostate cancer cells, as determined by MTS and clonogenic assay (FIG. 43).

Example 19

TDG Down-Regulation Induces Senescence in Melanoma

Figure 44:
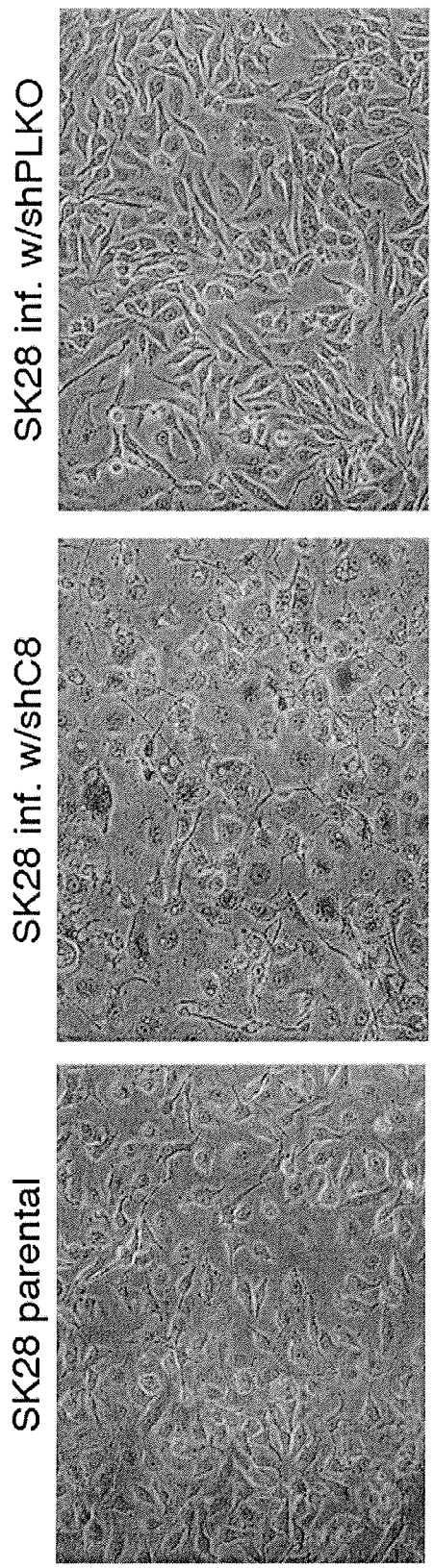
FIG. 44 shows that SK28 melanoma cells senesce upon TDG knockdown.

An important marker of senescence is the expression of endogenous lysosomal beta-galactosidase, which can be assayed by conducting a chromogenic beta-galactosidase assay at pH 6.0. This assay is called Senescence-associated beta-galactosidase staining (SA-β-gal). It was observed that SK28 melanoma cells are positive for SA-β-gal upon TDG downregulation (FIG. 44). It is believed that these data support the hypothesis that TDG downregulation induces senescence.

Example 20

Elevated 5-Carboxylcytosine (5caC) as a Biomarker of Pre-Malignant Conditions and Cancer It was hypothesized that some human premalignant and malignant conditions might be characterized by defects in TDG expression and/or biological activity, which, in turn, would lead to elevated 5caC levels, based on the pathway in FIG. 20. Since levels of 5caC are very low or undetectable in normal cells, detection of 5caC would represent a valuable biomarker for premalignant conditions and cancer.

Figure 45:
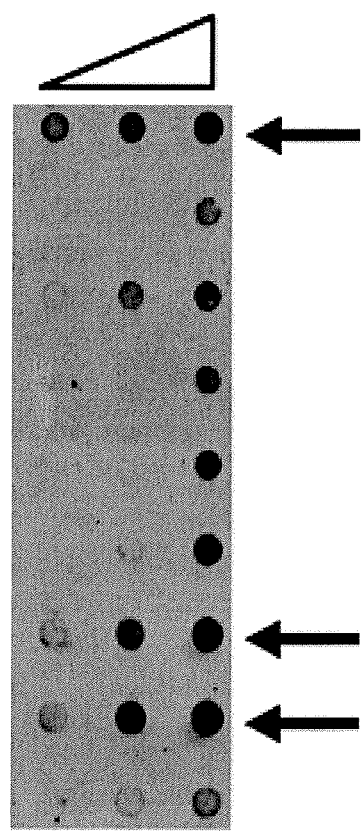
FIG. 45 shows increased 5-carboxylcytosine (5caC) levels in the bone marrow of myelodysplastic syndrome patients.

Myelodysplastic Syndrome (MDS) comprises a heterogeneous group of debilitating and malignant disorders of the hematopoietic tissue. They are characterized by uni- or multilineage dysplasia, ineffective hematopoiesis, peripheral cytopenias and increased risk of evolution into overt acute myeloid leukemia. An immuno-dot blot procedure was used in which serially diluted genomic DNA are blotted on a nitrocellulose membrane and then detected with an antibody anti-5caC. Analysis of bone marrow DNA samples from ~30 MDS patients revealed increased levels of 5caC in 8 cases (FIG. 45). FIG. 45 shows dilutions of genomic DNA (high to low from top to bottom) from bone marrow of MDS cases, blotted and detected with antibody anti-5caC; arrows mark cases with elevated 5caC. Thus, elevated 5caC defines a subset of MDS cases.

For melanoma, immunohistochemistry (IHC) was used to detect expression of TDG and levels of 5caC, using specific antibodies. The staining is very specific and allows detection of TDG and 5caC levels (FIG. 46). FIG. 46 shows IHC staining of a melanoma with anti-TDG (left, DAB-positive nuclei) and anti-5caC (right, VIP-positive nuclei) antibodies. Areas of the tumor that lost TDG expression (red contour) have higher levels of 5caC. Notably, the areas of the tumor with reduced expression of TDG and high levels of 5caC are morphologically distinct from areas of the tumor with expression of TDG retained and low levels of 5caC. While the latter have melanoma cells with bigger nuclei and low cell density, the former have melanoma cells with smaller nuclei and high cell density. Thus, without intending to be limited to any particular theory of mechanism of action, it is believed that reduced TDG and elevated 5caC may define melanomas with defined cytological features that could lead to different clinico-pathological characteristics.

The invention is not limited to the embodiments described and exemplified above, but is capable of variation and modification within the scope of the appended claims.

We claim:

1. A method of treating cancer in a patient in need thereof, the method comprising administering to the patient an inhibitor of thymine DNA glycosylase (TDG) in an amount effective to inhibit TDG in cancer cells, wherein the cancer is melanoma, prostate cancer, pancreatic cancer, breast cancer, colon cancer, lung cancer, or glioblastoma, and wherein the inhibitor of TDG is selected from the group consisting of hexadimethrine bromide, indigotindisulfonate, and protamine chloride.

2. The method according to claim 1, wherein the inhibitor of TDG is protamine chloride.

3. The method according to claim 1, wherein the cancer is melanoma.

4. The method according to claim 1, further comprising administering temozolomide to the patient.

5. The method according to claim 1, further comprising administering cisplatin to the patient.

6. The method according to claim 1, further comprising administering vincristine to the patient.

7. The method according to claim 1, wherein the method is a monotherapy.

* * * * *